United States Patent [19]
Goto et al.

[11] Patent Number: 5,273,974
[45] Date of Patent: Dec. 28, 1993

[54] CONDENSED HETEROCYCLIC COMPOUNDS, THEIR PRODUCTION AND USE

[75] Inventors: Giichi Goto, Toyono; Yuji Ishihara, Itami; Masaomi Miyamoto, Takarazuka, all of Japan

[73] Assignee: Takeda Chemical Industries, Ltd., Osaka, Japan

[21] Appl. No.: 796,430

[22] Filed: Nov. 22, 1991

[30] Foreign Application Priority Data

Nov. 22, 1990 [JP] Japan ................. 2-319897
Jan. 14, 1991 [JP] Japan ................. 3-070286
Aug. 21, 1991 [JP] Japan ................. 3-209358
Sep. 24, 1991 [JP] Japan ................. 3-243768

[51] Int. Cl.$^5$ ............. C07D 401/10; C07D 405/10; C07D 409/10; A61K 31/445
[52] U.S. Cl. ........................ 514/221; 514/307; 514/314; 514/323; 540/593; 540/594; 540/595; 540/481; 546/146; 546/168; 546/201
[58] Field of Search ............. 540/593, 594, 595, 481; 514/221, 307, 314, 323; 546/146, 168, 201

[56] References Cited

U.S. PATENT DOCUMENTS

| | | | |
|---|---|---|---|
| 4,064,255 | 12/1977 | Champseixed et al. | 546/202 |
| 4,208,417 | 6/1980 | Uzan | 546/202 |
| 4,849,431 | 7/1989 | Sugimoto et al. | 546/202 |
| 4,895,841 | 1/1990 | Sugimoto et al. | 546/202 |

FOREIGN PATENT DOCUMENTS

| | | | |
|---|---|---|---|
| 0378207 | 7/1990 | European Pat. Off. | 546/202 |
| 9103243 | 8/1990 | World Int. Prop. O. | 546/202 |

OTHER PUBLICATIONS

Marx, Science, vol. 250, 1990 pp. 1509-1510.
Thompson et al. New England J. Medicine vol. 323 (7), 1990, pp. 445-448.
Ember, Chemical, and Eng. News, Apr. 8, 1991, pp. 30-31, and 35.
Rajsner, et al., Chemical Abstracts, vol. 101, 1984 Abstract, 38369u.
Shutske, et al., J. Med. Chem. 32, 1805-1813, 1989
Merck Index (Rahway N.J., Merck and Co. (1989) pp. 572-573.
Burger's Medicinal Chemistry, 4th Ed. p. 922 (New York, J. Wiley and Sons, 1987).
Havera, J. Med. Chem. 12, (1969) pp. 580-583.
Ivanova, et al. Chemical Abstracts, vol. 116, (1992) Abstract 6435f.

Primary Examiner—Mukund J. Shah
Assistant Examiner—P. K. Sripada
Attorney, Agent, or Firm—Wegner, Cantor, Mueller & Player

[57] ABSTRACT

A condensed heterocyclic derivative of the formula (I):

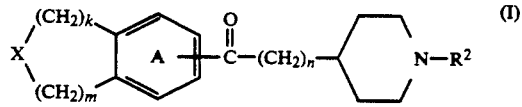

wherein X is an oxygen atom, a sulfur atom or $R^1$—N< wherein $R^1$ is a hydrogen atom, a hydrocarbon group which may be substituted or an acyl group which may be substituted; $R^2$ is a hydrogen atom or a hydrocarbon group which may be substituted; ring A is a benzene ring which may be substituted, k is a whole number of 0 to 3; m is a whole number of 1 to 8; and n is a whole number of 1 to 6, or a pharmaceutically acceptable salt thereof exhibiting high colinesterase inhibitory activity, and a method for producing the same.

35 Claims, No Drawings

CONDENSED HETEROCYCLIC COMPOUNDS, THEIR PRODUCTION AND USE

The present invention relates to novel condensed heterocyclic compounds or their salt. The compounds of the invention are useful as a medicine and a cholinesterase inhibitor and specifically as a therapeutic or/and prophylactic agent for senile dementia, Alzheimer's disease and so on.

In these days of aging society, there has been proposed a variety of compounds which have therapeutic and prophylactic efficacy for senile dementia. It has been found that physostigmine, a naturally-occurring cholinesterase inhibitor, has therapeutic and or prophylactic activity for senile dementia. However, physostigmine has the drawbacks of a short duration of action, high toxicity and so on.

Meanwhile, as synthetic drugs for a colinesterase inhibitor, depressant or so, a variety of heterocyclic compounds have been proposed (e.g. U.S. Pat. No. 4,064,255, U.S. Pat. No. 4,208,417, U.S. Pat. No. 4,849,431, U.S. Pat. No. 4,895,841, Japanese Publish unexamined patent application No. 169569/1990 and EP-A-0,378,207).

However, what is needed now is a compound which is more active, longer-acting and less toxic than the compounds already known to have therapeutic and or prophylactic efficacy for senile dementia.

The present invention provides a novel class of compounds which is useful as a cholinesterase inhibitor and particularly as a therapeutic and or prophylactic agent for senile dementia, Alzheimer's disease and so on.

The inventors of present invention explored compounds which could be of use as medicament for improving the functions of the the central nervous system and particularly compounds of value for the relief of senile dementia, Alzheimer's disease and so on due to brain ischemia and succeeded in the creation of a condensed heterocyclic compound of the formula (I):

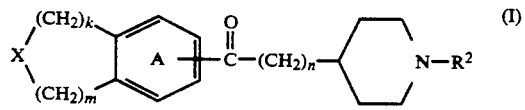

wherein X is an oxygen atom, a sulfur atom or $R^1$—N< wherein $R^1$ is a hydrogen atom, a hydrocarbon group which may be substituted or an acyl group which may be substituted; $R^2$ is a hydrogen atom or a hydrocarbon group which may be substituted; ring A is a benzene ring which may be substituted; k is a whole number of 0 to 3; m is a whole number of 1 to 8; and n is a whole number of 1 to 6, or a salt thereof.

The compound (I) or its salt according to the present invention is structurally characterized in that the hetero atom (O,S or N)-containing heterocycle fused to the benzene ring is a saturated ring and that a substituent group of the formula:

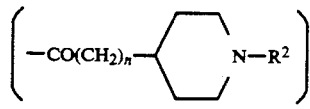

is bound directly to a carbon atom of the benzene ring. This compound is believed to be a novel compound which has not been disclosed in the literature.

Referring to the above formula (I), the "hydrocarbon group" of "the hydrocarbon group which may be substituted" as designated by $R^1$ and $R^2$ includes acyclic, cyclic, saturated, unsaturated or their optionally combined hydrocarbon groups.

The acyclic saturated hydrocarbon group includes straight-chain or branched $C_{1-11}$ alkyl groups (e.g. methyl, ethyl, n-propyl, i-propyl, n-butyl, i-butyl, tert-butyl, n-pentyl, n-hexyl).

The acyclic unsaturated hydrocarbon group includes straight-chain or branched $C_{2-4}$ alkenyl groups (e.g. vinyl, allyl, 2-butenyl) and $C_{2-4}$ alkynyl groups (e.g. propargyl, 2-butynyl)

The cyclic saturated hydrocarbon group includes $C_{3-7}$ monocyclic cycloalkyl groups (e.g. cyclobutyl, cyclopentyl, cyclohexyl) and $C_{8-14}$ bridged cyclic saturated hydrocarbon groups (e.g. bicyclo[3.2.1]oct-2-yl, bicyclo[3.3.1]non-2-yl, adamantan-1-yl)

The cyclic unsaturated hydrocarbon group includes phenyl, naphthyl and so on.

The "hydrocarbon group" of the "hydrocarbon group which may be substituted" as designated by $R^1$ and $R^2$ may be an optionally combined hydrocarbon group representing an optional combination of the abovementioned acyclic, cyclic, saturated and unsaturated hydrocarbon groups, such as $C_{7-18}$ aralkyl (Such as phenyl $C_{1-12}$ alkyl and α-naphthy $C_{1-8}$ alkyl, e.g. phenylmethyl, phenylethyl, phenylpropyl, phenylbutyl, phenylpentyl, phenylhexyl, α-naphthylmethyl), $C_{8-18}$ arylalkenyl (such as aryl $C_{2-12}$ alkenyl, e.g. styryl, cinnamyl, 4-phenyl-2-butenyl, 4-phenyl-3-butenyl), $C_{8-18}$ arylalkynyl (such as aryl $C_{2-12}$ alkynyl, e.g. phenylethynyl, 3-phenyl-2-propynyl, 3-phenyl-propynyl), $C_{3-7}$ cycloalkyl-$C_{1-6}$ alkyl (e.g. cyclopropylmethyl, cyclobutylmethyl, cyclopentylmethyl, cyclohexylmethyl, cycloheptylmethyl, cyclopropylethyl, cyclobutylethyl, cyclopentylethyl, cyclohexylethyl, cycloheptylethyl, cyclopropylbutyl, cyclobutylbutyl, cyclopentylbutyl, cyclohexylbutyl, cycloheptylbutyl, cyclopropylpentyl, cyclobutylpentyl, cyclopentylpentyl, cyclohexylpentyl, cycloheptylpentyl, cyclopropylhexyl, cyclobutylhexyl, cyclopentylhexyl, cyclohexylhexyl, cycloheptylhexyl) groups and so on.

The preferable examples of the "hydrocarbon group" of the "hydrocarbon group which may be substituted" as designated by $R^1$ include a straight-chain or branched $C_{1-7}$ alkyl group (e.g. methyl, ethyl, n-propyl, i-propyl, n-butyl, i-butyl, tert-butyl, n-pentyl, n-hexyl) or a $C_{7-10}$ aralkyl group (e.g. phenylmethyl, phenylethyl, phenylpropyl) and the preferable examples of the "hydrocarbon group" of the "hydrocarbon group which may be substituted" as designated by $R^2$ include a $C_{7-10}$ aralkyl (e.g. phenylmethyl, phenylethyl, phenylpropyl).

The acyclic saturated, acyclic unsaturated and cyclic saturated hydrocarbon groups mentioned above for $R^1$ and $R^2$ may be substituted by 1 to 5 substituents selected from the group consisting of halogen (e.g. fluoro, chloro, bromo, iodo), nitro, cyano, hydroxy, $C_{1-4}$ alkoxy (e.g. methoxy, ethoxy, propyloxy, butyloxy, isopropyloxy), $C_{1-4}$ alkylthio (e.g. methylthio, ethylthio, propylthio), amino, mono- or di-$C_{1-4}$ alkylsubstituted amino (e.g. methylamino, ethylamino, propylamino, dimethylamino, diethylamino), cyclic amino (e.g. pyrrolidino, piperidino, morpholino), $C_{1-4}$ alkylcarbonylamino (e.g. acetylamino, propionylamino, butyrylamino), $C_{1-4}$ alkylsulfonylamino (e.g. methylsulfonylamino, ethylsulfonylamino), $C_{1-4}$ alkoxycarbonyl (e.g. methoxycarbonyl, ethoxycarbonyl, propoxycarbonyl), hydroxycarbonyl, $C_{1-6}$ alkylcarbonyl (e.g. methylcarbonyl, ethylcarbonyl, propylcarbonyl), carbamoyl, mono- or di-$C_{1-4}$ alkyl-substituted carbamoyl (e.g. methylcarbamoyl, ethylcarbamoyl), $C_{1-6}$ alkylsulfonyl (e.g. methylsufonyl, ethylsulfonyl, propylsulfonyl) and so on.

The substituents on the "benzene ring which may be substituted" as designated by ring A in formula (I) and the substituents on the cyclic unsaturated hydrocarbon group as designated by $R^1$ and $R^2$ include $C_{1-4}$ alkyl (e.g. methyl, ethyl, propyl, butyl), halogen (e.g. fluoro, chloro, bromo, iodo), nitro, cyano, hydroxy, $C_{1-4}$ alkoxy (e.g. methoxy, ethoxy, propyloxy, butyloxy, isopropyloxy), $C_{1-4}$ alkylthio (e.g. methylthio, ethylthio, propylthio, isopropylthio, butylthio), amino, mono- or di-$C_{1-4}$ alkyl-substituted amino (e.g. methylamino, ethylamino, propylamino, dimethylamino, diethylamino), cyclic amino (e.g. pyrrolidino, piperidino, morpholino), $C_{1-4}$ alkylcarbonylamino (e.g. acetylamino, propionylamino, butyrylamino), aminocarbonyloxy, mono- or di-$C_{1-4}$ alkyl-substituted aminocarbonyloxy (e.g. methylaminocarbonyloxy, ethylaminocarbonyloxy, dimethylaminocarbonyloxy, diethylaminocarbonyloxy), $C_{1-4}$ alkylsufonylamino (e.g. methylsulfonylamino, ethylsulfonylamino, propylsulfonylamino), $C_{1-4}$ alkoxycarbonyl (e.g. metoxycarbonyl, ethoxycarbonyl, propoxycarbonyl, isobutoxycarbonyl), hydroxycarbonyl, $C_{1-6}$ alkylcarbonyl (e.g. methylcarbonyl, ethylcarbonyl, butylcarbonyl), $C_{3-6}$ cycloalkylcarbonyl (e.g. cyclohexylcarbonyl), carbamoyl, mono- or di-$C_{1-4}$ alkyl-substituted carbamoyl (e.g. methylcarbamoyl, ethylcarbamoyl, propylcarbamoyl, butylcarbamoyl, diethylcarbamoyl, dibutylcarbamoyl) $C_{1-4}$ alkylsulfonyl (e.g. methylsulfonyl, ethylsulfonyl, propylsulfonyl) and $C_{3-6}$ cycloalkylsulfonyl (e.g. cyclopentylsulfonyl, cyclohexylsulfonyl) as well as a phenyl, naphthyl, phenoxy, benzoyl, phenoxycarbonyl, phenyl-$C_{1-4}$ alkylcarbamoyl (e.g. phenylmethylcarbamoyl, phenylethylcarbamoyl, phenylpropylcarbamoyl), phenylcarbamoyl, phenyl-$C_{1-4}$ alkylcarbonylamino (e.g. phenylmethylcarbonylamino, phenylethylcarbonylamino), benzoylamino, phenyl-$C_{1-4}$ alkylsulfonyl (e.g. phenylmethylsulfonyl, phenylethylsulfonyl), phenylsulfonyl, phenyl-$C_{1-4}$ alkylsulfinyl (e.g. phenylmethylsulfinyl, phenylethylsulfinyl), phenyl-$C_{1-4}$ alkylsulfonylamino (e.g. phenylmethylsulfonylamino, phenylethylsulfonylamino) or phenylsulfonylamino which may have 1 to 4 substituents, for example selected from the group consisting of $C_{1-4}$ alkyl groups such as methyl, ethyl, propyl, butyl, isopropyl, etc., $C_{1-4}$ alkoxy groups such as methoxy, ethoxy, n-propyloxy, i-propyloxy, n-butyloxy, etc., halogen such as chloro, bromo and iodo, hydroxy, benzyloxy, amino, mono- or di-$C_{1-4}$ alkyl-substituted amino such as mentioned above, nitro, and $C_{1-6}$ alkylcarbonyl such as mentioned above and so on. The appropriate number of such substituents on the benzene ring or cyclic unsaturated hydrocarbon group is 1 to 3.

The optionally combined hydrocarbon group as designated by $R^1$ and $R^2$ may be substituted by 1 to 5 substituents selected from the group consisting of $C_{1-4}$ alkyl (e.g. methyl, ethyl, propyl, butyl), halogen (e.g. fluoro, chloro, bromo, iodo), nitro, cyano, hydroxy, $C_{1-4}$ alkoxy (e.g. methoxy, ethoxy, propyloxy, butyloxy, isopropyloxy), $C_{1-4}$ alkylthio (e.g. methylthio, ethylthio, propylthio, isopropylthio, butylthio), amino, mono- or di-$C_{1-4}$ alkyl-substituted amino (e.g. methylamino, ethylamino, propylamino, di-methylamino, diethylamino), cyclic amino (e.g. pyrrolidino, piperidino, morpholino), $C_{1-4}$ alkylcarbonylamino (e.g. acetylamino, propionylamino, butyrylamino), aminocarbonyloxy, mono- or di-$C_{1-4}$ alkylsubstituted aminocarbonyloxy (e.g. methylaminocarbonyloxy, ethylaminocarbonyloxy, dimethylaminocarbonyloxy, diethylaminocarbonyloxy), $C_{1-4}$ alkylsufonylamino (e.g. methylsulfonylamino, ethylsulfonylamino, propylsulfonylamino), $C_{1-4}$ alkoxycarbonyl (e.g. metoxycarbonyl, ethoxycarbonyl, propoxycarbonyl, isobutoxycarbonyl), hydroxycarbonyl, $C_{1-6}$ alkylcarbonyl (e.g. methylcarbonyl, ethylcarbonyl, butylcarbonyl), $C_{3-6}$ cycloalkylcarbonyl (e.g. cyclohexylcarbonyl), carbamoyl, mono- or di-$C_{1-4}$ alkyl-substituted carbamoyl (e.g. methylcarbamoyl, ethylcarbamoyl, propylcarbamoyl, butylcarbamoyl, diethylcarbamoyl, dibutylcarbamoyl) $C_{1-4}$ alkylsulfonyl (e.g. methylsulfonyl, ethylsulfonyl, propylsulfonyl) and $C_{3-6}$ cycloalkylsulfonyl (e.g. cyclopentylsulfonyl, cyclohexylsulfonyl) as well as a phenyl, naphthyl, phenoxy, benzoyl, phenoxycarbonyl, phenyl-$C_{1-4}$ alkylcarbamoyl (e.g. phenylmethylcarbamoyl, phenylethylcarbamoyl, phenylpropylcarbamoyl), phenylcarbamoyl, phenyl-$C_{1-4}$ alkylcarbonylamino (e.g. phenylmethylcarbonylamino, phenylethylcarbonylamino), benzoylamino, phenyl-$C_{1-4}$ alkylsulfonyl (e.g. phenylmethylsulfonyl, phenylethylsulfonyl), phenylsulfonyl, phenyl-$C_{1-4}$ alkylsulfinyl (e.g. phenylmethylsulfinyl, phenylethylsulfinyl), phenyl-$C_{1-4}$ alkylsulfonylamino (e.g. phenylmethylsulfonylamino, phenylethylsulfonylamino) or phenylsulfonylamino which may have 1 to 4 substituents, for example selected from the group consisting of $C_{1-4}$ alkyl groups such as methyl, ethyl, propyl, butyl, isopropyl, etc., $C_{1-4}$ alkoxy groups such as methoxy, ethoxy, n-propyloxy, i-propyloxy, n-butyloxy, etc., halogen such as chloro, bromo and iodo, hydroxy, benzyloxy, amino, mono- or di-$C_{1-4}$ alkyl-substituted amino such as mentioned above, nitro, and $C_{1-6}$ alkylcarbonyl such as mentioned above and so on.

The "acyl" of the "acyl group which may be substituted" as designated by $R^1$ includes carboxylic acid acyl groups (e.g. formyl, $C_{2-8}$ alkyl- or phenylcarbonyl groups such as acetyl, propionyl, butyryl, benzoyl, etc.), sulfonic acid acyl groups (e.g. $C_{1-7}$ alkyl- or phenylsulfonyl groups such as methanesulfonyl, benzenesulfonyl, p-toluensulfonyl, etc.), phosphonic acid acyl groups (e.g. $C_{1-7}$ alkyl- or phenylphosphonyl groups such as methanephosphonyl, benzenephosphonyl, etc.), and substituted oxycarbonyl groups (e.g. $C_{2-8}$ alkyloxycarbonyl or $C_{7-8}$-aralkyloxy-carbonyl groups such as methyloxycarbonyl, tert-butyloxycarbonyl, benzyloxycarbonyl, etc.).

Each of these acyl groups may optionally have 1 to 3, preferably 1 to 2, substituents such as halogen (e.g. fluoro, chloro, bromo, iodo), amino, $C_{1-6}$ alkyl or $C_{3-6}$ cycloalkyl-substituted primary or secondary amino (e.g. methylamino, ethylamino, propylamino, cyclohexylamino, dimethylamino, diethylamino, diisopropylamino, dicyclohexylamino), $C_{1-4}$ alkoxy (e.g. methoxy, ethoxy, propoxy) and so on.

X is preferably $R^1$—N< and especially R is preferably hydrogen, methyl, ethyl, benzyl, acetyl, benzoyl, methoxycarbonyl or ethoxycarbonyl.

$R^2$ is preferably a benzyl or α-naphthylmethyl group which is either unsubstituted or substituted by 1 or 2 substituents selected from the group consisting of halogen (e.g. fluoro, chloro), methyl, nitro and/or methoxy and more preferable examples of $R^2$ include an unsubstituted benzyl.

The substituent on ring A is preferably fluoro, chloro, trifluoromethyl, methyl or methoxy, and more preferably fluoro.

The preferred k and m are such that when the sum of k and m is a whole number of 2 to 6; that is when

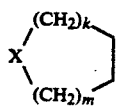

forms a 5 to 9 membered ring.

The preferred combination of k and m is such that when k is 0, m is 2, 3, 4 or 5; when k is 1, m is 1, 2 or 3; or when k is 2, m is 2. Thus, the preferred nitrogen-containing condensed heterocyclic rings which are represented by

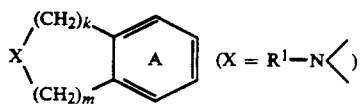

are 2,3-dihydro-1H-indole, 1,2,3,4-tetrahydroquinoline, 2,3,4,5-tetrahydro-1H-1-benzazepine, 2,3-dihydro-1H-isoindole, 1,2,3,4-tetrahydroisoquinoline, 2,3,4,5-tetrahydro-1H-2-benzazepine, 2,3,4,5-tetrahydro-1H-3benzazepine, 1,2,3,4,5,6-hexahydro-1-benzazocine, 1,2,3,4,5,6-hexahydro-2-benzazocine, 1,2,3,4,5,6-hexahydro-3-benzazocine, 2,3,4,5,6,7-hexahydro-1H-1-benzazonine, 2,3,4,5,6,7-hexahydro-1H-2-benzazonine, 2,3,4,5,6,7-hexahydro-1H-3-benzazonine, 2,3,4,5,6,7-hexahydro-1H-4-benzazonine.

The preferred oxygen-containing condensed heterocyclic rings which are represented by

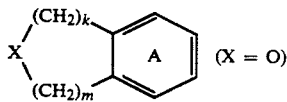

are 2,3-dihydrobenzofuran, 1,3-dihydroisobenzofuran, 3,4-dihydro-2H-1-benzopyran, 2,3,4,5-tetrahydro-1-benzoxepin, 1,3,4,5-tetrahydro-2-benzoxepin, 1,2,4,5-tetrahydro-3-benzoxepin, 3,4,5,6-tetrahydro-2H-1-benzoxocin, 3,4,5,6-tetrahydro-1H-2-benzoxocin, 1,4,5,6-tetrahydro-2H-3-benzoxocin, 2,3,4,5,6,7-hexahydro-1-benzoxonin, 1,3,4,5,6,7-hexahydro-2-benzoxonin, 1,2,4,5,6,7-hexahydro-4-benzoxonin, 1,2,3,5,6,7-hexahydro-4-benzoxonin.

The preferred sulfur-containing condensed heterocyclic rings which are represented by

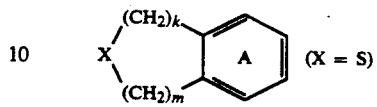

are 2,3-dihydro[b]thiophen, 1,3-dihydrobenzo[c]thiophen, 3,4-dihydro-2H-1-benzothiopyran, 3,4-dihydro-1H-2-benzothiopyran, 2,3,4,5-tetrahydro-1-benzothiepin, 1,3,4,5-tetrahydro-2-benzothiepin, 1,2,4,5-tetrahydro-3-benzothiepin, 3,4,5,6-tetrahydro-2H-1-benzothiocin, 3,4,5,6-tetrahydro-1H-2-benzothiocin, 1,4,5,6-tetrahydro-2H-3benzothiocin, 2,3,4,5,6,7-hexahydro-1-benzothionin, 1,3,4,5,6,7-hexahydro-2-benzothionin, 1,2,4,5,6,7-hexahydro-3-benzothionin, 1,2,3,5,6,7-hexahydro-4-benzothionin.

The more preferred heterocyclic rings which are represented by

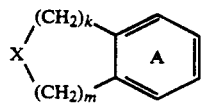

wherein each symbol is as defined above, include

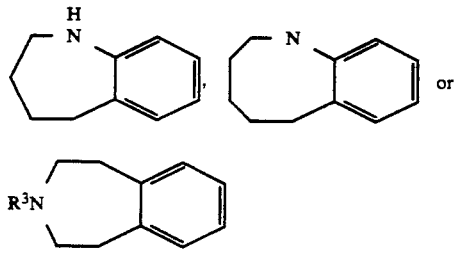

wherein $R^3$ is a hydrogen atom or a $C_{1-3}$ alkyl group. The $C_{1-3}$ alkyl group of $R^3$ includes methyl, ethyl, propyl and iso-propyl.

The preferred example of n is 1,2 or 3, and more preferably 2.

Specifically, the following compounds of formula (I) and their salts thereof are preferred.

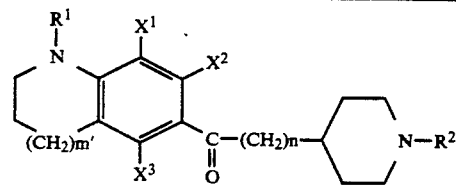

| No. | m' | n | $X^1$ | $X^2$ | $X^3$ | $R^1$ | $R^2$ |
|---|---|---|---|---|---|---|---|
| 1 | 1 | 2 | H | H | H | H | $CH_2Ph$ |
| 2 | 1 | 2 | H | H | H | $CH_3$ | $CH_2Ph$ |
| 3 | 1 | 2 | H | H | H | $C_2H_5$ | $CH_2Ph$ |
| 4 | 1 | 2 | H | H | H | $CH_2Ph$ | $CH_2Ph$ |
| 5 | 1 | 2 | H | H | H | $COCH_3$ | $CH_2Ph$ |
| 6 | 1 | 2 | H | H | H | $COPh$ | $CH_2Ph$ |
| 7 | 1 | 2 | $CH_3$ | H | H | $CH_3$ | $CH_2Ph$ |

| | | | | | | | |
|---|---|---|---|---|---|---|---|
| 8 | 1 | 2 | H | F | CH$_3$ | CH$_3$ | CH$_2$Ph |
| 9 | 1 | 2 | H | Cl | H | CH$_3$ | CH$_2$Ph |
| 10 | 1 | 2 | CH$_3$ | OCH$_3$ | H | CH$_3$ | CH$_2$Ph |
| 11 | 1 | 2 | OCH$_3$ | F | H | CH$_3$ | CH$_2$Ph |
| 12 | 1 | 2 | F | F | H | CH$_3$ | CH$_2$Ph |
| 13 | 1 | 2 | OCH$_3$ | Cl | H | CH$_3$ | CH$_2$Ph |
| 14 | 1 | 2 | F | F | OCH$_3$ | CH$_3$ | CH$_2$Ph |
| 15 | 1 | 2 | Cl | CH$_3$ | F | CH$_3$ | CH$_2$Ph |
| 16 | 1 | 2 | H | H | H | CH$_3$ | CH$_2$CH$_2$Ph |
| 17 | 1 | 2 | H | H | H | CH$_3$ | 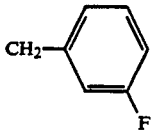 |
| 18 | 1 | 2 | H | H | H | CH$_2$Ph | 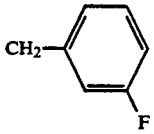 |
| 19 | 1 | 2 | H | H | H | H | 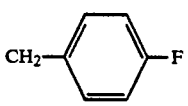 |
| 20 | 1 | 2 | H | H | H | H | 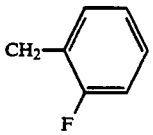 |
| 21 | 1 | 2 | H | H | H | CH$_3$ | 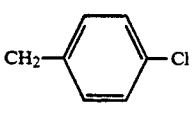 |
| 22 | 1 | 2 | H | H | H | CH$_3$ | 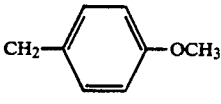 |
| 23 | 1 | 2 | H | H | H | CH$_3$ | 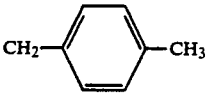 |
| 24 | 1 | 2 | CF$_3$ | F | H | H | 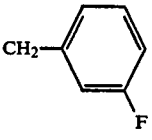 |
| 25 | 1 | 2 | Cl | H | H | H | 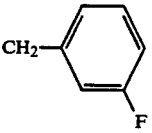 |
| 26 | 1 | 2 | OCH$_3$ | F | CH$_3$ | CH$_3$ | 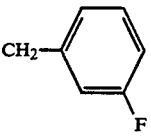 |

-continued
| | | | | | | | |
|---|---|---|---|---|---|---|---|
| 27 | 1 | 2 | H | F | Cl | CH₃ | 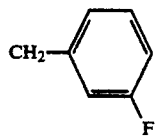 |
| 28 | 1 | 2 | CH₃ | H | H | H | 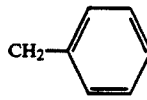 |
| 29 | 1 | 2 | Cl | H | H | H | 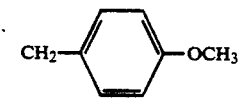 |
| 30 | 1 | 2 | CH₃ | H | H | CH₃ | 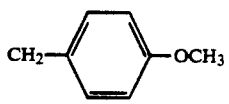 |
| 31 | 1 | 2 | F | H | Cl | CH₃ | 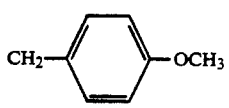 |
| 32 | 1 | 2 | OCH₃ | Cl | H | CH₃ | 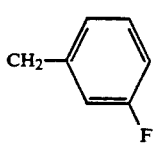 |
| 33 | 1 | 2 | OCH₃ | H | H | CH₃ | 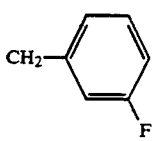 |
| 34 | 1 | 1 | H | H | H | H | CH₂Ph |
| 35 | 1 | 1 | H | H | H | CH₃ | CH₂Ph |
| 36 | 1 | 3 | H | H | H | H | CH₂Ph |
| 37 | 1 | 3 | H | H | H | CH₃ | CH₂Ph |
| 38 | 0 | 2 | H | H | H | H | CH₂Ph |
| 39 | 0 | 2 | H | H | H | CH₃ | CH₂Ph |
| 40 | 0 | 2 | H | H | H | C₂H₅ | CH₂Ph |
| 41 | 0 | 2 | H | H | H | CH₂Ph | CH₂Ph |
| 42 | 0 | 2 | H | H | H | COCH₃ | CH₂Ph |
| 43 | 0 | 2 | H | H | H | COPh | CH₂Ph |
| 44 | 0 | 2 | F | H | H | CH₃ | CH₂Ph |
| 45 | 0 | 2 | F | H | CH₃ | CH₃ | CH₂Ph |
| 46 | 0 | 2 | CH₃ | H | H | CH₃ | CH₂Ph |
| 47 | 0 | 2 | OCH₃ | H | H | CH₃ | CH₂Ph |
| 48 | 0 | 2 | Cl | H | H | CH₃ | CH₂Ph |
| 49 | 0 | 2 | OCH₃ | Cl | H | CH₃ | CH₂Ph |
| 50 | 0 | 2 | F | H | OCH₃ | CH₃ | CH₂Ph |
| 51 | 0 | 2 | Cl | CH₃ | F | CH₃ | CH₂Ph |
| 52 | 0 | 2 | H | H | H | H | 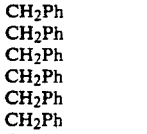 |
| 53 | 0 | 2 | H | H | H | CH₃ | 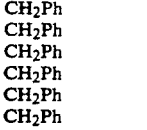 |

-continued
| | | | | | | | |
|---|---|---|---|---|---|---|---|
| 54 | 0 | 2 | H | H | H | CH$_2$Ph | 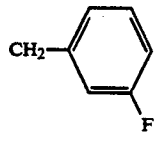 |
| 55 | 0 | 2 | H | H | H | H | 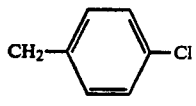 |
| 56 | 0 | 2 | H | H | H | CH$_3$ | 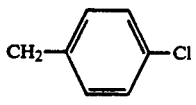 |
| 57 | 0 | 2 | H | H | H | CH$_2$Ph | 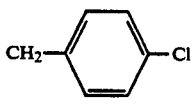 |
| 58 | 0 | 2 | H | H | H | H | 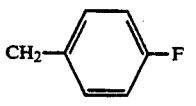 |
| 59 | 0 | 2 | H | H | H | H | 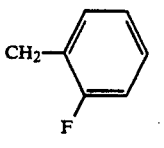 |
| 60 | 0 | 2 | H | H | H | CH$_3$ | 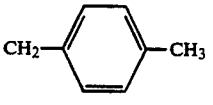 |
| 61 | 0 | 2 | F | H | H | H | 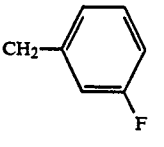 |
| 62 | 0 | 2 | Cl | H | H | H | 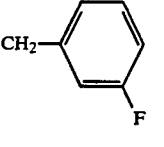 |
| 63 | 0 | 2 | H | H | CH$_3$ | CH$_3$ | 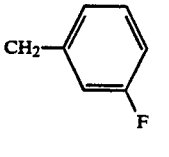 |
| 64 | 0 | 2 | F | H | Cl | CH$_3$ | 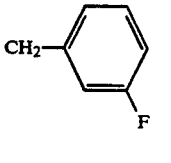 |
| 65 | 0 | 2 | F | H | H | H | 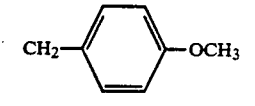 |

-continued

| No | n | m' | X¹ | X² | X³ | R¹ | R² |
|----|---|----|----|----|----|----|----|
| 66 | 0 | 2 | Cl | H | H | H | CH₂-C₆H₄-OCH₃ (4-) |
| 67 | 0 | 2 | H | H | CH₃ | CH₃ | CH₂-C₆H₄-Cl (4-) |
| 68 | 0 | 2 | F | H | Cl | CH₃ | CH₂-C₆H₄-Cl (4-) |
| 69 | 0 | 2 | OCH₃ | OCH₃ | H | CH₃ | CH₂-C₆H₄-F (3-) |
| 70 | 2 | 2 | H | H | H | H | CH₂Ph |
| 71 | 2 | 2 | H | H | H | CH₃ | CH₂Ph |
| 72 | 2 | 2 | H | H | H | C₂H₅ | CH₂Ph |
| 73 | 2 | 2 | F | H | H | H | CH₂Ph |
| 74 | 2 | 2 | F | H | H | CH₃ | CH₂Ph |
| 75 | 2 | 2 | F | H | H | CH₂Ph | CH₂Ph |
| 76 | 2 | 2 | F | H | Cl | CH₃ | CH₂Ph |
| 77 | 2 | 2 | F | H | CH₃ | CH₃ | CH₂Ph |
| 78 | 2 | 2 | CH₃ | H | H | CH₃ | CH₂Ph |
| 79 | 2 | 2 | OCH₃ | H | H | CH₃ | CH₂Ph |
| 80 | 2 | 2 | Cl | H | H | CH₃ | CH₂Ph |
| 81 | 2 | 2 | OCH₃ | Cl | H | CH₃ | CH₂Ph |
| 82 | 2 | 2 | F | H | OCH₃ | CH₃ | CH₂Ph |
| 83 | 2 | 2 | Cl | CH₃ | F | CH₃ | CH₂Ph |
| 84 | 2 | 2 | H | H | H | H | CH₂-C₆H₄-F (3-) |
| 85 | 2 | 2 | H | H | H | CH₃ | CH₂-C₆H₄-F (3-) |
| 86 | 2 | 2 | H | H | H | CH₂Ph | CH₂-C₆H₄-F (3-) |
| 87 | 2 | 2 | H | H | H | H | CH₂-C₆H₄-F (4-) |
| 88 | 1 | 2 | H | H | H | CH₃ | H |
| 89 | 1 | 2 | H | H | H | H | C₂H₅ |

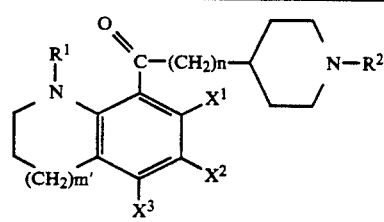

-continued

| No. | m' | n | $X^1$ | $X^2$ | $X^3$ | $R^1$ | $R^2$ |
|---|---|---|---|---|---|---|---|
| 90 | 1 | 2 | H | H | H | H | $CH_2Ph$ |
| 91 | 1 | 2 | H | H | H | $CH_3$ | $CH_2Ph$ |
| 92 | 1 | 2 | H | H | H | $C_2H_5$ | $CH_2Ph$ |
| 93 | 1 | 2 | H | H | H | $CH_2Ph$ | $CH_2Ph$ |
| 94 | 1 | 2 | H | H | H | $COCH_3$ | $CH_2Ph$ |
| 95 | 1 | 2 | H | H | H | COPh | $CH_2Ph$ |
| 96 | 1 | 2 | H | F | H | $CH_3$ | $CH_2Ph$ |
| 97 | 1 | 2 | H | F | $CH_3$ | $CH_3$ | $CH_2Ph$ |
| 98 | 1 | 2 | H | $OCH_3$ | $OCH_3$ | $CH_3$ | $CH_2Ph$ |
| 99 | 1 | 2 | H | F | Cl | $CH_3$ | $CH_2$-(3-F-C$_6$H$_4$) |
| 100 | 1 | 2 | H | F | H | H | $CH_2$-(3-F-C$_6$H$_4$) |
| 101 | 1 | 2 | Cl | F | H | H | $CH_2$-(3-F-C$_6$H$_4$) |
| 102 | 1 | 2 | H | Cl | $CH_3$ | $CH_3$ | $CH_2$-(3-F-C$_6$H$_4$) |
| 103 | 1 | 2 | H | $OCH_3$ | H | $CH_3$ | $CH_2$-(3-F-C$_6$H$_4$) |
| 104 | 1 | 1 | H | H | H | H | $CH_2Ph$ |
| 105 | 1 | 1 | H | H | H | $CH_3$ | $CH_2Ph$ |
| 106 | 1 | 3 | H | H | H | H | $CH_2Ph$ |
| 107 | 1 | 3 | H | H | H | $CH_3$ | $CH_2Ph$ |
| 108 | 0 | 2 | H | H | H | H | $CH_2Ph$ |
| 109 | 0 | 2 | H | H | H | $CH_3$ | $CH_2Ph$ |
| 110 | 0 | 2 | H | H | H | $C_2H_5$ | $CH_2Ph$ |
| 111 | 0 | 2 | H | H | H | $CH_2Ph$ | $CH_2Ph$ |
| 112 | 0 | 2 | H | H | H | $COCH_3$ | $CH_2Ph$ |
| 113 | 0 | 2 | H | H | H | COPh | $CH_2Ph$ |
| 114 | 0 | 2 | H | F | H | $CH_3$ | $CH_2Ph$ |
| 115 | 0 | 2 | H | F | $CH_3$ | $CH_3$ | $CH_2Ph$ |
| 116 | 0 | 2 | H | F | H | $CH_3$ | $CH_2$-(3-F-C$_6$H$_4$) |
| 117 | 2 | 2 | H | $OCH_3$ | H | $CH_3$ | $CH_2Ph$ |
| 118 | 2 | 2 | H | $CH_3$ | H | $CH_3$ | $CH_2Ph$ |
| 119 | 2 | 2 | H | H | H | H | $CH_2$-(3-F-C$_6$H$_4$) |

-continued

| No. | m' | n | X¹ | X² | X³ | R¹ | R² |
|-----|----|----|------|------|------|------|------|
| 120 | 2 | 2 | H | H | H | CH₃ | 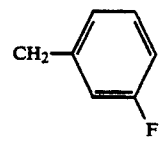 |
| 121 | 2 | 2 | H | H | H | CH₂Ph | 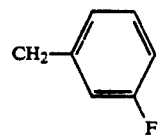 |
| 122 | 2 | 2 | H | F | H | CH₃ | 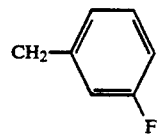 |

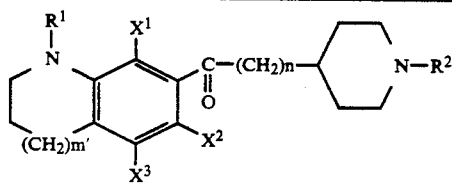

| No. | m' | n | X¹ | X² | X³ | R¹ | R² |
|-----|----|----|------|------|------|--------|--------|
| 123 | 1 | 2 | H | H | H | H | CH₂Ph |
| 124 | 1 | 2 | H | H | H | CH₃ | CH₂Ph |
| 125 | 1 | 2 | H | H | H | C₂H₅ | CH₂Ph |
| 126 | 1 | 2 | H | H | H | CH₂Ph | CH₂Ph |
| 127 | 1 | 2 | H | H | H | COCH₃ | CH₂Ph |
| 128 | 1 | 2 | H | H | H | COPh | CH₂Ph |
| 129 | 1 | 2 | H | H | CH₃ | CH₃ | CH₂Ph |
| 130 | 1 | 2 | H | F | CH₃ | CH₃ | CH₂Ph |
| 131 | 1 | 2 | F | H | F | CH₃ | CH₂Ph |
| 132 | 1 | 2 | H | OCH₃ | OCH₃ | CH₃ | CH₂Ph |
| 133 | 1 | 2 | OCH₃ | H | H | CH₃ | CH₂Ph |
| 134 | 1 | 2 | H | F | F | CH₃ | CH₂Ph |
| 135 | 1 | 2 | OCH₃ | Cl | H | CH₃ | CH₂Ph |
| 136 | 1 | 2 | F | H | OCH₃ | CH₃ | CH₂Ph |
| 137 | 1 | 2 | Cl | CH₃ | F | CH₃ | CH₂Ph |
| 138 | 1 | 2 | H | H | H | CH₃ | CH₂CH₂Ph |
| 139 | 1 | 2 | H | H | H | CH₃ | 3-fluorobenzyl |
| 140 | 1 | 2 | H | H | H | CH₂Ph | 3-fluorobenzyl |
| 141 | 1 | 2 | H | H | H | H | 4-fluorobenzyl |
| 142 | 1 | 2 | H | H | H | H | 2-fluorobenzyl |

-continued
| | | | | | | | |
|---|---|---|---|---|---|---|---|
| 143 | 1 | 2 | H | H | H | CH₃ | 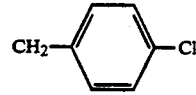 |
| 144 | 1 | 2 | H | H | H | CH₃ |  |
| 145 | 1 | 2 | H | H | H | CH₃ | 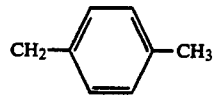 |
| 146 | 1 | 2 | H | H | CH₃ | H | 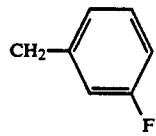 |
| 147 | 1 | 2 | Cl | H | H | H | 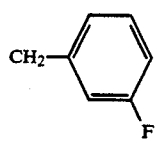 |
| 148 | 1 | 2 | H | H | CH₃ | CH₃ | 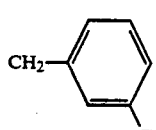 |
| 149 | 1 | 2 | H | F | Cl | CH₃ | 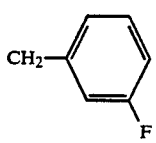 |
| 150 | 1 | 2 | F | H | CH₃ | H | 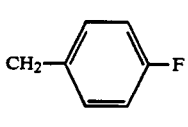 |
| 151 | 1 | 2 | Cl | H | F | H | 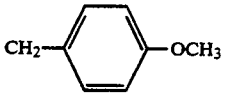 |
| 152 | 1 | 2 | H | H | CH₃ | CH₃ | 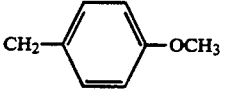 |
| 153 | 1 | 2 | F | H | Cl | CH₃ | 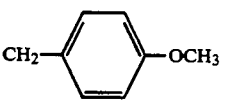 |
| 154 | 1 | 2 | H | H | H | CH₃ | H |
| 155 | 1 | 2 | H | H | H | CH₂Ph | H |
| 156 | 1 | 1 | H | H | H | H | CH₂Ph |
| 157 | 1 | 1 | H | H | H | CH₃ | CH₂Ph |
| 158 | 1 | 3 | H | H | H | H | CH₂Ph |
| 159 | 1 | 3 | H | H | H | CH₃ | CH₂Ph |
| 160 | 0 | 2 | H | H | H | H | CH₂Ph |
| 161 | 0 | 2 | H | H | H | CH₃ | CH₂Ph |
| 162 | 0 | 2 | H | H | H | C₂H₅ | CH₂Ph |

-continued
| | | | | | | | |
|---|---|---|---|---|---|---|---|
| 163 | 0 | 2 | H | H | H | CH₂Ph | CH₂Ph |
| 164 | 0 | 2 | H | H | H | COCH₃ | CH₂Ph |
| 165 | 0 | 2 | H | H | H | COPh | CH₂Ph |
| 166 | 0 | 2 | H | F | H | CH₃ | CH₂Ph |
| 167 | 0 | 2 | H | F | CH₃ | CH₃ | CH₂Ph |
| 168 | 0 | 2 | CH₃ | H | H | CH₃ | CH₂Ph |
| 169 | 0 | 2 | H | OCH₃ | H | CH₃ | CH₂Ph |
| 170 | 0 | 2 | H | Cl | H | CH₃ | CH₂Ph |
| 171 | 0 | 2 | OCH₃ | Cl | H | CH₃ | CH₂Ph |
| 172 | 0 | 2 | H | F | OCH₃ | CH₃ | CH₂Ph |
| 173 | 0 | 2 | Cl | CH₃ | F | CH₃ | CH₂Ph |
| 174 | 0 | 2 | H | H | H | H | 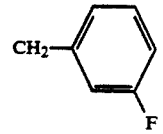 |
| 175 | 0 | 2 | H | H | H | CH₃ | 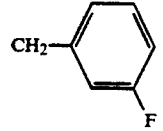 |
| 176 | 0 | 2 | H | H | H | CH₂Ph | 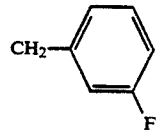 |
| 177 | 0 | 2 | H | H | H | H | 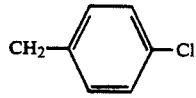 |
| 178 | 0 | 2 | H | H | H | CH₃ |  |
| 179 | 0 | 2 | H | H | H | CH₂Ph | 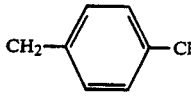 |
| 180 | 0 | 2 | H | H | H | H | 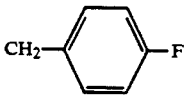 |
| 181 | 0 | 2 | H | H | H | H | 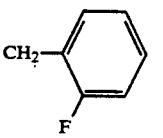 |
| 182 | 0 | 2 | H | H | H | CH₃ | 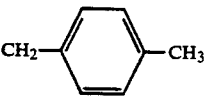 |
| 183 | 0 | 2 | H | F | H | H | 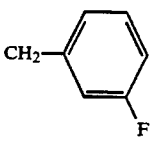 |

| | | | | | | | |
|---|---|---|---|---|---|---|---|
| 184 | 0 | 2 | H | Cl | H | H | 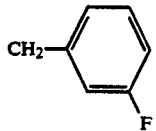 |
| 185 | 0 | 2 | H | F | CH₃ | CH₃ | 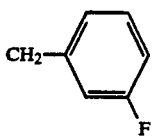 |
| 186 | 0 | 2 | F | F | H | CH₃ | 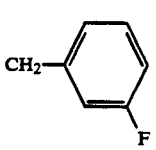 |
| 187 | 0 | 2 | F | H | H | H | 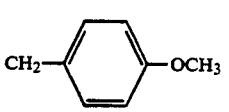 |
| 188 | 0 | 2 | Cl | Cl | H | H | 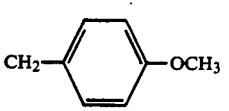 |
| 189 | 0 | 2 | H | F | CH₃ | CH₃ | 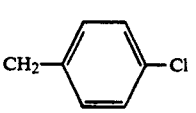 |
| 190 | 0 | 2 | F | F | H | CH₃ | 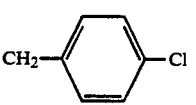 |
| 191 | 0 | 2 | H | H | H | CH₃ | H |
| 192 | 2 | 2 | H | H | H | H | CH₂Ph |
| 193 | 2 | 2 | H | H | H | CH₃ | CH₂Ph |
| 194 | 2 | 2 | H | H | H | C₂H₅ | CH₂Ph |
| 195 | 2 | 2 | H | H | F | H | CH₂Ph |
| 196 | 2 | 2 | H | H | Cl | CH₃ | CH₂Ph |
| 197 | 2 | 2 | F | H | CH₃ | CH₂Ph | CH₂Ph |
| 198 | 2 | 2 | F | H | Cl | CH₃ | CH₂Ph |
| 199 | 2 | 2 | H | H | CH₃ | CH₃ | CH₂Ph |
| 200 | 2 | 2 | CH₃ | H | H | CH₃ | CH₂Ph |
| 201 | 2 | 2 | OCH₃ | H | CH₃ | CH₃ | CH₂Ph |
| 202 | 2 | 2 | Cl | H | CH₃ | CH₃ | CH₂Ph |
| 203 | 2 | 2 | OCH₃ | Cl | CH₃ | CH₃ | CH₂Ph |
| 204 | 2 | 2 | F | H | OCH₃ | CH₃ | CH₂Ph |
| 205 | 2 | 2 | Cl | CH₃ | F | CH₃ | CH₂Ph |
| 206 | 2 | 2 | H | H | H | H | 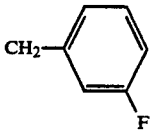 |
| 207 | 2 | 2 | H | H | H | CH₃ | 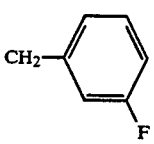 |

-continued

| 208 | 2 | 2 | H | H | H | CH₂Ph | 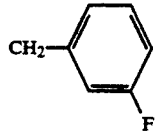 (CH₂-C₆H₄-F, meta) |
| 209 | 2 | 2 | H | H | CH₃ | H | 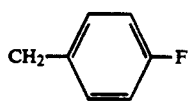 (CH₂-C₆H₄-F, para) |
| 210 | 1 | 2 | H | H | H | CH₃ | CH₃ |
| 211 | 1 | 2 | H | H | H | C₂H₅ | C₂H₅ |

212

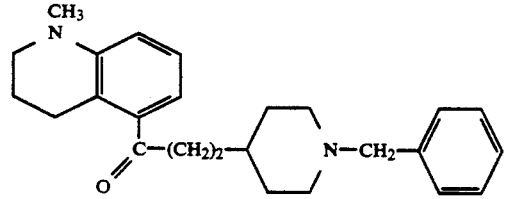

---

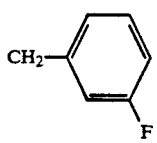

| No. | k | m | n | X¹ | X² | X³ | R¹ | R² |
|-----|---|---|---|----|----|----|----|----|
| 213 | 1 | 2 | 2 | H | H | H | H | CH₂Ph |
| 214 | 1 | 2 | 2 | H | H | H | CH₃ | CH₂Ph |
| 215 | 1 | 2 | 2 | H | H | H | C₂H₅ | CH₂Ph |
| 216 | 1 | 2 | 2 | H | H | H | CH₂Ph | CH₂Ph |
| 217 | 1 | 2 | 2 | H | H | H | COCH₃ | CH₂Ph |
| 218 | 1 | 2 | 2 | H | H | H | COPh | CH₂Ph |
| 219 | 1 | 2 | 2 | H | F | H | CH₃ | CH₂Ph |
| 220 | 1 | 2 | 2 | H | F | CH₃ | CH₃ | CH₂Ph |
| 221 | 1 | 2 | 2 | CH₃ | Cl | H | CH₃ | CH₂Ph |
| 222 | 1 | 2 | 2 | H | OCH₃ | H | CH₃ | CH₂Ph |
| 223 | 1 | 2 | 2 | OCH₃ | F | H | CH₃ | CH₂Ph |
| 224 | 1 | 2 | 2 | F | F | H | CH₃ | CH₂Ph |
| 225 | 1 | 2 | 2 | Cl | Cl | H | CH₃ | CH₂Ph |
| 226 | 1 | 2 | 2 | F | F | OCH₃ | CH₃ | CH₂Ph |
| 227 | 1 | 2 | 2 | Cl | CH₃ | F | CH₃ | CH₂Ph |
| 228 | 1 | 2 | 2 | H | H | H | CH₃ | CH₂CH₂Ph |
| 229 | 1 | 2 | 2 | H | H | H | CH₃ | 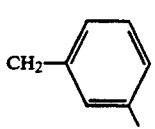 (CH₂-C₆H₄-F, meta) |
| 230 | 1 | 2 | 2 | H | H | H | CH₂Ph | 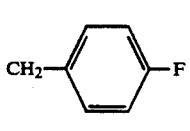 (CH₂-C₆H₄-F, meta) |
| 231 | 1 | 2 | 2 | H | H | H | H | (CH₂-C₆H₄-F, para) |
| 232 | 1 | 2 | 2 | H | H | H | H | 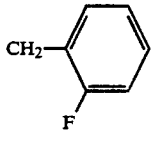 (CH₂-C₆H₄-F, ortho) |

-continued
| | | | | | | | | |
|---|---|---|---|---|---|---|---|---|
| 233 | 1 | 2 | 2 | H | H | H | CH₃ | 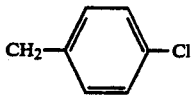 |
| 234 | 1 | 2 | 2 | H | H | H | CH₃ | 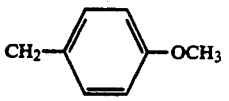 |
| 235 | 1 | 2 | 2 | H | H | H | CH₃ |  |
| 236 | 1 | 2 | 2 | CF₃ | F | H | H | 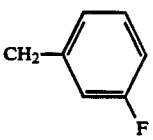 |
| 237 | 1 | 2 | 2 | Cl | Cl | H | H | 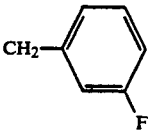 |
| 238 | 1 | 2 | 2 | H | F | CH₃ | CH₃ | 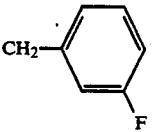 |
| 239 | 1 | 2 | 2 | H | F | Cl | CH₃ | 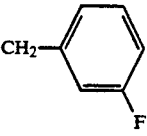 |
| 240 | 1 | 2 | 2 | CH₃ | H | H | H | 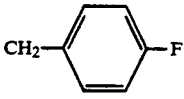 |
| 241 | 1 | 2 | 2 | Cl | Cl | H | H | 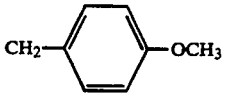 |
| 242 | 1 | 2 | 2 | H | F | CH₃ | CH₃ | 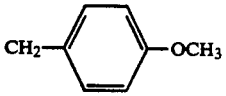 |
| 243 | 1 | 2 | 2 | F | OCH₃ | Cl | CH₃ | 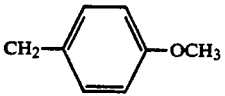 |
| 244 | 1 | 2 | 2 | H | H | H | CH₂Ph | H |
| 245 | 1 | 2 | 2 | H | H | H | CH₃ | H |
| 246 | 1 | 2 | 1 | H | H | H | H | CH₂Ph |
| 247 | 1 | 2 | 1 | H | H | H | CH₃ | CH₂Ph |
| 248 | 1 | 2 | 3 | H | H | H | H | CH₂Ph |
| 249 | 1 | 2 | 3 | H | H | H | CH₃ | CH₂Ph |
| 250 | 1 | 3 | 2 | H | H | H | H | CH₂Ph |
| 251 | 1 | 3 | 2 | H | H | H | CH₃ | CH₂Ph |

-continued
| | | | | | | | | |
|---|---|---|---|---|---|---|---|---|
| 252 | 1 | 3 | 2 | H | H | H | C$_2$H$_5$ | CH$_2$Ph |
| 253 | 1 | 3 | 2 | H | H | H | CH$_2$Ph | CH$_2$Ph |
| 254 | 1 | 3 | 2 | H | H | H | COCH$_3$ | CH$_2$Ph |
| 255 | 1 | 3 | 2 | H | H | H | COPh | CH$_2$Ph |
| 256 | 1 | 3 | 2 | CH$_3$ | H | H | CH$_3$ | CH$_2$Ph |
| 257 | 1 | 3 | 2 | CH$_3$ | H | CH$_3$ | CH$_3$ | CH$_2$Ph |
| 258 | 1 | 3 | 2 | F | F | H | CH$_3$ | CH$_2$Ph |
| 259 | 1 | 3 | 2 | OCH$_3$ | H | H | CH$_3$ | CH$_2$Ph |
| 260 | 1 | 3 | 2 | Cl | H | H | CH$_3$ | CH$_2$Ph |
| 261 | 1 | 3 | 2 | OCH$_3$ | Cl | H | CH$_3$ | CH$_2$Ph |
| 262 | 1 | 3 | 2 | F | H | OCH$_3$ | CH$_3$ | CH$_2$Ph |
| 263 | 1 | 3 | 2 | Cl | CH$_3$ | F | CH$_3$ | CH$_2$Ph |
| 264 | 1 | 3 | 2 | H | H | H | H | 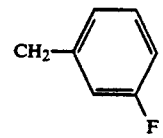 |
| 265 | 1 | 3 | 2 | H | H | H | CH$_3$ | 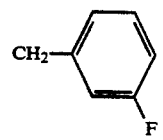 |
| 266 | 1 | 3 | 2 | H | H | H | CH$_2$Ph | 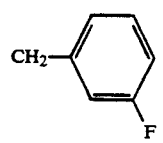 |
| 267 | 1 | 3 | 2 | H | H | H | H | 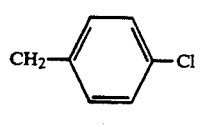 |
| 268 | 1 | 3 | 2 | H | H | H | CH$_3$ | 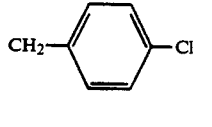 |
| 269 | 1 | 3 | 2 | H | H | H | CH$_2$Ph | 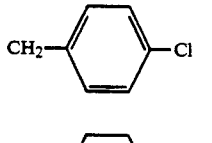 |
| 270 | 1 | 3 | 2 | H | H | H | H | 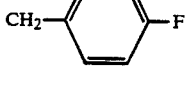 |
| 271 | 1 | 3 | 2 | H | H | H | H | 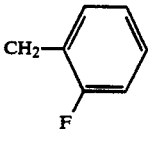 |
| 272 | 1 | 3 | 2 | H | H | H | CH$_3$ | 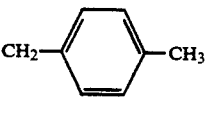 |
| 273 | 1 | 3 | 2 | F | H | H | H | 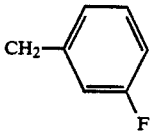 |

-continued
| | | | | | | | | |
|---|---|---|---|---|---|---|---|---|
| 274 | 1 | 3 | 2 | Cl | H | H | H | 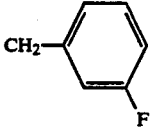 |
| 275 | 1 | 3 | 2 | CH$_3$ | H | OH | CH$_3$ | 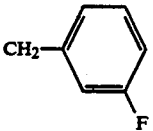 |
| 276 | 1 | 3 | 2 | F | H | Cl | CH$_3$ | 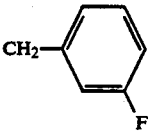 |
| 277 | 1 | 3 | 2 | F | H | H | H | 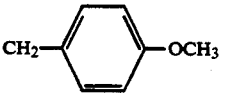 |
| 278 | 1 | 3 | 2 | Cl | H | H | H | 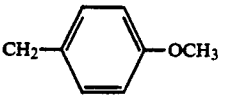 |
| 279 | 1 | 3 | 2 | CH$_3$ | H | H | CH$_3$ | 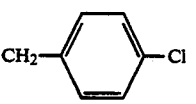 |
| 280 | 1 | 3 | 2 | F | H | Cl | CH$_3$ | 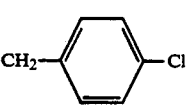 |
| 281 | 1 | 3 | 2 | CH$_3$ | OCH$_3$ | H | CH$_3$ | H |
| 282 | 1 | 1 | 2 | H | H | H | H | CH$_2$Ph |
| 283 | 1 | 1 | 2 | H | H | H | CH$_3$ | CH$_2$Ph |
| 284 | 1 | 1 | 2 | H | H | H | C$_2$H$_5$ | CH$_2$Ph |
| 285 | 2 | 2 | 2 | H | H | H | H | CH$_2$Ph |
| 286 | 2 | 2 | 2 | H | H | H | CH$_3$ | CH$_2$Ph |
| 287 | 2 | 2 | 2 | H | H | H | CH$_2$Ph | CH$_2$Ph |
| 288 | 2 | 2 | 2 | F | H | Cl | CH$_3$ | CH$_2$Ph |
| 289 | 2 | 2 | 2 | F | H | CH$_3$ | CH$_3$ | CH$_2$Ph |
| 290 | 2 | 2 | 2 | CH$_3$ | H | H | CH$_3$ | CH$_2$Ph |
| 291 | 2 | 2 | 2 | OCH$_3$ | H | H | CH$_3$ | CH$_2$Ph |
| 292 | 2 | 2 | 2 | Cl | H | H | CH$_3$ | CH$_2$Ph |
| 293 | 2 | 2 | 2 | OCH$_3$ | Cl | H | CH$_3$ | CH$_2$Ph |
| 294 | 2 | 2 | 2 | F | H | OCH$_3$ | CH$_3$ | CH$_2$Ph |
| 295 | 2 | 2 | 2 | Cl | CH$_3$ | F | CH$_3$ | CH$_2$Ph |
| 296 | 2 | 2 | 2 | H | H | H | H | 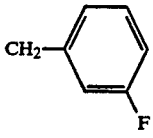 |
| 297 | 2 | 2 | 2 | H | H | H | CH$_3$ | 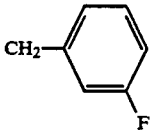 |

-continued

| No. | k | m | n | X¹ | X² | X³ | R¹ | R² |
|---|---|---|---|---|---|---|---|---|
| 298 | 2 | 2 | 2 | H | H | H | CH₂Ph | 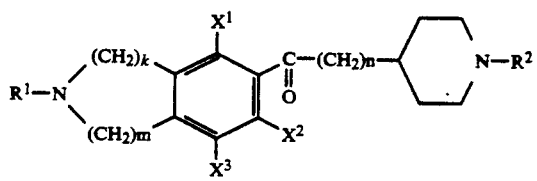 |
| 299 | 2 | 2 | 2 | H | H | H | H | H |
| 300 | 1 | 2 | 2 | H | H | H | CH₃ | H |
| 301 | 1 | 2 | 2 | H | H | H | H | C₂H₅ |

$$R^1-N\begin{matrix}(CH_2)_k\\(CH_2)_m\end{matrix}\begin{matrix}X^1\\X^3\end{matrix}\overset{O}{\underset{\|}{C}}-(CH_2)_n-\begin{matrix}\\ \end{matrix}N-R^2$$

| No. | k | m | n | X¹ | X² | X³ | R¹ | R² |
|---|---|---|---|---|---|---|---|---|
| 302 | 1 | 2 | 2 | H | H | H | H | CH₂Ph |
| 303 | 1 | 2 | 2 | H | H | H | CH₃ | CH₂Ph |
| 304 | 1 | 2 | 2 | H | H | H | C₂H₅ | CH₂Ph |
| 305 | 1 | 2 | 2 | H | H | H | CH₂Ph | CH₂Ph |
| 306 | 1 | 2 | 2 | H | H | H | COCH₃ | CH₂Ph |
| 307 | 1 | 2 | 2 | H | H | H | COPh | CH₂Ph |
| 308 | 1 | 2 | 2 | H | H | CH₃ | CH₃ | CH₂Ph |
| 309 | 1 | 2 | 2 | F | H | CH₃ | CH₃ | CH₂Ph |
| 310 | 1 | 2 | 2 | H | H | F | CH₃ | CH₂Ph |
| 311 | 1 | 2 | 2 | H | OCH₃ | OCH₃ | CH₃ | CH₂Ph |
| 312 | 1 | 2 | 2 | OCH₃ | H | CH₃ | CH₃ | CH₂Ph |
| 313 | 1 | 2 | 2 | H | H | Cl | CH₃ | CH₂Ph |
| 314 | 1 | 2 | 2 | H | Cl | CH₃ | CH₃ | CH₂Ph |
| 315 | 1 | 2 | 2 | H | F | OCH₃ | CH₃ | CH₂Ph |
| 316 | 1 | 2 | 2 | Cl | CH₃ | F | CH₃ | CH₂Ph |
| 317 | 1 | 2 | 2 | H | H | H | CH₃ | CH₂CH₂Ph |
| 318 | 1 | 2 | 2 | H | H | H | CH₃ | 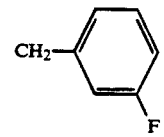 |
| 319 | 1 | 2 | 2 | H | H | H | CH₂Ph | 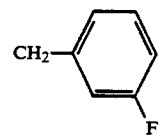 |
| 320 | 1 | 2 | 2 | H | H | H | H | 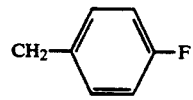 |
| 321 | 1 | 2 | 2 | H | H | H | H | 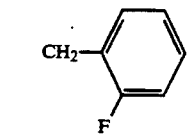 |
| 322 | 1 | 2 | 2 | H | H | H | CH₃ | 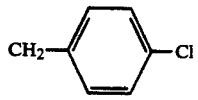 |
| 323 | 1 | 2 | 2 | H | H | H | CH₃ | 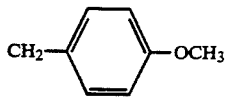 |

-continued

| | | | | | | | | |
|---|---|---|---|---|---|---|---|---|
| 324 | 1 | 2 | 2 | H | H | H | CH₃ | CH₂–C₆H₄–CH₃ (para) |
| 325 | 1 | 2 | 2 | H | H | CF₃ | H | CH₂–C₆H₄–F (meta) |
| 326 | 1 | 2 | 2 | H | H | Cl | H | CH₂–C₆H₄–F (meta) |
| 327 | 1 | 2 | 2 | H | H | CH₃ | CH₃ | CH₂–C₆H₄–F (meta) |
| 328 | 1 | 2 | 2 | H | F | Cl | CH₃ | CH₂–C₆H₄–F (meta) |
| 329 | 1 | 2 | 2 | F | H | CH₃ | H | CH₂–C₆H₄–F (para) |
| 330 | 1 | 2 | 2 | Cl | H | CH₃ | H | CH₂–C₆H₄–OCH₃ (para) |
| 331 | 1 | 2 | 2 | H | H | CH₃ | CH₃ | CH₂–C₆H₄–OCH₃ (para) |
| 332 | 1 | 2 | 2 | H | F | Cl | CH₃ | CH₂–C₆H₄–OCH₃ (para) |
| 333 | 1 | 2 | 2 | H | Cl | CH₃ | CH₃ | CH₂–C₆H₄–F (meta) |
| 334 | 1 | 2 | 2 | NO₂ | OCH₃ | OCH₃ | CH₃ | CH₂–C₆H₄–F (meta) |
| 335 | 1 | 2 | 1 | H | H | H | H | CH₂Ph |
| 336 | 1 | 2 | 1 | H | H | H | CH₃ | CH₂Ph |
| 337 | 1 | 2 | 3 | H | H | H | H | CH₂Ph |
| 338 | 1 | 3 | 3 | H | H | H | CH₃ | CH₂Ph |
| 339 | 1 | 3 | 2 | H | H | H | H | CH₂Ph |
| 340 | 1 | 3 | 2 | H | H | H | CH₃ | CH₂Ph |

| | | | | | | | | |
|---|---|---|---|---|---|---|---|---|
| 341 | 1 | 3 | 2 | H | H | H | C₂H₅ | CH₂Ph |
| 342 | 1 | 3 | 2 | H | H | H | CH₂Ph | CH₂Ph |
| 343 | 1 | 3 | 2 | H | H | H | COCH₃ | CH₂Ph |
| 344 | 1 | 3 | 2 | H | H | H | COPh | CH₂Ph |
| 345 | 1 | 3 | 2 | H | H | CH₃ | CH₃ | CH₂Ph |
| 346 | 1 | 3 | 2 | H | F | CH₃ | CH₃ | CH₂Ph |
| 347 | 1 | 3 | 2 | F | H | CH₃ | CH₃ | CH₂Ph |
| 348 | 1 | 3 | 2 | H | H | OCH₃ | CH₃ | CH₂Ph |
| 349 | 1 | 3 | 2 | H | H | Cl | CH₃ | CH₂Ph |
| 350 | 1 | 3 | 2 | H | Cl | F | CH₃ | CH₂Ph |
| 351 | 1 | 3 | 2 | H | CH₃ | OCH₃ | CH₃ | CH₂Ph |
| 352 | 1 | 3 | 2 | Cl | CH₃ | F | CH₃ | CH₂Ph |
| 353 | 1 | 3 | 2 | H | H | H | H | 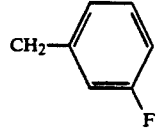 |
| 354 | 1 | 3 | 2 | H | H | H | CH₃ | 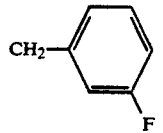 |
| 355 | 1 | 3 | 2 | H | H | H | CH₂Ph | 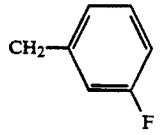 |
| 356 | 1 | 3 | 2 | H | H | H | H | 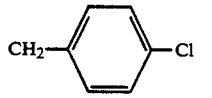 |
| 357 | 1 | 3 | 2 | H | H | H | CH₃ | 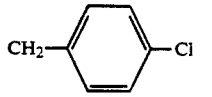 |
| 358 | 1 | 3 | 2 | H | H | H | CH₂Ph | 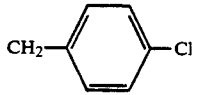 |
| 359 | 1 | 3 | 2 | H | H | H | H | 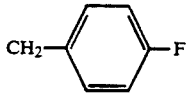 |
| 360 | 1 | 3 | 2 | H | H | H | H |  |
| 361 | 1 | 3 | 2 | H | H | H | CH₃ | 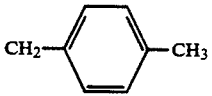 |
| 362 | 1 | 3 | 2 | H | H | F | H | 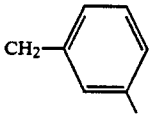 |

-continued
| | | | | | | | | |
|---|---|---|---|---|---|---|---|---|
| 363 | 1 | 3 | 2 | H | H | Cl | H | 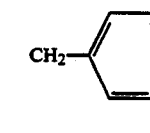 |
| 364 | 1 | 3 | 2 | H | H | CH$_3$ | CH$_3$ | 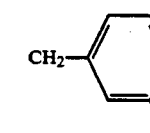 |
| 365 | 1 | 3 | 2 | H | H | Cl | CH$_3$ | 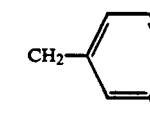 |
| 366 | 1 | 3 | 2 | H | H | OCH$_3$ | H | 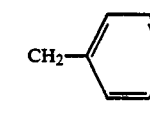 |
| 367 | 1 | 3 | 2 | SCH$_3$ | H | CH$_3$ | H | 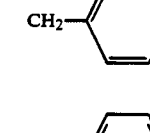 |
| 368 | 1 | 3 | 2 | H | CH$_3$ | CH$_3$ | CH$_3$ | 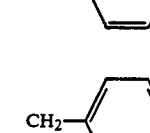 |
| 369 | 1 | 3 | 2 | H | H | Cl | CH$_3$ | 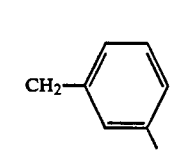 |
| 370 | 1 | 3 | 2 | H | OCH$_3$ | OCH$_3$ | CH$_3$ | 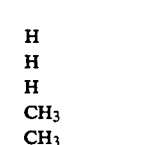 |
| 371 | 1 | 2 | 2 | H | H | H | H | H |
| 372 | 1 | 2 | 2 | H | H | H | CH$_3$ | H |
| 373 | 1 | 2 | 2 | H | H | H | C$_2$H$_5$ | H |
| 374 | 1 | 2 | 2 | H | H | H | H | CH$_3$ |
| 375 | 1 | 2 | 2 | H | H | H | CH$_3$ | CH$_3$ |
| 376 | 1 | 2 | 2 | H | H | H | CH$_2$Ph | CH$_3$ |
| 377 | 1 | 3 | 2 | H | H | H | CH$_3$ | H |
| 378 | 1 | 3 | 2 | H | H | CH$_3$ | CH$_3$ | H |
| 379 | 1 | 3 | 2 | H | H | F | CH$_3$ | H |
| 380 | 1 | 3 | 2 | OCH$_3$ | H | CH$_3$ | CH$_3$ | CH$_3$ |
| 381 | 1 | 3 | 2 | H | H | OCH$_3$ | CH$_3$ | CH$_3$ |
| 382 | | | | | | | | |
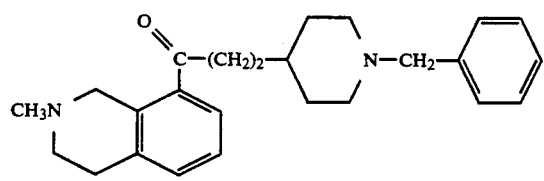

-continued
383 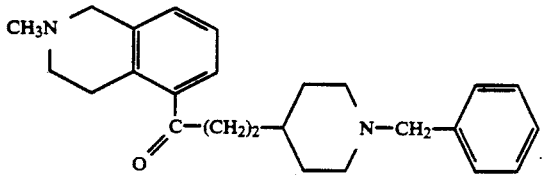
384 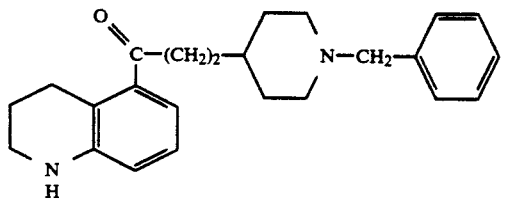
385 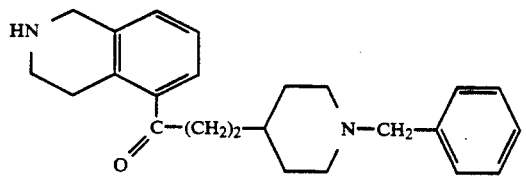
386 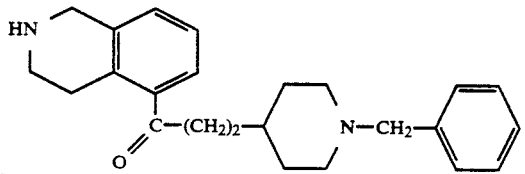
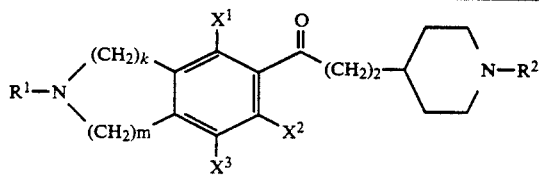
| No. | k | m | X¹ | X² | X³ | R¹ | R² |
|-----|---|---|-----|-----|-----|-----|-----|
| 387 | 0 | 5 | H | H | H | H | CH$_2$Ph |
| 388 | 0 | 5 | H | H | H | CH$_3$ | CH$_2$Ph |
| 389 | 0 | 5 | H | H | H | C$_2$H$_5$ | CH$_2$Ph |
| 390 | 0 | 5 | H | H | H | CH$_2$Ph | CH$_2$Ph |
| 391 | 0 | 5 | H | H | H | COCH$_3$ | CH$_2$Ph |
| 392 | 0 | 5 | H | H | H | COPh | CH$_2$Ph |
| 393 | 0 | 5 | H | H | H | H | H |
| 394 | 0 | 5 | H | H | H | H | CH$_2$-C$_6$H$_4$-Cl |
| 395 | 0 | 5 | CH$_3$ | H | Cl | CH$_3$ | CH$_2$-C$_6$H$_4$-CH$_3$ |
| 396 | 0 | 5 | F | H | OCH$_3$ | CH$_3$ | CH$_2$Ph |
| 397 | 1 | 4 | H | H | H | H | CH$_2$Ph |
| 398 | 1 | 4 | H | H | H | CH$_3$ | CH$_2$Ph |
| 399 | 1 | 4 | H | H | H | C$_2$H$_5$ | CH$_2$Ph |
| 400 | 1 | 4 | H | H | H | CH$_2$Ph | CH$_2$Ph |
| 401 | 1 | 4 | H | H | H | COCH$_3$ | CH$_2$Ph |
| 402 | 1 | 4 | H | H | H | COPh | CH$_2$Ph |

-continued

| | | | | | | |
|---|---|---|---|---|---|---|
| 403 | 1 | 4 | CH₃ | H | CH₃ | H |

| | | | | | | |
|---|---|---|---|---|---|---|
| 404 | 1 | 4 | Cl | H | H | H | CH₂Ph |
| 405 | 1 | 4 | CH₃ | H | F | CH₃ |

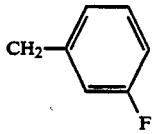

| | | | | | | |
|---|---|---|---|---|---|---|
| 406 | 1 | 4 | F | H | OCH₃ | CH₃ | CH₂Ph |
| 407 | 2 | 3 | H | H | H | H | CH₂Ph |
| 408 | 2 | 3 | H | H | H | CH₃ | CH₂Ph |
| 409 | 2 | 3 | H | H | H | C₂H₅ | CH₂Ph |
| 410 | 2 | 3 | H | H | H | CH₂Ph | CH₂Ph |
| 411 | 2 | 3 | H | H | H | COCH₃ | CH₂Ph |
| 412 | 2 | 3 | H | H | H | COPh | CH₂Ph |
| 413 | 2 | 3 | CH₃ | H | CH₃ | H |

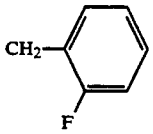

| | | | | | | |
|---|---|---|---|---|---|---|
| 414 | 2 | 3 | Cl | H | H | H | CH₂Ph |
| 415 | 2 | 3 | CH₃ | H | F | CH₃ |

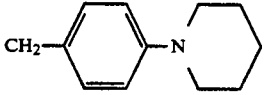

| | | | | | | |
|---|---|---|---|---|---|---|
| 416 | 2 | 3 | F | H | OCH₃ | CH₃ | CH₂Ph |
| 417 | 3 | 2 | H | H | H | H | CH₂Ph |
| 418 | 3 | 2 | H | H | H | CH₃ | CH₂Ph |
| 419 | 3 | 2 | H | H | H | C₂H₅ | CH₂Ph |
| 420 | 3 | 2 | H | H | H | CH₂Ph | CH₂Ph |
| 421 | 3 | 2 | H | H | H | COCH₃ | CH₂Ph |
| 422 | 3 | 2 | H | H | H | COPh | CH₂Ph |
| 423 | 3 | 2 | CH₃ | H | CH₃ | H |

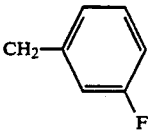

| | | | | | | |
|---|---|---|---|---|---|---|
| 424 | 3 | 2 | Cl | H | H | H | CH₂Ph |
| 425 | 3 | 2 | CH₃ | H | F | CH₃ |

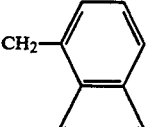

| | | | | | | |
|---|---|---|---|---|---|---|
| 426 | 3 | 2 | F | H | OCH₃ | CH₃ | CH₂Ph |
| 427 | 0 | 6 | H | H | H | H | CH₂Ph |
| 428 | 0 | 6 | H | H | H | CH₃ | CH₂Ph |
| 429 | 0 | 6 | H | H | H | C₂H₅ | CH₂Ph |
| 430 | 0 | 6 | H | H | H | CH₂Ph | CH₂Ph |
| 431 | 0 | 6 | H | H | H | COCH₃ | CH₂Ph |
| 432 | 0 | 6 | H | H | H | COPh | CH₂Ph |
| 433 | 0 | 6 | H | H | Cl | H |

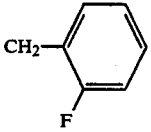

-continued

| No. | | | | | | | |
|---|---|---|---|---|---|---|---|
| 434 | 0 | 6 | H | H | H | H | CH$_2$-C$_6$H$_4$-Cl (4-Cl) |
| 435 | 0 | 6 | CH$_3$ | H | F | CH$_3$ | CH$_2$-(1-naphthyl) |
| 436 | 0 | 6 | F | H | OCH$_3$ | CH$_3$ | CH$_2$Ph |
| 437 | 1 | 5 | H | H | H | H | CH$_2$Ph |
| 438 | 1 | 5 | H | H | H | CH$_3$ | CH$_2$Ph |
| 439 | 1 | 5 | H | H | H | C$_2$H$_5$ | CH$_2$Ph |
| 440 | 1 | 5 | H | H | H | CH$_2$Ph | CH$_2$Ph |
| 441 | 1 | 5 | H | H | H | COCH$_3$ | CH$_2$Ph |
| 442 | 1 | 5 | H | H | H | COPh | CH$_2$Ph |
| 443 | 1 | 5 | H | H | Cl | H | CH$_2$-C$_6$H$_4$-NO$_2$ (3-NO$_2$) |
| 444 | 1 | 5 | H | H | CH$_3$ | H | CH$_2$Ph |
| 445 | 1 | 5 | CH$_3$ | H | F | CH$_3$ | CH$_2$-C$_6$H$_4$-SCH$_3$ (3-SCH$_3$) |
| 446 | 1 | 5 | F | H | OCH$_3$ | CH$_3$ | CH$_2$Ph |
| 457 | 2 | 4 | H | H | H | H | CH$_2$Ph |
| 458 | 2 | 4 | H | H | H | CH$_3$ | CH$_2$Ph |
| 459 | 2 | 4 | H | H | H | C$_2$H$_5$ | CH$_2$Ph |
| 460 | 2 | 4 | H | H | H | CH$_2$Ph | CH$_2$Ph |
| 461 | 2 | 4 | H | H | H | COCH$_3$ | CH$_2$Ph |
| 462 | 2 | 4 | H | H | H | COPh | CH$_2$Ph |
| 463 | 2 | 4 | CH$_3$ | H | CH$_3$ | H | CH$_2$-C$_6$H$_4$-CN (3-CN) |
| 464 | 2 | 4 | Cl | H | H | H | CH$_2$Ph |
| 465 | 2 | 4 | CH$_3$ | H | F | CH$_3$ | CH$_2$-C$_6$H$_4$-CF$_3$ (3-CF$_3$) |
| 466 | 2 | 4 | F | H | OCH$_3$ | CH$_3$ | CH$_2$Ph |
| 467 | 3 | 3 | H | H | H | H | CH$_2$Ph |
| 468 | 3 | 3 | H | H | H | CH$_3$ | CH$_2$Ph |
| 469 | 3 | 3 | H | H | H | C$_2$H$_5$ | CH$_2$Ph |
| 470 | 3 | 3 | H | H | H | CH$_2$Ph | CH$_2$Ph |
| 471 | 3 | 3 | H | H | H | COCH$_3$ | CH$_2$Ph |
| 472 | 3 | 3 | H | H | H | COPh | CH$_2$Ph |

-continued

| No. | k | m | | | | | |
|---|---|---|---|---|---|---|---|
| 473 | 3 | 3 | H | H | H | H | 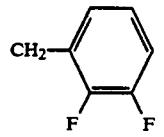 2,3-difluorobenzyl (CH₂-C₆H₃-2,3-F₂) |
| 474 | 3 | 3 | H | H | H | H | 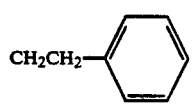 CH₂CH₂Ph |
| 475 | 3 | 3 | CH₃ | H | F | CH₃ | 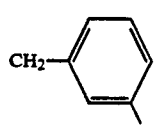 3-fluorobenzyl |
| 476 | 3 | 3 | F | H | OCH₃ | CH₃ | CH₂Ph |

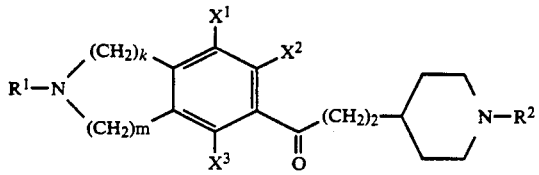

| No. | k | m | X¹ | X² | X³ | R¹ | R² |
|---|---|---|---|---|---|---|---|
| 477 | 0 | 5 | H | H | H | H | CH₂Ph |
| 478 | 0 | 5 | H | H | H | CH₃ | CH₂Ph |
| 479 | 0 | 5 | H | H | H | C₂H₅ | CH₂Ph |
| 480 | 0 | 5 | H | H | H | CH₂Ph | CH₂Ph |
| 481 | 0 | 5 | H | H | H | COCH₃ | CH₂Ph |
| 482 | 0 | 5 | H | H | H | COPh | CH₂Ph |
| 483 | 0 | 5 | H | H | H | H | 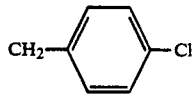 4-chlorobenzyl |
| 484 | 0 | 5 | H | H | H | H | 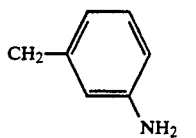 3-aminobenzyl |
| 485 | 0 | 5 | CH₃ | H | Cl | CH₃ | 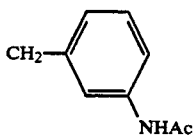 3-acetamidobenzyl |
| 486 | 0 | 5 | F | H | OCH₃ | CH₃ | CH₂Ph |
| 487 | 1 | 4 | H | H | H | H | CH₂Ph |
| 488 | 1 | 4 | H | H | H | CH₃ | CH₂Ph |
| 489 | 1 | 4 | H | H | H | C₂H₅ | CH₂Ph |
| 490 | 1 | 4 | H | H | H | CH₂Ph | CH₂Ph |
| 501 | 1 | 4 | H | H | H | COCH₃ | CH₂Ph |
| 502 | 1 | 4 | H | H | H | COPh | CH₂Ph |
| 503 | 1 | 4 | CH₃ | H | CH₃ | H | 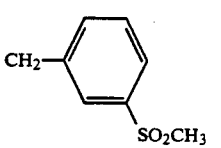 3-(methylsulfonyl)benzyl |
| 504 | 1 | 4 | Cl | H | H | H | CH₂Ph |

-continued

| | | | | | | | |
|---|---|---|---|---|---|---|---|
| 505 | 1 | 4 | CH$_3$ | H | F | CH$_3$ | CH$_2$-(3-NHCOCF$_3$-C$_6$H$_4$) |
| 506 | 1 | 4 | F | H | OCH$_3$ | CH$_3$ | CH$_2$Ph |
| 507 | 0 | 6 | H | H | H | H | CH$_2$Ph |
| 508 | 0 | 6 | H | H | H | CH$_3$ | CH$_2$Ph |
| 509 | 0 | 6 | H | H | H | C$_2$H$_5$ | CH$_2$Ph |
| 510 | 0 | 6 | H | H | H | CH$_2$Ph | CH$_2$Ph |
| 511 | 0 | 6 | H | H | H | COCH$_3$ | CH$_2$Ph |
| 512 | 0 | 6 | H | H | H | COPh | CH$_2$Ph |
| 513 | 0 | 6 | H | H | Cl | H | CH$_2$-(3-COCH$_3$-C$_6$H$_4$) |
| 514 | 0 | 6 | H | H | H | H | CH$_2$-(3-OH-C$_6$H$_4$) |
| 515 | 0 | 6 | CH$_3$ | H | F | CH$_3$ | CH$_2$-(3-COPh-C$_6$H$_4$) |
| 516 | 0 | 6 | F | H | OCH$_3$ | CH$_3$ | CH$_2$Ph |
| 517 | 1 | 5 | H | H | H | H | CH$_2$Ph |
| 518 | 1 | 5 | H | H | H | CH$_3$ | CH$_2$Ph |
| 519 | 1 | 5 | H | H | H | C$_2$H$_5$ | CH$_2$Ph |
| 520 | 1 | 5 | H | H | H | CH$_2$Ph | CH$_2$Ph |
| 521 | 1 | 5 | H | H | H | COCH$_3$ | CH$_2$Ph |
| 522 | 1 | 5 | H | H | H | COPh | CH$_2$Ph |
| 523 | 1 | 5 | H | H | Cl | H | CH$_2$-(3-C$_2$H$_5$-C$_6$H$_4$) |
| 524 | 1 | 5 | H | H | CH$_3$ | H | CH$_2$Ph |
| 525 | 1 | 5 | CH$_3$ | H | F | CH$_3$ | CH$_2$-(3-Ph-C$_6$H$_4$) |
| 526 | 1 | 5 | F | H | OCH$_3$ | CH$_3$ | CH$_2$Ph |
| 527 | 2 | 4 | H | H | H | H | CH$_2$Ph |
| 528 | 2 | 4 | H | H | H | CH$_3$ | CH$_2$Ph |
| 529 | 2 | 4 | H | H | H | C$_2$H$_5$ | CH$_2$Ph |
| 530 | 2 | 4 | H | H | H | CH$_2$Ph | CH$_2$Ph |
| 531 | 2 | 4 | H | H | H | COCH$_3$ | CH$_2$Ph |
| 532 | 2 | 4 | H | H | H | COPh | CH$_2$Ph |
| 533 | 2 | 4 | CH$_3$ | H | CH$_3$ | H | CH$_2$-(3-CO$_2$H-C$_6$H$_4$) |
| 534 | 2 | 4 | Cl | H | H | H | CH$_2$Ph |

-continued

| | | | | | | |
|---|---|---|---|---|---|---|
| 535 | 2 | 4 | CH₃ | H | F | CH₃ |

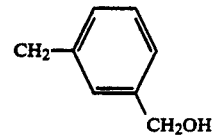

| 536 | 2 | 4 | F | H | OCH₃ | CH₃ | CH₂Ph |

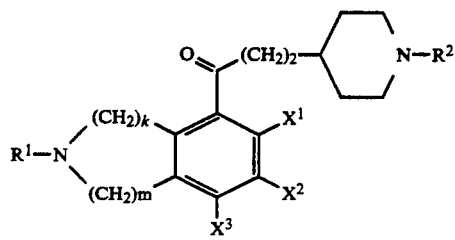

| No. | k | m | X¹ | X² | X³ | R¹ | R² |
|---|---|---|---|---|---|---|---|
| 537 | 1 | 1 | H | H | H | H | CH₂Ph |
| 538 | 1 | 1 | H | H | H | CH₃ | CH₂Ph |
| 539 | 1 | 1 | H | H | CH₃ | H | CH₂Ph |
| 540 | 1 | 1 | H | H | Cl | H | CH₂Ph |
| 541 | 1 | 1 | H | H | H | COCH₃ | CH₂Ph |
| 542 | 1 | 1 | H | H | OCH₃ | CH₃ | CH₂Ph |
| 543 | 1 | 1 | H | H | Cl | H | H |
| 544 | 1 | 2 | H | H | Cl | H | CH₂Ph |
| 545 | 1 | 2 | H | H | CH₃ | H | CH₂Ph |
| 546 | 1 | 2 | CH₃ | H | F | CH₃ | CH₂Ph |
| 547 | 1 | 2 | F | H | OCH₃ | C₂H₅ | CH₂Ph |
| 548 | 1 | 2 | H | H | CH₃ | H | H |
| 549 | 2 | 1 | H | H | Cl | H | CH₂Ph |
| 550 | 2 | 1 | H | H | CH₃ | H | CH₂Ph |
| 551 | 2 | 1 | CH₃ | H | F | CH₃ | CH₂Ph |
| 552 | 2 | 1 | F | H | COCH₃ | C₂H₅ | CH₂Ph |
| 553 | 2 | 1 | H | H | Cl | H | H |
| 554 | 1 | 3 | H | H | H | H | CH₂Ph |
| 555 | 1 | 3 | H | H | CH₃ | H | CH₂Ph |
| 556 | 1 | 3 | H | H | Cl | H | CH₂Ph |
| 557 | 1 | 3 | H | H | H | CH₃ | CH₂Ph |
| 558 | 2 | 2 | H | H | H | H | CH₂Ph |
| 559 | 2 | 2 | H | H | CH₃ | H | CH₂Ph |
| 560 | 2 | 2 | H | H | Cl | H | CH₂Ph |
| 561 | 2 | 2 | H | H | H | CH₃ | CH₂Ph |
| 562 | 3 | 1 | H | H | H | H | CH₂Ph |
| 563 | 3 | 1 | H | H | CH₃ | H | CH₂Ph |
| 564 | 3 | 1 | H | H | Cl | H | CH₂Ph |
| 565 | 3 | 1 | H | H | H | CH₃ | CH₂Ph |
| 566 | 0 | 5 | H | H | H | H | CH₂Ph |
| 567 | 0 | 5 | H | H | CH₃ | H | CH₂Ph |
| 568 | 0 | 5 | H | H | Cl | H | CH₂Ph |
| 569 | 0 | 5 | H | H | H | CH₃ | CH₂Ph |
| 570 | 1 | 4 | H | H | H | H | CH₂Ph |
| 571 | 1 | 4 | H | H | CH₃ | H | CH₂Ph |
| 572 | 1 | 4 | H | H | Cl | H | CH₂Ph |
| 573 | 1 | 4 | H | H | H | CH₃ | CH₂Ph |
| 574 | 2 | 3 | H | H | H | H | CH₂Ph |
| 575 | 2 | 3 | H | H | CH₃ | H | CH₂Ph |
| 576 | 2 | 3 | H | H | Cl | H | CH₂Ph |
| 577 | 2 | 3 | H | H | H | CH₃ | CH₂Ph |
| 578 | 3 | 2 | H | H | H | H | CH₂Ph |
| 579 | 3 | 2 | H | H | CH₃ | H | CH₂Ph |
| 580 | 3 | 2 | H | H | Cl | H | CH₂Ph |
| 581 | 3 | 2 | H | H | H | CH₃ | CH₂Ph |
| 582 | 0 | 6 | H | H | H | H | CH₂Ph |
| 583 | 0 | 6 | H | H | CH₃ | H | CH₂Ph |
| 584 | 0 | 6 | H | H | Cl | H | CH₂Ph |
| 585 | 0 | 6 | H | H | H | CH₃ | CH₂Ph |
| 586 | 1 | 5 | H | H | H | H | CH₂Ph |
| 587 | 1 | 5 | H | H | CH₃ | H | CH₂Ph |
| 588 | 1 | 5 | H | H | Cl | H | CH₂Ph |
| 589 | 1 | 5 | H | H | H | CH₃ | CH₂Ph |
| 590 | 2 | 4 | H | H | H | H | CH₂Ph |
| 591 | 2 | 4 | H | H | CH₃ | H | CH₂Ph |
| 592 | 2 | 4 | H | H | Cl | H | CH₂Ph |
| 593 | 2 | 4 | H | H | H | CH₃ | CH₂Ph |
| 594 | 3 | 3 | H | H | H | H | CH₂Ph |
| 595 | 3 | 3 | H | H | CH₃ | H | CH₂Ph |

-continued

| | | | | | | | |
|---|---|---|---|---|---|---|---|
| 596 | 3 | 3 | H | H | Cl | H | CH$_2$Ph |
| 597 | 3 | 3 | H | H | H | CH$_3$ | CH$_2$Ph |

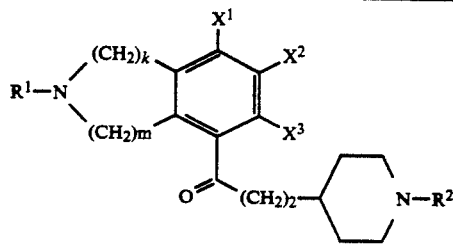

| No. | k | m | X$^1$ | X$^2$ | X$^3$ | R$^1$ | R$^2$ |
|---|---|---|---|---|---|---|---|
| 598 | 0 | 2 | CH$_3$ | H | H | H | CH$_2$Ph |
| 599 | 0 | 2 | Cl | H | H | H | CH$_2$Ph |
| 600 | 0 | 2 | H | H | H | COCH$_3$ | CH$_2$Ph |
| 601 | 0 | 2 | OCH$_3$ | H | H | CH$_3$ | CH$_2$Ph |
| 602 | 0 | 2 | CH$_3$ | H | H | H | H |
| 603 | 0 | 3 | H | H | H | H | CH$_2$Ph |
| 604 | 0 | 3 | H | H | H | CH$_3$ | CH$_2$Ph |
| 605 | 0 | 3 | CH$_3$ | H | H | CH$_3$ | CH$_2$Ph |
| 606 | 0 | 3 | OCH$_3$ | H | H | H | CH$_2$Ph |
| 607 | 0 | 3 | H | H | H | H | H |
| 608 | 0 | 5 | Cl | H | H | H | CH$_2$Ph |
| 609 | 0 | 5 | H | H | H | H | CH$_2$Ph |
| 610 | 0 | 5 | CH$_3$ | H | H | CH$_3$ | CH$_2$Ph |
| 611 | 0 | 5 | OCH$_3$ | H | H | H | CH$_2$Ph |
| 612 | 0 | 5 | H | H | H | H | H |
| 613 | 1 | 4 | H | H | H | H | CH$_2$Ph |
| 614 | 1 | 4 | CH$_3$ | H | H | H | CH$_2$Ph |
| 615 | 1 | 4 | OCH$_3$ | H | H | H | CH$_2$Ph |
| 616 | 1 | 4 | H | H | H | CH$_3$ | CH$_2$Ph |
| 617 | 0 | 6 | H | H | H | H | CH$_2$Ph |
| 618 | 0 | 6 | CH$_3$ | H | H | H | CH$_2$Ph |
| 619 | 0 | 6 | Cl | H | H | H | CH$_2$Ph |
| 620 | 0 | 6 | H | H | H | CH$_3$ | CH$_2$Ph |
| 621 | 0 | 6 | H | H | H | H | CH$_2$Ph |
| 622 | 0 | 6 | H | H | H | CH$_2$Ph | CH$_2$Ph |
| 623 | 0 | 6 | H | H | H | C$_2$H$_5$ | CH$_2$Ph |
| 624 | 0 | 6 | H | H | H | COPh | CH$_2$Ph |
| 625 | 0 | 6 | H | H | H | COCH$_3$ | CH$_2$Ph |
| 626 | 0 | 6 | H | H | H | COPh | CH$_2$Ph |
| 627 | 0 | 6 | F | H | H | CH$_3$ | CH$_2$Ph |
| 628 | 0 | 6 | F | H | CH$_3$ | H | CH$_2$Ph |
| 629 | 0 | 6 | CH$_3$ | H | H | H | H |
| 630 | 1 | 5 | H | H | H | H | CH$_2$Ph |
| 631 | 1 | 5 | CH$_3$ | H | H | H | CH$_2$Ph |
| 632 | 1 | 5 | Cl | H | H | H | CH$_2$Ph |
| 633 | 1 | 5 | H | H | H | CH$_3$ | CH$_2$Ph |
| 634 | 2 | 4 | H | H | H | H | CH$_2$Ph |
| 635 | 2 | 4 | CH$_3$ | H | H | H | CH$_2$Ph |
| 636 | 2 | 4 | OCH$_3$ | H | H | H | CH$_2$Ph |
| 637 | 2 | 4 | H | H | H | CH$_3$ | CH$_2$Ph |

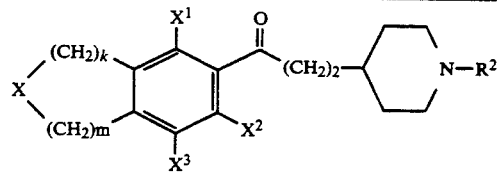

| No. | X | k | m | X$^1$ | X$^2$ | X$^3$ | R$^2$ |
|---|---|---|---|---|---|---|---|
| 638 | O | 0 | 2 | H | H | H | CH$_2$Ph |
| 639 | O | 0 | 2 | H | H | CH$_3$ | CH$_2$Ph |
| 640 | O | 0 | 2 | H | H | H | H |
| 641 | O | 1 | 1 | H | H | H | CH$_2$Ph |
| 642 | O | 1 | 1 | H | H | CH$_3$ | CH$_2$Ph |
| 643 | O | 1 | 1 | H | H | OCH$_3$ | CH$_2$Ph |
| 644 | O | 0 | 3 | H | H | H | CH$_2$Ph |
| 645 | O | 0 | 3 | H | H | Cl | CH$_2$Ph |
| 646 | O | 0 | 3 | H | H | OCH$_3$ | CH$_2$Ph |
| 647 | O | 1 | 2 | H | H | C$_2$H$_5$ | CH$_2$Ph |
| 648 | O | 1 | 2 | H | H | H | H |
| 649 | O | 1 | 2 | H | CH$_3$ | H | CH$_2$ |
| 650 | O | 2 | 1 | H | H | H | CH$_2$Ph |
| 651 | O | 2 | 1 | H | H | CH$_3$ | CH$_2$Ph |
| 652 | O | 2 | 1 | H | H | C$_2$H$_5$ | CH$_2$Ph |

-continued

| | | | | | | | |
|---|---|---|---|---|---|---|---|
| 653 | O | 0 | 4 | H | H | H | H |
| 654 | O | 0 | 4 | H | H | H | CH$_2$Ph |
| 655 | O | 0 | 4 | H | H | CH$_3$ | CH$_2$Ph |
| 656 | O | 1 | 3 | H | H | H | CH$_2$Ph |
| 657 | O | 1 | 3 | H | H | CH$_3$ | CH$_2$Ph |
| 658 | O | 1 | 3 | H | H | H | CH$_3$ |
| 659 | O | 2 | 2 | H | CH$_3$ | H | CH$_2$Ph |
| 660 | O | 2 | 2 | H | H | H | CH$_2$Ph |
| 661 | O | 2 | 2 | H | H | OH | CH$_2$Ph |
| 662 | O | 3 | 1 | H | H | H | CH$_2$Ph |
| 663 | O | 3 | 1 | H | H | F | CH$_2$Ph |
| 664 | O | 3 | 1 | H | OH | Cl | CH$_2$Ph |
| 665 | O | 0 | 5 | H | H | CH$_3$ | CH$_2$Ph |
| 666 | O | 0 | 5 | H | H | H | CH$_2$Ph |
| 667 | O | 1 | 4 | H | OCH$_3$ | H | CH$_2$Ph |
| 668 | O | 1 | 4 | H | H | H | CH$_2$Ph |
| 669 | O | 2 | 3 | H | H | H | CH$_2$Ph |
| 670 | O | 2 | 3 | H | H | OH | CH$_2$Ph |
| 671 | O | 3 | 2 | H | CH$_3$ | H | CH$_2$Ph |
| 672 | O | 3 | 2 | H | Cl | CH$_3$ | CH$_2$Ph |
| 673 | O | 0 | 6 | H | H | H | CH$_2$Ph |
| 674 | O | 0 | 6 | H | H | H | H |
| 675 | O | 1 | 5 | OH | H | H | CH$_2$Ph |
| 676 | O | 1 | 5 | H | H | H | CH$_2$Ph |
| 677 | O | 2 | 4 | H | H | CH$_3$ | CH$_2$Ph |
| 678 | O | 2 | 4 | H | H | H | CH$_2$Ph |
| 679 | O | 3 | 3 | H | CH$_3$ | H | CH$_2$Ph |
| 680 | O | 3 | 3 | H | H | H | CH$_2$Ph |
| 681 | S | 0 | 2 | H | H | H | CH$_2$Ph |
| 682 | S | 0 | 2 | H | H | CH$_3$ | CH$_2$Ph |
| 683 | S | 0 | 2 | H | H | H | H |
| 684 | S | 1 | 1 | H | H | H | CH$_2$Ph |
| 685 | S | 1 | 1 | H | H | CH$_3$ | CH$_2$Ph |
| 686 | S | 1 | 1 | H | H | OCH$_3$ | CH$_2$Ph |
| 687 | S | 0 | 3 | H | H | H | CH$_2$Ph |
| 688 | S | 0 | 3 | H | H | Cl | CH$_2$Ph |
| 689 | S | 0 | 3 | H | H | OCH$_3$ | CH$_2$Ph |
| 690 | S | 1 | 2 | H | H | C$_2$H$_5$ | CH$_2$Ph |
| 691 | S | 1 | 2 | H | H | H | H |
| 692 | S | 1 | 2 | H | CH$_3$ | H | CH=CH—C$_6$H$_5$ |
| 693 | S | 2 | 1 | H | H | H | CH$_2$Ph |
| 694 | S | 2 | 1 | H | H | CH$_3$ | CH$_2$Ph |
| 695 | S | 2 | 1 | H | H | C$_2$H$_5$ | CH$_2$Ph |
| 696 | S | 0 | 4 | H | H | H | H |
| 697 | S | 0 | 4 | H | H | H | CH$_2$Ph |
| 698 | S | 0 | 4 | H | H | CH$_3$ | CH$_2$Ph |
| 699 | S | 1 | 3 | H | H | H | CH$_2$Ph |
| 700 | S | 1 | 3 | H | H | CH$_3$ | CH$_2$Ph |
| 701 | S | 1 | 3 | H | H | H | CH$_3$ |
| 702 | S | 2 | 2 | H | CH$_3$ | H | CH$_2$Ph |
| 703 | S | 2 | 2 | H | H | H | CH$_2$Ph |
| 704 | S | 2 | 2 | H | H | OH | CH$_2$Ph |
| 705 | S | 3 | 1 | H | H | H | CH$_2$Ph |
| 706 | S | 3 | 1 | H | H | F | CH$_2$Ph |
| 707 | S | 3 | 1 | H | OH | Cl | CH$_2$Ph |
| 708 | S | 0 | 5 | H | H | CH$_3$ | CH$_2$Ph |
| 709 | S | 0 | 5 | H | H | H | CH$_2$Ph |
| 710 | S | 1 | 4 | H | OCH$_3$ | H | CH$_2$Ph |
| 711 | S | 1 | 4 | H | H | H | CH$_2$Ph |
| 712 | S | 2 | 3 | H | H | H | CH$_2$Ph |
| 713 | S | 2 | 3 | H | H | OH | CH$_2$Ph |
| 714 | S | 3 | 2 | H | CH$_3$ | H | CH$_2$Ph |
| 715 | S | 3 | 2 | H | Cl | CH$_3$ | CH$_2$Ph |
| 716 | S | 0 | 6 | H | H | H | CH$_2$Ph |
| 717 | S | 0 | 6 | H | H | H | H |
| 718 | S | 1 | 5 | OH | H | H | CH$_2$Ph |
| 719 | S | 1 | 5 | H | H | H | CH$_2$Ph |
| 720 | S | 2 | 4 | H | H | CH$_3$ | CH$_2$Ph |
| 721 | S | 2 | 4 | H | H | H | CH$_2$Ph |
| 722 | S | 3 | 3 | H | CH$_3$ | H | CH$_2$Ph |
| 723 | S | 3 | 3 | H | H | H | CH$_2$Ph |

-continued

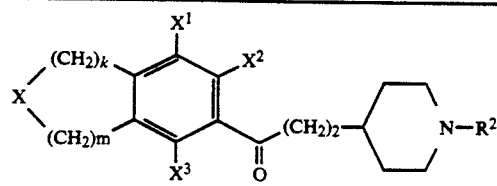

| No. | X | k | m | X¹ | X² | X³ | R² |
|---|---|---|---|---|---|---|---|
| 724 | O | 0 | 2 | H | H | H | CH₂Ph |
| 725 | O | 0 | 2 | CH₃ | H | H | CH₂Ph |
| 726 | O | 0 | 2 | H | H | H | H |
| 727 | O | 0 | 3 | H | H | H | CH₂Ph |
| 728 | O | 0 | 3 | OCH₃ | H | CH₃ | CH₂Ph |
| 729 | O | 0 | 3 | OH | H | OCH₃ | CH₂Ph |
| 730 | O | 0 | 4 | H | H | H | CH₂Ph |
| 731 | O | 0 | 4 | Cl | H | H | CH₂Ph |
| 732 | O | 0 | 4 | F | H | H | CH₂Ph |
| 733 | O | 1 | 4 | H | H | H | CH₂Ph |
| 734 | O | 1 | 4 | CH₃ | Cl | H | CH₂Ph |
| 735 | O | 0 | 5 | H | H | H | CH₂Ph |
| 736 | O | 0 | 5 | H | CH₃ | H | CH₂Ph |
| 737 | O | 2 | 4 | OH | H | H | CH₂Ph |
| 738 | O | 2 | 4 | H | H | H | CH₂Ph |
| 739 | O | 1 | 5 | H | H | H | CH₂Ph |
| 740 | O | 0 | 6 | H | H | H | CH₂Ph |
| 741 | S | 0 | 2 | H | H | H | CH₂Ph |
| 742 | S | 0 | 2 | CH₃ | H | H | CH₂Ph |
| 743 | S | 0 | 2 | H | H | H | H |
| 744 | S | 0 | 3 | H | H | H | CH₂Ph |
| 745 | S | 0 | 3 | OCH₃ | H | CH₃ | CH₂Ph |
| 746 | S | 0 | 3 | OH | H | OCH₃ | CH₂Ph |
| 747 | S | 0 | 4 | H | H | H | CH₂Ph |
| 748 | S | 0 | 4 | Cl | H | H | CH₂Ph |
| 749 | S | 0 | 4 | F | H | H | CH₂Ph |
| 750 | S | 1 | 4 | H | H | H | CH₂Ph |
| 751 | S | 1 | 4 | CH₃ | Cl | H | CH₂Ph |
| 752 | S | 0 | 5 | H | H | H | CH₂Ph |
| 753 | S | 0 | 5 | H | CH₃ | H | CH₂Ph |
| 754 | S | 2 | 4 | OH | H | H | CH₂Ph |
| 755 | S | 2 | 4 | H | H | H | CH₂Ph |
| 756 | S | 1 | 5 | H | H | H | CH₂Ph |
| 757 | S | 0 | 6 | H | H | H | CH₂Ph |

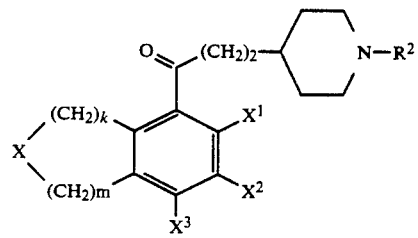

| No. | X | k | m | X¹ | X² | X³ | R² |
|---|---|---|---|---|---|---|---|
| 758 | O | 0 | 2 | H | H | H | CH₂Ph |
| 759 | O | 0 | 2 | H | H | H | CH₂Ph |
| 760 | O | 1 | 1 | H | H | H | CH₂Ph |
| 761 | O | 1 | 1 | OCH₃ | H | CH₃ | CH₂Ph |
| 762 | O | 0 | 3 | H | H | H | CH₂Ph |
| 763 | O | 0 | 3 | H | H | Cl | CH₂Ph |
| 764 | O | 1 | 2 | H | H | H | CH₂Ph |
| 765 | O | 1 | 2 | H | Cl | CH₃ | CH₂Ph |
| 766 | O | 2 | 1 | H | H | H | CH₂Ph |
| 767 | O | 2 | 1 | H | CH₃ | H | CH₂Ph |
| 768 | O | 0 | 4 | H | H | OH | CH₂Ph |
| 769 | O | 0 | 4 | H | H | H | CH₂Ph |
| 770 | O | 1 | 3 | H | H | H | CH₂Ph |
| 771 | O | 1 | 3 | H | H | Cl | CH₂Ph |
| 772 | O | 2 | 2 | H | H | H | CH₂Ph |
| 773 | O | 2 | 2 | OCH₃ | H | CH₃ | CH₂Ph |
| 774 | O | 3 | 1 | H | H | H | CH₂Ph |
| 775 | O | 3 | 1 | H | H | Cl | CH₂Ph |
| 776 | O | 0 | 5 | H | H | H | CH₂Ph |
| 777 | O | 0 | 5 | H | Cl | CH₃ | CH₂Ph |
| 778 | O | 1 | 4 | H | H | H | CH₂Ph |
| 779 | O | 1 | 4 | H | CH₃ | H | CH₂Ph |
| 780 | O | 2 | 3 | H | H | OH | CH₂Ph |

-continued

| | | | | | | | |
|---|---|---|---|---|---|---|---|
| 781 | O | 2 | 3 | H | H | H | CH₂Ph |
| 782 | O | 3 | 2 | H | H | H | CH₂Ph |
| 783 | O | 3 | 2 | H | H | F | CH₂Ph |
| 784 | O | 0 | 6 | H | H | H | CH₂Ph |
| 785 | O | 0 | 6 | H | Cl | CH₃ | CH₂Ph |
| 786 | O | 1 | 5 | H | H | H | CH₂Ph |
| 787 | O | 1 | 5 | H | CH₃ | H | CH₂Ph |
| 788 | O | 2 | 4 | H | H | OH | CH₂Ph |
| 789 | O | 2 | 4 | H | H | H | CH₂Ph |
| 790 | O | 3 | 3 | H | H | H | CH₂Ph |
| 791 | O | 3 | 3 | H | H | F | CH₂Ph |
| 792 | S | 0 | 3 | H | H | H | CH₂Ph |
| 793 | S | 0 | 2 | H | H | H | CH₂Ph |
| 794 | S | 1 | 1 | H | H | H | CH₂Ph |
| 795 | S | 1 | 1 | OCH₃ | H | CH₃ | CH₂Ph |
| 796 | S | 0 | 3 | H | H | H | CH₂Ph |
| 797 | S | 0 | 3 | H | H | Cl | CH₂Ph |
| 798 | S | 1 | 2 | H | H | H | CH₂Ph |
| 799 | S | 1 | 2 | H | Cl | CH₃ | CH₂Ph |
| 800 | S | 2 | 1 | H | H | H | CH₂Ph |
| 801 | S | 2 | 1 | H | CH₃ | H | CH₂Ph |
| 802 | S | 0 | 4 | H | H | OH | CH₂Ph |
| 803 | S | 0 | 4 | H | H | H | CH₂Ph |
| 804 | S | 1 | 3 | H | H | H | CH₂Ph |
| 805 | S | 1 | 3 | H | H | Cl | CH₂Ph |
| 806 | S | 2 | 2 | H | H | H | CH₂Ph |
| 807 | S | 2 | 2 | OCH₃ | H | CH₃ | CH₂Ph |
| 808 | S | 3 | 1 | H | H | H | CH₂Ph |
| 809 | S | 3 | 1 | H | H | Cl | CH₂Ph |
| 810 | S | 0 | 5 | H | H | H | CH₂Ph |
| 811 | S | 0 | 5 | H | Cl | CH₃ | CH₂Ph |
| 812 | S | 1 | 4 | H | H | H | CH₂Ph |
| 813 | S | 1 | 4 | H | CH₃ | H | CH₂Ph |
| 814 | S | 2 | 3 | H | H | OH | CH₂Ph |
| 815 | S | 2 | 3 | H | H | H | CH₂Ph |
| 816 | S | 3 | 2 | H | H | H | CH₂Ph |
| 817 | S | 3 | 2 | H | H | F | CH₂Ph |
| 818 | S | 0 | 6 | H | H | H | CH₂Ph |
| 819 | S | 0 | 6 | H | Cl | CH₃ | CH₂Ph |
| 820 | S | 1 | 5 | H | H | H | CH₂Ph |
| 821 | S | 1 | 5 | H | CH₃ | H | CH₂Ph |
| 822 | S | 2 | 4 | H | H | OH | CH₂Ph |
| 823 | S | 2 | 4 | H | H | H | CH₂Ph |
| 824 | S | 3 | 3 | H | H | H | CH₂Ph |
| 825 | S | 3 | 3 | H | H | F | CH₂Ph |

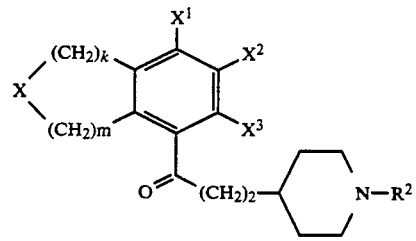

| No. | X | k | m | X¹ | X² | X³ | R² |
|---|---|---|---|---|---|---|---|
| 826 | O | 0 | 2 | H | H | H | CH₂Ph |
| 827 | O | 0 | 2 | CH₃ | H | H | CH₂Ph |
| 828 | O | 0 | 3 | H | H | H | CH₂Ph |
| 829 | O | 0 | 3 | OCH₃ | H | CH₃ | CH₂Ph |
| 830 | O | 0 | 4 | H | H | H | CH₂Ph |
| 831 | O | 0 | 4 | Cl | H | H | CH₂Ph |
| 832 | O | 1 | 4 | H | H | H | CH₂Ph |
| 833 | O | 1 | 4 | OH | Cl | H | CH₂Ph |
| 834 | O | 0 | 5 | H | H | H | CH₂Ph |
| 835 | O | 0 | 5 | H | CH₃ | H | CH₂Ph |
| 836 | O | 2 | 4 | OCH₃ | H | OH | CH₂Ph |
| 837 | O | 2 | 4 | H | H | H | CH₂Ph |
| 838 | O | 1 | 5 | H | H | H | CH₂Ph |
| 839 | O | 0 | 6 | H | H | H | CH₂Ph |
| 840 | S | 0 | 2 | H | H | H | CH₂Ph |
| 841 | S | 0 | 2 | OCH₃ | H | H | CH₂Ph |
| 842 | S | 0 | 3 | H | H | H | CH₂Ph |
| 843 | S | 0 | 3 | OCH₃ | H | CH₃ | CH₂Ph |
| 844 | S | 0 | 4 | H | H | H | CH₂Ph |
| 845 | S | 0 | 4 | F | H | H | CH₂Ph |
| 846 | S | 1 | 4 | H | H | H | CH₂Ph |
| 847 | S | 1 | 4 | CH₃ | Cl | H | CH₂Ph |
| 848 | S | 0 | 5 | H | H | H | CH₂Ph |

-continued

| | | | | | | | |
|---|---|---|---|---|---|---|---|
| 849 | S | 0 | 5 | H | CH$_3$ | H | CH$_2$Ph |
| 850 | S | 2 | 4 | H | H | H | CH$_2$Ph |
| 851 | S | 2 | 4 | CH$_3$ | H | H | CH$_2$Ph |
| 852 | S | 1 | 5 | H | H | H | CH$_2$Ph |
| 853 | S | 0 | 6 | H | H | H | CH$_2$Ph |

The salt of compound (I) according to the present invention is preferably a physiologically acceptable acid addition salt. The salt mentioned above includes salts with inorganic acids (e.g. hydrochloric acid, phosphoric acid, hydrobromic acid, sulfuric acid) and salts with organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid).

Furthermore, when the compound (I) according to the present invention has an acidic group such as COOH, compound (I) may form a salt with an inorganic base (e.g. sodium, potassium, calcium, magnesium, ammonia) or an organic base (e.g. triethylamine).

The process for producing the compound (I) or its salt of the invention is now described.

While the following description of the production process applies not only to the production of compound (I) but also to the production of its salt, they may be referred to as the compound (I) below.

The compound (I) can be produced by reacting a compound of the formula (II):

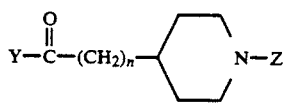

(II)

wherein Y is a halogen; n is as defined in formula (I); Z is an amino-protecting group or a salt thereof with a compound of the formula (III):

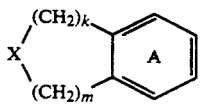

(III)

wherein each symbol is as defined in formula (I), or a salt thereof and deprotecting the resulting compound of the formula (IV):

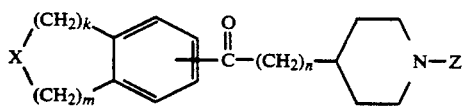

(IV)

wherein each symbol is as defined hereinbefore or a salt thereof.

Y is preferably chloro, bromo or iodo, and a more preferable example of Y is chloro.

Z is preferably acetyl, benzoyl, formyl, methoxycarbonyl, ethoxycarbonyl, t-butoxycarbonyl or benzyloxycarbonyl, and more preferable examples of Z include acetyl and benzoyl.

Here, the compound of formula (II) or a salt thereof can be prepared analogously thereto. For example, it can be produced by the process described in Chemical Pharmaceutical Bulletin, 34, 3747-3761 (1986). The compound of formula (III) or a salt thereof can be prepared by processes which are known per se or processes analogous thereto. For example, it can be produced by the processes described in Journal of the Organic Chemistry 34, 2235 (1969), Journal of the Organic Chemistry 54, 5574 (1989), Tetrahedron letters 35, 3023 (1977), Bulletin of the Chemical Society of Japan, 56 2300 (1983) and so on.

The salt of compound (II) or compound (IV) according to the present invention is preferably a physiologically acceptable acid addition salt. The salt mentioned above includes salts with inorganic acids (e.g. hydrochloric acid, phosphoric acid, hydrobromic acid, sulfuric acid) and salts with organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid).

The reaction between compound (II) or a salt thereof (e.g. one of the salts mentioned for formula (I)) and compound (III) or a salt thereof can be carried out as follows, for instance. Thus, the compound (II) or a salt thereof is allowed to react with the compound (III) without using a solvent or in a solvent, where necessary in the presence of an acid or the like. The acid may be a Lewis acid (e.g. aluminum chloride, zinc chloride, titanium chloride). The amount of such acid is generally used at a ratio of 1 to 20 moles and preferably 2 to 10 moles relative to one mole of the compound (II). The solvent may be any of the common solvents used in chemical reactions provided it does not interfere with the reaction. For example, dichloromethane, dichloroethane, nitrobenzene, carbon disulfide, etc. can be employed as the solvent. The reaction temperature is generally about −30° C. to 150° C. and preferably about 20° C. to 100° C. The reaction time is generally 0.5 to 72 hours. The amount of compound (III) or a salt thereof is generally used at a ratio of 1 to 20 moles and preferably about 1 to 5 moles relative to one mole of the compound (II) or a salt thereof.

The position of introduction of the group

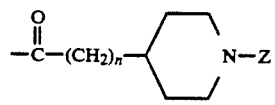

of formula (II) into the compound of formula (III) in the above reaction may be any positions of ring A which can be substituted. For example it is predominantly the 6-position when the skeletal structure of compound (III) is 1,2,3,4-tetrahydroquinoline (where ring A is unsubstituted). However, the compounds formed upon introduction into other positions (5-, 7- and 8-positions) may also be produced and isolated.

The compound (IV) or a salt thereof thus produced can be isolated and purified by the conventional procedures such as concentration, pH adjustment, redistribution, solvent extraction, fractional distillation, distillation, crystallization, recrystallization, chromatography and so on. However, the reaction mixture may be directly used as the material to the next reaction stage.

The deprotection of the compound (IV) or a salt thereof can be carried out by treating the compound (IV) or a salt thereof with an acid or a base. Thus, the compound of formula (IV) or a salt thereof is maintained in an aqueous solution of mineral acid (e.g. nitric acid, hydrochloric acid, hydrobromic acid, iodic acid, sulfuric acid) or alkali metal hydroxide (e.g. sodium hydroxide, potassium hydroxide, barium hydroxide, lithium hydroxide) at 10° to 150° C., preferably at 50° to 100° C. Such acid or base is generally used at a ratio of 1 to 100 equivalents and preferably 1 to 40 equivalents relative to the compound (IV) or a salt thereof. The strength of the acid or base is generally about 1 to 10 N, and preferably about 4 to 10 N. The reaction time, which depends on the reaction temperature, is generally 1 to 24 hours and preferably about 2 to 10 hours.

The compound (I) ($R^2$=H) or a salt thereof thus produced can be isolated and purified by the conventional procedures such as concentration, pH adjustment, redistribution, solvent extraction, fractional distillation, distillation, crystallization, recrystallization, chromatography and so on. However, the reaction mixture may be directly used as the material to the next reaction stage.

The compound (I) wherein $R^2$ is a group other than a hydrogen atom or a salt thereof can be produced by reacting a compound (I) ($R^2$=H) or a salt thereof with a compound of formula $$R^{2'}-Y' \qquad (V)$$

wherein $R^{2'}$ is a hydrocarbon group which may be substituted; and Y' is a leaving group.

The leaving group Y' includes halogen (e.g. chloro, bromo, iodo), $C_{1-6}$ alkylsulfonyloxy (e.g. methanesulfonyloxy, ethanesulfonyloxy) and $C_{6-10}$ arylsulfonyloxy (e.g. benzenesulfonyloxy, p-toluenesulfonyloxy).

The reaction between the compound (I) ($R^2$=H) or a salt thereof and the compound (V) is conducted in a solvent or without using a solvent, where necessary in the presence of a base.

The base mentioned just above includes various inorganic bases such as sodium carbonate, potassium carbonate, lithium carbonate, sodium hydroxide, potassium hydroxide, sodium methoxide, sodium ethoxide, sodium hydride, etc. and various organic bases such as pyridine, 4-dimethylaminopyridine, triethylamine and so on. When a solvent is employed, the solvent includes lower alcohols such as methanol, ethanol, propanol, isopropyl alcohol, n-butanol, t-butanol, etc., ethers such as dioxane, ether, tetrahydrofuran, etc., aromatic hydrocarbons such as toluene, benzene, xylene, etc., amides such as dimethylformamide, dimethylacetamide, hexamethylphosphonotriamide, etc., esters such as ethyl acetate, butyl acetate, etc. which do not interfere with the reaction. This reaction can be conducted under cooling (about 0° C. to 10° C.), at room temperature (about 10° C. to 40° C.) or under heating (about 40° C. to 120° C.), and the reaction time is generally 10 minutes to 48 hours and preferably 2 to 16 hours.

The preferred amount of compound (V) is generally at a ratio of 0.3 to 5.0 moles relative to one mole of the compound (I) ($R^2$=H) or a salt thereof. When a base is employed, the amount of the base is generally used at a ratio of more than one mole and preferably 1.1 to 5 moles relative to one mole of the compound (I) ($R^2$=H) or its salt.

If desired, this reaction may be hastened by conducting it in the presence of sodium iodide, potassium iodide, lithium iodide or the like. In such cases, the amount of such iodide is generally used at a ratio of 1 to 5 moles and preferably 1.1 to 1.5 moles relative to one mole of the compound (V). Furthermore, the compound (I) or a salt thereof can also be produced by reacting a compound of the formula (VI):

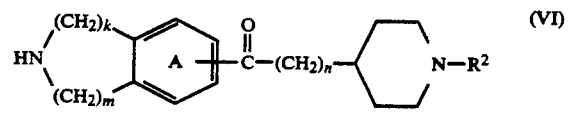

wherein k, m, n, ring A and $R^2$ are as defined hereinbefore or a salt thereof with a compound of the formula (VII):

wherein $R^{1'}$ is a hydrocarbon group which may be substituted or an acyl group which may be substituted; Y' is as defined hereinbefore, under the same conditions as those mentioned for the reaction between the compound (I) ($R^2$=H) or a salt thereof and the compound (V). Here, the compound of formula (VI) or a salt thereof can be produced by the processes mentioned above and can be also produced by hydrolyzing the compound (I)($R^2 \neq H$) in which $R^1$ is acyl or a salt thereof with an acid or a base. This hydrolyzing reaction can be conducted in the same manner as the deprotection of the compound (IV) or a salt thereof.

The compound (I) can also be produced by other known processes or processes analogous thereto (e.g. the compound (I) can be prepared by reduction of the compounds (IV), wherein Z is a carboxylic acid acyl, protection and deprotection of functional groups of the compound (IV) such as ketone may be necessary in the process).

When the compound (I) thus obtained is a free compound, it can be converted to its salt in the per se conventional manner. When the product compound is a salt, it can be converted to the free compound or a different salt by the per se known procedure. The compound (I) or its salt thus obtained can be isolated and purified by the known procedures mentioned hereinbefore.

The compound (I) or its salt according to the present invention has effects on the central nervous system of mammals, has high cholinesterase inhibitory activity, and exhibits potent antiamnesic effects on various amnesia-inducing factors in man and animals (e.g. mice).

The compound (I) or its salt according to the present invention features an excellent separation between effects on the central nervous system and those on the peripheral nervous system, as compared with physostigmine and, at the antiamnesic dose level, does not cause peripheral nervous system effects such as spasm, salivation and diarrhea or, if it does, only minimally. Moreover, it is characterized by a long duration of effects as well as low toxicity and insures a high efficacy when administered orally. The acute toxicity of the compound (I) or its salt according to the present invention is beyond 100 mg/kg.

Therefore, the compound (I) or a salt thereof of the present invention is useful as an agent to improve the brain function for mammalian animals including human beings.

The compound (I) or a salt thereof of the present invention may be used for such diseases as senile dementia, Alzheimer's disease, Huntington's chorea, hyperkinesia and mania, and may be used for the prophylaxis or therapy of these diseases.

The compound (I) or a salt thereof according to the present invention is generally formulated with a pharmaceutically acceptable carrier or excipient and can be administered orally or parenterally to man and other mammalians.

Such pharmaceutical preparations may be those for oral administration (e.g. powders, tablets, granules, capsules, etc.) or for parenteral administration (e.g. suppositories, injections). These preparations can be manufactured by the per se known methods. While the dosage depends on the type of disease and the symptom to be controlled, the usual daily oral dosage per adult human is about 0.01 to 100 mg, preferably 0.1 to 30 mg, and more preferably 0.3 to 10 mg.

The following reference examples, working examples, formulation examples and test examples are intended to illustrate the present invention in further detail and should by no means be construed as defining the metes and bounds of the invention.

In the examples and reference examples, elution in the procedure of column chromatography was carried out under monitor by TLC (Thin-Layer Chromatography) unless otherwise indicated. TLC monitoring was performed using Merck Kieselgel 60 $F_{254}$ (E. Merck) as the TLC plate, the column elution solvent as the developer and a UV detector for detection. As an adjunctive detection procedure, the spot on the TLC plate was sprayed with 48% HBr, heated to hydrolyze, sprayed with ninhydrin reagent and reheated and the change to a red—reddish purple color was regarded as positive reaction. The fractions containing the object compound were thus identified and pooled. Unless otherwise specified, Merck Kieselgel 60 (70 to 230 mesh (E. Merck)) was used as the silica gel for chromatography.

The term "ambient temperature" or "room temperature" generally means about 5° C. to 40° C. and the term "atmospheric pressure" means the neighborhood of one atmosphere.

Unless otherwise specified, % denotes percentage by weight.

REFERENCE EXAMPLE 1

1-Acetyl-6-[3-(1-acetylpiperidin-4-yl)-1-oxopropyl]-1,2,3,4-tetrahydroquinoline

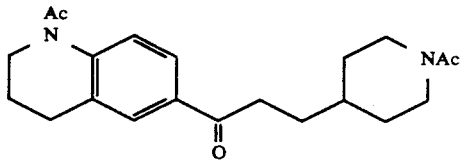

(1) In 300 ml of acetic acid was dissolved 33 g of ethyl β-(pyridin-4-yl)acrylate and catalytic hydrogenation was carried out with platinum oxide as the catalyst under atmospheric pressure at 70° to 80° C. After 40 ml of acetic anhydride was added, the catalyst was filtered off and the solvent was then distilled off under reduced pressure. The residue was dissolved in water and neutralized with potassium carbonate and the reaction product was extracted with dichloromethane. The extract was dried over anhydrous sodium sulfate and the solvent was distilled off to give 44.8 g of an oily compound.

(2) In 200 ml of methanol was dissolved 42.0 g of the above oily compound followed by addition of a solution of 12.7 g of potassium hydroxide in 20 ml of water. The mixture was stirred at 50° C. for 1.5 hours and at room temperature for 12 hours. The reaction mixture was neutralized with concentrated hydrochloric acid and the solvent was distilled off. To the residue was added methanol and the insoluble matter was filtered off. The filtrate was concentrated and the resulting crude crystals were collected by filtration to give 27 g of 3-(1-acetylpiperidin-4-yl)propionic acid (m.p. 201° to 206° C.).

(3) To 20 ml of thionyl chloride was added 3.8 g of 3-(1-acetylpiperidin-4-yl)propionic acid in small portions with ice-cooling and the mixture was stirred for 5 minutes. The excess thionyl chloride was distilled off and 15 g of carbon disulfide and 3.1 g of 1-acetyl-1,2,3,4-tetrahydroquinoline were added to the solid residue followed by gradual addition of 10.7 g of anhydrous aluminum chloride at room temperature. The mixture was refluxed for 2 hours, after which it was poured in ice-water and extracted with dichloromethane. The extract was dried over anhydrous sodium sulfate and the solvent was distilled off. The residue was purified by chromatography (eluent: ethyl acetatemethanol =40:1 (v/v)) to give 1.4 g of a colorless oil.

| Elemental analysis, for $C_{21}H_{28}N_2O_3$ | | | |
|---|---|---|---|
| Calcd.: | C, 70.76; | H, 7.92; | N, 7.86 |
| Found: | C, 70.68; | H, 7.80; | N, 7.64 |

REFERENCE EXAMPLE 2

1-Acetyl-6-[3-(1-acetylpiperidin-4-yl)-1-oxopropyl]-1,2,3,4-tetrahydroquinoline (A) and
1-acetyl-7-[3-(1-acetylpiperidin-4-yl)-1-oxopropyl]-1,2,3,4-tetrahydroquinoline (B)

(1) To 100 ml of thionyl chloride was added 26 g of 3-(1-acetylpiperidin-4-yl)propionic acid, obtained in Reference Example 1-(2), in small portions with ice-cooling. The mixture was stirred for 5 minutes, after which the excess thionyl chloride was distilled off and the solid residue was washed with diethyl ether to give 26.4 g of 3-(1-acetylpiperidin-4-yl)propionyl chloride as a pale yellow powder.

(2) To a mixture of 42.5 g of 1-acetyl-1,2,3,4-tetrahydroquinoline and 30 ml of carbon disulfide was added 71 g of anhydrous aluminum chloride followed by addition of 26.4 g of 3-(1-acetylpiperidin-4-yl)propionyl chloride at room temperature. The mixture was stirred at room temperature for 16 hours, after which it was treated in the same manner as Reference Example 1-(3) to give 25 g of a mixture of 1-acetyl-6-[3-(1-acetylpiperidin-4-yl)-1-oxopropyl]-1,2,3,4-tetrahydroquinoline (A) and 1-acetyl-7-[3-(1- acetylpiperidin-4-yl)-1-oxopropyl]-1,2,3,4-tetra-hydroquinoline (B) as a pale yellow oil.

| Elemental analysis, for $C_{21}H_{28}N_2O_3$ | | | |
|---|---|---|---|
| Calcd.: | C, 70.76; | H, 7.92; | N, 7.86 |

| Elemental analysis, for C$_{21}$H$_{28}$N$_2$O$_3$ | | | |
|---|---|---|---|
| Found: | C, 70.81; | H, 7.69; | N, 7.83 |

REFERENCE EXAMPLE 3

1-Acetyl-5-[3-(1-acetylpiperidin-4-yl)-1-oxopropyl]-2,3-dihydro-1H-indole

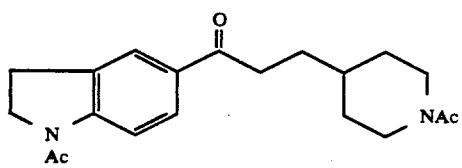

Using 24 g of 1-acetyl-2,3-dihydro-1H-indole, the procedure of Reference Example 2-(2) was followed to give a solid. This solid was recrystallized from dichloromethan-diethyl ether to give 26 g of colorless crystals melting at 148° to 149° C.

| Elemental analysis, for C$_{20}$H$_{26}$N$_2$O$_3$ | | | |
|---|---|---|---|
| Calcd.: | C, 70.15; | H, 7.65; | N, 8.18 |
| Found: | C, 69.97; | H, 7.71; | N, 7.98 |

REFERENCE EXAMPLE 4

1-Acetyl-8-[3-(1-acetylpiperidin-4-yl)-1-oxopropyl]-2,3,4,5-tetrahydro-1H-1-benzazepine (A) and
1-acetyl-7-[3-(1-acetylpiperidin-4-yl)-1-oxopropyl]-2,3,4,5-tetrahydro-1H-1-benzazepine (B)

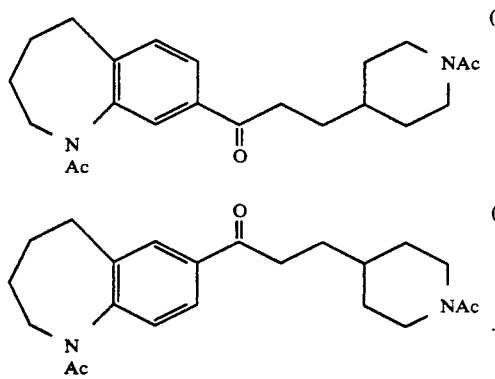

Using 8.7 g of 1-acetyl-2,3,4,5-tetrahydro-1H-1-benzazepine, the procedure of Reference Example 2-(2) was followed to give a solid, which was then recrystallized from dichloromethane-diethyl ether to give 6.5 g of title compound A as colorless crystals melting at 133° to 134° C.

| Elemental analysis, for C$_{22}$H$_{30}$N$_2$O$_3$ | | | |
|---|---|---|---|
| Calcd.: | C, 71.32; | H, 8.16; | N, 7.56 |
| Found: | C, 71.10; | H, 8.21; | N, 7.61 |

The recrystallization mother liquor was purified by column chromatography (eluent: ethyl acetate: methanol=100:1) to recover 0.3 g of title compound B as a pale yellow oil.

| Elemental analysis, for C$_{22}$H$_{30}$N$_2$O$_3$ | | | |
|---|---|---|---|
| Calcd.: | C, 71.32; | H, 8.16; | N, 7.56 |
| Found: | C, 71.13; | H, 8.04; | N, 7.43 |

REFERENCE EXAMPLE 5

8-[3-(1-Acetylpiperidin-4-yl)-1-oxopropyl]-2,3,4,5-tetrahydro-1H-1-benzazepine

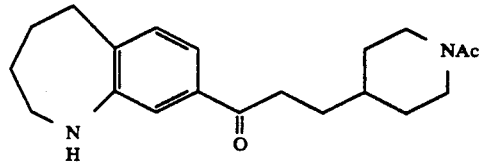

Using 2.2 g of the compound obtained in Example 17, the procedure of Example 7-(1) was followed to give 2.15 g of colorless crystals melting at 86° to 88° C.

| Elemental analysis, for C$_{20}$H$_{28}$N$_2$O$_2$ | | | |
|---|---|---|---|
| Calcd.: | C, 73.14; | H, 8.59; | N, 8.53 |
| Found: | C, 72.91; | H, 8.38; | N, 8.47 |

REFERENCE EXAMPLE 6

5-[3-(1-Acetylpiperidin-4-yl)-1-oxopropyl]-1-ethyl-2,3-dihydro-1H-indole

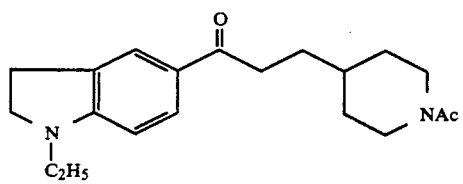

In 10 ml of ethanol were dissolved 0.8 g of 5-[3-(1-acetylpiperidin-4-yl)-1-oxopropyl]-2,3-dihydro-1H-indole, 2.1 g of ethyl iodide and 0.5 g of potassium carbonate and the solution was refluxed for 24 hours. The solid matter and the solvent were removed and the residue was purified by column chromatography (eluent: ethyl acetate: methanol=20:1) to give 0.85 g of the title compound as a pale yellow oil.

| Elemental analysis, for C$_{20}$H$_{28}$N$_2$O$_2$ | | | |
|---|---|---|---|
| Calcd.: | C, 73.14; | H, 8.59; | N, 8.53 |
| Found: | C, 73.03; | H, 8.54; | N, 8.56 |

REFERENCE EXAMPLE 7

Using the compound obtained in Example 14-(1) or Reference Example 5, the procedure of Reference Example 6 was followed to give the compounds as oil as follows.

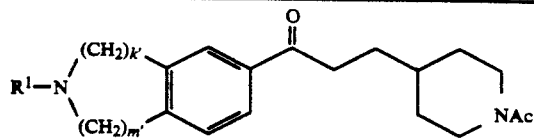

| Compound No. | k' | m' | R¹ | Molecular formula | Analysis Calcd. (Found) | | |
|---|---|---|---|---|---|---|---|
| | | | | | C | H | N |
| 1 | 2 | 0 | $C_3H_7$ | $C_{21}H_{30}N_2O_2$ | 73.65 (73.46 | 8.83 8.85 | 8.18 7.99) |
| 2 | 2 | 0 | $C_4H_9$ | $C_{22}H_{32}N_2O_2$ | 74.12 (74.03 | 9.05 9.02 | 7.86 7.61) |
| 3 | 2 | 0 | $C_5H_{11}$ | $C_{23}H_{34}N_2O_2$ | 74.56 (74.51 | 9.25 9.09 | 7.56 7.45) |
| 4 | 2 | 0 | $CH_2CH_2Ph$ | $C_{26}H_{32}N_2O_2$ | 77.19 (77.12 | 7.97 8.02 | 6.93 6.86) |
| 5 | 0 | 4 | $CH_3$ | $C_{21}H_{30}N_2O_2$ | 73.65 (73.55 | 8.83 8.73 | 8.18 8.16) |
| 6 | 0 | 4 | $C_2H_5$ | $C_{22}H_{32}N_2O_2$ | 74.12 (74.01 | 9.05 8.96 | 7.86 7.75) |
| 7 | 0 | 4 | $C_3H_7$ | $C_{23}H_{34}N_2O_2$ | 74.56 (74.37 | 9.25 9.11 | 7.56 7.43) |

REFERENCE EXAMPLE 8

5-[3-(1-Acetylpiperidin-4-yl)-1-oxopropyl]-2,3-dihydrobenzofuran

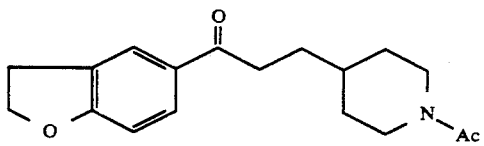

To 200 ml of 1,2-dichloroethane were added 9.65 g (44 mmol) of 3-(1-acetylpiperidin-4-yl)propionic acid chloride and 10.65 g (89 mmol), of 2,3-dihydrobenzofuran. To the mixture was added 12.82 g (96 mmol) of aluminum chloride in limited amounts, then the mixture was stirred for 3 hours at room temperature. The reaction mixture was poured into ice-water, which was subjected to extraction with methylene chloride. Organic layers were combined and washed with water and dried over anhydrous sodium sulfate, followed by distilling off the solvent. The residue was purified by means of a silica gel column chromatography (ethyl acetate) to give 10.47 g (78%) of 5-[3-(1-acetylpiperidin-4-yl)-1-oxopropyl]-2,3-dihydrobenzofuran. Recrystallization from methylene chloride—diethyl ether gave colorless needles, m.p. 93°-95° C.

| Elemental Analysis for $C_{18}H_{23}NO_3$: | | | |
|---|---|---|---|
| Calcd.: | C, 71.73; | H, 7.69; | N, 4.65 |
| Found: | C, 71.57; | H, 7.77; | N, 4.58 |

REFERENCE EXAMPLE 9

3-(1-Benzopiperidin-4-yl)propionic acid

(1) In 100 ml of acetic acid was dissolved 12 g of ethyl β-(pyridin-4-yl)acrylate and catalytic reduction was carried out with 1 g of platinum oxide as the catalyst under atmospheric pressure at 70°-80° C. The catalyst was filtered off and the solvent was distilled off under reduced pressure, then the residue was dissolved in 100 ml of dioxane. To the dioxane solution was added 100 ml of an aqueous solution of 12 g of sodium hydrogen carbonate, and the mixture was stirred for 20 minutes at room temperature. To the resultant mixture was added dropwise 8 ml of benzoyl chloride at room temperatures, and the mixture was stirred for two hours. The reaction product was extracted with dichloromethane. The extract was dried over anhydrous sodium sulfate and the solvent was distilled off to give 17.5 g of ethyl 3-(1-benzoylpiperidin-4-yl) propionate as an pale yellow oily product.

(2) Using 17 g of the compound obtained in (1), the procedure of Example 1-(2) was followed to give 15 g of the the above-titled compound as colorless crystals, m.p. 153°-155° C.

| Elemental Analysis for $C_{15}H_{19}NO_3$: | | | |
|---|---|---|---|
| Calcd.: | C, 68.94; | H, 7.33; | N, 5.36 |
| Found: | C, 68.71; | H, 7.44; | N, 5.20 |

REFERENCE EXAMPLE 10

3-Methoxycarbonyl-2,3,4,5-tetrahydro-1H-3-benzazepine

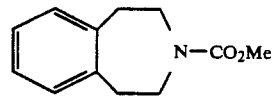

In 150 ml of water was dissolved 4.13 g (0.10 mol). of sodium hydroxide. To the solution was added 15.27 g (10.4 mmol.) of 2,3,4,5-tetrahydro-1H-3-benzazepine. The reaction mixture was cooled with ice, and there was added dropwise 7.9 ml (0.10 mol.) of methyl chloroformate. The mixture was stirred for 2.5 hours at room temperature, then extracted with dichloromethane. The extract was dried over anhydrous sodium sulfate and the solvent was distilled off to leave 20.46 g (96%) of 3-methoxycarbonyl-2,3,4,5-tetrahydro-1H-3-benzazepine as colorless crystals. Recrystallization from diethyl ether—n-hexane gave colorless needles, m.p. 53°-54° C. Elemental Analysis for $C_{12}H_{15}NO_2$:

| Elemental Analysis for $C_{12}H_{15}NO_2$: | | | |
|---|---|---|---|
| Calcd.: | C, 70.22; | H, 7.37; | N, 6.82 |
| Found: | C, 70.02; | H, 7.41; | N, 6.68 |

REFERENCE EXAMPLE 11

3-Methoxycarbonyl-7-[3-(1-benzoylpiperidin-4-yl)-1-oxopropyl]-2,3,4,5-tetrahydro-1H-3-benzazepine

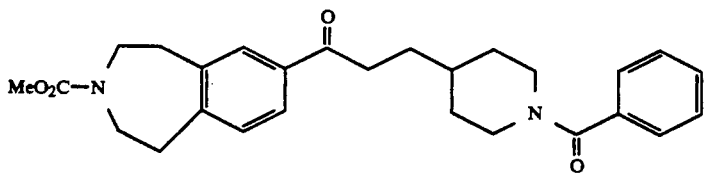

Under ice-cooling, 1.5 ml of thionyl chloride was added dropwise to 1.08 g (4.1 mmol.) of 3-(1-benzoylpiperidin-4-yl)propionic acid obtained in Reference Example 9. The mixture was stirred for 40 minutes at 0° C., then thionyl chloride was distilled off. The residue was dissolved in 20 ml of 1,2-dichloroethane, to which was added 0.81 g (3.9 mmol.) of 3- methoxycarbonyl-2,3,4,5-tetrahydro-1H-3-benzazepine obtained in Reference Example 10. To the mixture was added 1.75 g (13.1 mmol.) of aluminum chloride in small portions. The mixture was stirred for one hour at room temperature, then the reaction mixture was poured into ice-water and extracted with dichloromethane. The organic layers were combined and washed with water once, then dried over anhydrous sodium sulfate, followed by distilling off the solvent. Purification by means of a silica gel column chromatography gave 1.46 g (83%) of 3-methoxycarbonyl-7-[3-(1- benzoylpiperidin-4-yl)-1-oxopropyl]-2,3,4,5-tetrahydro-1H-3-benzazepine. Recrystallization from ethyl acetate —n-hexane gave colorless needles, m.p. 120°–123° C.

| Elemental Analysis for $C_{27}H_{32}N_2O_4$: | | | |
|---|---|---|---|
| Calcd.: | C, 72.30; | H, 7.19; | N, 6.25 |
| Found: | C, 71.99; | H, 7.22; | N, 6.12 |

REFERENCE EXAMPLE 12

6-[3-(1-Acetylpiperidin-4-yl)-1-oxopropyl]-3,4-dihydro-2H-1-benzothiopyran

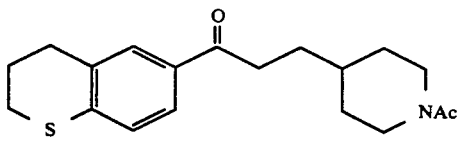

To a mixture of 3,4-dihydro-2H-1-benzothiopyran (1.5 g) and 3-(1-acetylpiperidin-4-yl)propionyl chloride (2.18 g) in 1,2-dichloroethane (20ml) was added aluminum chloride (3.2 g) portionwise at 10°–15° C. The mixture was stirred at room temperature for 2 hours then refluxed for additional 2 hours, and poured into icewater. The mixture was extracted with dichloromethane, washed with water, dried over anhydrous sodium sulfate. The solvent was distilled off. The residue was purified by silica gel column chromatography (developing solvent: ethyl acetate) to obtain 2.7 g of the title compound as a pale yellow oil.

| Elemental analysis, for $C_{19}H_{25}NO_2S$ | | | |
|---|---|---|---|
| Calcd.: | C, 68.85; | H, 7.60; | N, 4.23 |
| Found: | C, 68.66; | H, 7.62; | N, 4.13 |

REFERENCE EXAMPLE 13

2-Acetyl-8-chloro-1,2,3,4-tetrahydoisoquinoline

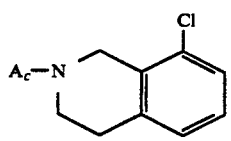

To a mixture of 28.6 g of 8-chloro-1,2,3,4-tetrahydoisoquinoline hydrochloride in 140 ml of dichloromethane was added 140 ml of 1N aqueous NaOH solution and 17.6 g of NaHCO₃. To the solution was added dropwise 14.5 ml of acetic anhydride at 5° C. The mixture was stirred at room temperature for 1 hour. The organic layer was separated and the aqueous layer was extracted with dichloromethane. The combined organic extracts were washed with water, dried over anhydrous sodium sulfate. The solvent was distilled off to give 29.1 g of the title compound as a pale red oil.

| Elemental analysis, for $C_{11}H_{12}ClNO$: | | | |
|---|---|---|---|
| Calcd.: | C, 63.01; | H, 5.77; | N, 6.68. |
| Found: | C, 62.82; | H, 5.86; | N, 6.56. |

REFERENCE EXAMPLE 14

2-Acetyl-5-[3-(1-benzoylpiperidin-4-yl)-1-oxopropyl]-8-chloro-1,2,3,4-tetrahydroisoquinoline

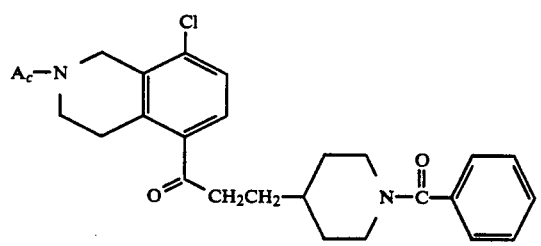

Using 21.0 g of the compound obtained in Reference Example 13, the procedure of Reference Example 11 was followed to give 9.2 g of the title compound as a pale yellow oil.

| Elemental analysis, for $C_{26}H_{29}ClN_2O_3$: | | | |
|---|---|---|---|
| Calcd.: | C, 68.94; | H, 6.45; | N, 6.18. |
| Found: | C, 68.83; | H, 6.52; | N, 6.04. |

EXAMPLE 1

6-[1-Oxo-3-(piperidin-4-yl)propyl]-1,2,3,4-tetrahydroquinoline

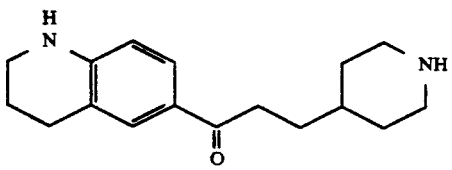

A mixture of 1.3 g of 1-acetyl-6-[3-(1-acetylpiperidin-4-yl)-1-oxopropyl]-1,2,3,4-tetrahydroquinoline obtained in Reference Example 1 and 20 ml of concentrated hydrochloric acid was refluxed for 16 hours. The reaction mixture was then concentrated and the residue was dissolved in water. This solution was washed with ether and the aqueous layer was adjusted to pH about 10 with 10% sodium hydroxide solution and extracted with dichloromethane. The extract was dried over anhydrous sodium sulfate and the solvent was distilled off under reduced pressure to give 0.9 g of a colorless oil.

| Elemental analysis, for $C_{17}H_{24}N_2O$ | | | |
|---|---|---|---|
| Calcd.: | C, 74.96; | H, 8.88; | N, 10.29 |
| Found: | C, 74.87; | H, 8.68; | N. 10.30 |

EXAMPLE 2

6-[1-Oxo-3-[1-(phenylmethyl)piperidin-4-yl]propyl]-1,2,3,4-tetrahydroquinoline dihydrochloride

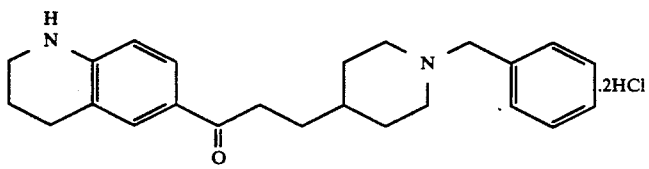

To a mixture of 1.3 g of 6-[1-oxo-3-(piperidin-4-yl)propyl]-1,2,3,4-tetrahydroquinoline, 0.9 g of potassium carbonate and 10 ml of ethanol was added dropwise 2 ml of an ethanolic solution of 0.74 g of benzyl bromide with ice-cooling. The mixture was stirred at room temperature for 2 hours and the solid matter and the solvent were removed. The residue was subjected to column chromatography (eluent; ethyl acetate: methanol=20:1 (v/v)) and the eluate containing the desired compound was distilled to remove the solvent. The residue was treated with 2.4 ml of 4N methanolic hydrochloride to give a solid. This solid was recrystallized from methanol-ether to give 1.55 g of a colorless powder melting at 110° to 125° C. (decomp.)

| Elemental analysis, for $C_{24}H_{30}N_2O \cdot 2HCl$ | | | |
|---|---|---|---|
| Calcd.: | C, 66.20; | H, 7.41; | N, 6.43 |
| Found: | C, 66.00; | H, 7.35; | N, 6.22 |

EXAMPLE 3

1-(Phenylmethyl)-6-[3-[1-(phenylmethyl)piperidin-4-yl]-1-oxopropyl]-1,2,3,4-tetrahydroquinoline dihydrochloride

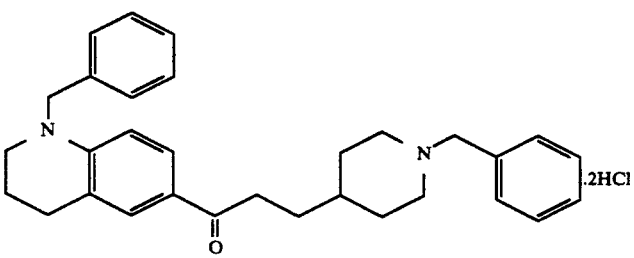

To 5 ml of a solution of 0.5 g to 6-[1-oxo-3-[1-(phenylmethyl)piperidin-4-yl]propyl]-1,2,3,4-tetrahydroquinoline (free base) obtained according to Example 2 in N,N-dimethylformamide was gradually added 40 mg of sodium hydride (oil-free) and the mixture was stirred at room temperature for 1 hour. To this solution was added dropwise 0.22 g of benzyl bromide with ice-cooling and the mixture was stirred at room temperature for 6 hours. The reaction mixture was then treated as in Example 2 and the residue was purified by column chromatography (eluent; ethyl acetate: methanol =20:1 (v/v)). The eluate containing the desired compound was distilled under reduced pressure to remove the solvent and the resulting oil was treated with 0.7 ml of 4N-methanolic hydrochloric acid to give a solid. This solid was recrystallized from ethanol-ether to give 0.28 g of colorless crystals melting at 112° to 117° C. (decomp.).

| Elemental analysis, for $C_{31}H_{36}N_2O \cdot 2HCl$ | | | |
|---|---|---|---|
| Calcd.: | C, 70.85; | H, 7.29; | N, 5.33 |
| Found: | C, 70.81; | H, 7.12; | N, 5.18 |

EXAMPLE 4

1-Methyl-6-[3-[1-(phenylmethyl)piperidin-4-yl]-1-oxo-propyl]-1,2,3,4-tetrahydroquinoline dihydrochloride

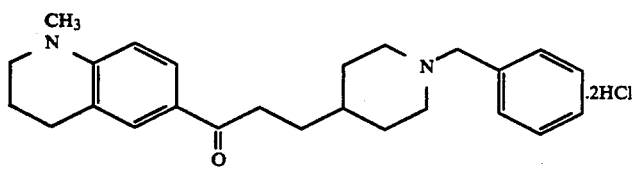

To 3 ml of a solution of 0.2 g of 6-[3-[1-(phenylmethyl)piperidin-4-yl]-1-oxopropyl]-1,2,3,4-tetrahydroquinoline dihydrochloride obtained according to Example 2 in N,N-dimethylformamide was gradually added 37 mg of sodium hydride (oil-free). The mixture was stirred at room temperature for 1 hour, after which 62 mg of methyl iodide was added. The mixture was stirred at room temperature for 6 hours, at the end of which time 15 mg of sodium hydride (oil-fee) and 40 ml of ethyl chlorocarbonate were added in that order. The mixture was stirred for 1 hour and then poured in ice-water and extracted with dichloromethane. The extract was dried over anhydrous sodium sulfate and the solvent was distilled off under reduced pressure. The residue was subjected to column chromatography (eluent; ethyl acetate:methanol=20:1 (v/v)) and the eluate containing the desired compound was distilled under reduced pressure to remove the solvent. The resulting oil was treated with 0.23 ml of 4N-methanolic hydrochloric acid to give 0.1 g of an amorphous powder.

| Elemental analysis, for $C_{25}H_{32}N_2O \cdot 2HCl$ | | | |
|---|---|---|---|
| Calcd.: | C, 66.81; | H, 7.62; | N, 6.23 |
| Found: | C, 66.83; | H, 7.55; | N, 6.09 |

EXAMPLE 5

6-[1-Oxo-3-(piperidin-4-yl)propyl]-1,2,3,4-tetrahydroquinoline (A) and
7-[1-oxo-3-(piperidin-4-yl)propyl]-1,2,3,4-tetrahydroquinoline (B)

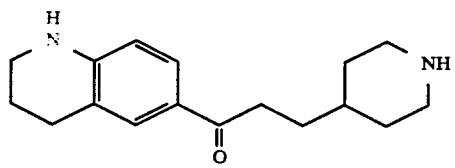

(A)

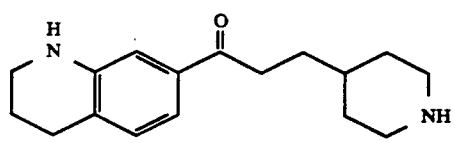

(B)

Using 23 g of the compound according to Reference Example 2, the procedure of Example 1 was followed to give 16.9 g of a mixture of 6-[1-oxo-3-(piperidin-4-yl)propyl]-1,2,3,4-tetrahydroquinoline (A) and 7-[1-oxo-3-(piperidin-4-yl)-propyl]-1,2,3,4-tetrahydroquinoline (B) as a pale yellow oil.

| Elemental analysis, for $C_{17}H_{24}N_2O$ | | | |
|---|---|---|---|
| Calcd.: | C, 74.96; | H, 7.88; | N, 10.29 |
| Found: | C, 74.69; | H, 8.90; | N, 10.22 |

EXAMPLE 6

6-[1-Oxo-3-[1-(phenylmethyl)piperidin-4-yl]propyl]-1,2,3,4-tetrahydroquinoline fumarate (A) and
7-[1-Oxo-3-[1-(phenylmethyl)piperidin-4-yl]propyl]-1,2,3,4-tetrahydroquinoline fumarate (B)

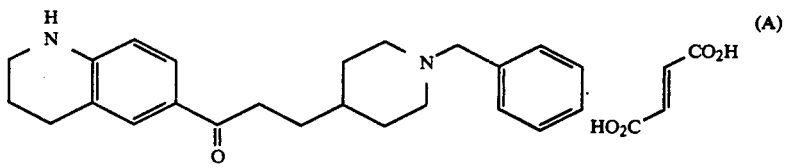

(A)

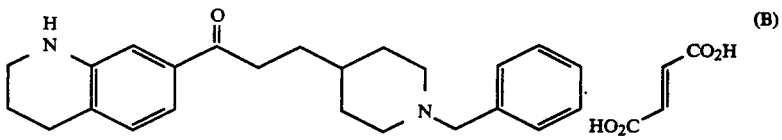

(B)

Using 1.8 g of the compound obtained in Example 5, the procedure of Example 2 was followed to give 1.82 g of the free base of the title compound mixture A and B. The first crop of crystals (0.65 g) from a solution of this mixture in diethyl ether, i.e. 7-[1-oxo-3-[1-(phenylmethyl)piperidin-4-yl]-propyl]-1,2,3,4-tetrahydroquinoline (m.p. 132°-135° C.), was treated with an equivalent of fumaric acid to give 0.69 g of the title fumarate (B) as colorless crystals melting at 175° to 177° C. (decomp.).

| Elemental analysis, for $C_{24}H_{30}N_2O \cdot C_4H_4O_4$ | | | |
|---|---|---|---|
| Calcd.: | C, 70.27; | H, 7.16; | N, 5.85 |
| Found: | C, 70.01; | H, 6.97; | N, 5.98 |

The mother liquor of said diethyl ether solution was also concentrated to recover 0.7 g of 6-[1-oxo-3-[1-(phenylmethyl)piperidin-4-yl]propyl]-1,2,3,4-tetrahydroquinoline as crystals (m.p. 126° to 129° C.). This crop of crystals was treated with an equivalent of fumaric acid to give 0.78 g of the title fumarate (A) as colorless crystals melting at 138° to 142° C. (decomp.)

| Elemental analysis, for $C_{24}H_{30}N_2O \cdot C_4H_4O_4$ | | | |
|---|---|---|---|
| Calcd.: | C, 70.27; | H, 7.16; | N, 5.85 |
| Found: | C, 70.13; | H, 7.13; | N, 5.77 |

EXAMPLE 7

1-Methyl-6-[1-oxo-3-(piperidin-4-yl)propyl]-1,2,3,4-tetrahydroquinoline (A) and
1-methyl-7-[1-oxo-3-(piperidin-4-yl)propyl]-1,2,3,4-tetrahydroquinoline (B)

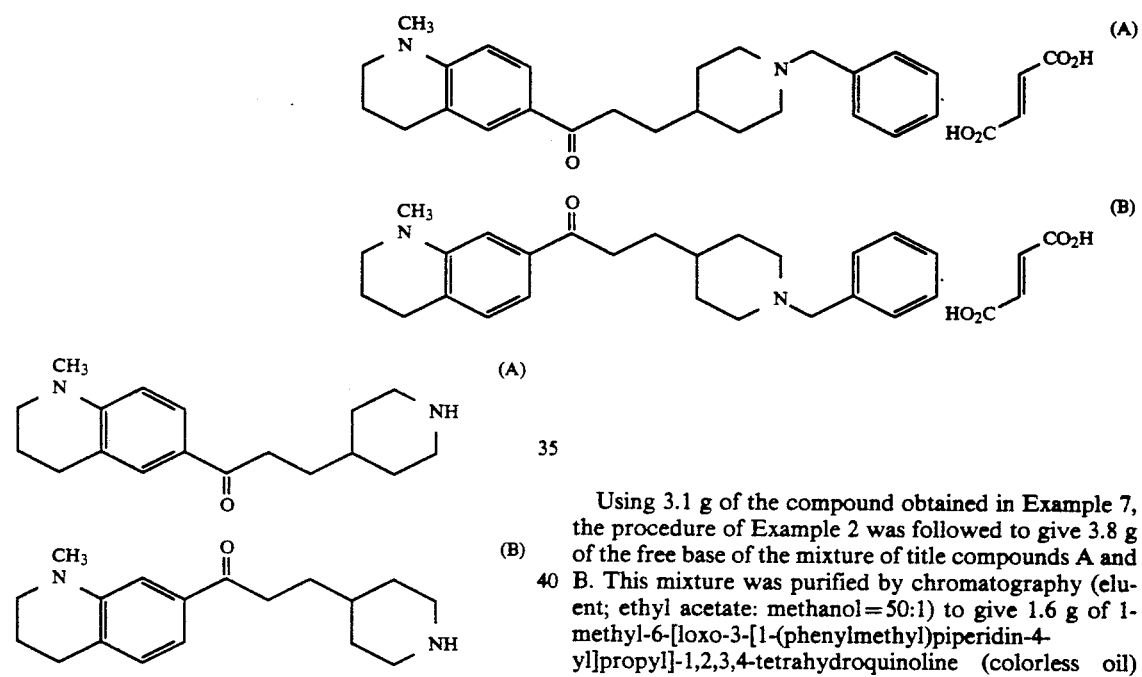

(1) To 40 ml of a solution of 14.2 g of the compound obtained according to Example 5 in dichloromethane was added dropwise 10 ml of a solution of 5.1 g of acetic anhydride in dichloromethane with ice-cooling. The mixture was then stirred at room temperature for 10 minutes, after which it was washed with 10% sodium hydroxide solution and dried over anhydrous sodium sulfate. Finally the solvent was distilled off to give 14.9 g of a mixture of 6-[1-oxo-3-(1-acetylpiperidin-4-yl)propyl]-1,2,3,4-tetrahydroquinoline and 7-[1-oxo-3-(1-acetylpiperidin-4-yl)propyl]-1,2,3,4-tetrahydroquinoline as a colorless oil.

(2) A mixture of 7.1 g of the oil obtained in (1) and 1.6 g of trimethyl phosphate was heated at 190° C. for 2 hours. After cooling to room temperature, 20 ml of dichloromethane as well as aqueous sodium hydroxide solution ($NaOH/H_2O = 1.74$ g/11 ml) was added and the mixture was refluxed for 2 hours. The dichloromethane layer was washed with water and dried over anhydrous sodium sulfate and the solvent was distilled off. The residue was purified by column chromatography (eluent; ethyl acetate: methanol = 30:1) to give 5.5 g of a mixture of 6-[3-(1-acetylpiperidin-4-yl)-1-oxopropyl]-1-methyl-1,2,3,4-tetrahydroquinoline and 7-[3-(1-acetylpiperidin-4-yl)-1-oxopropyl]-1-methyl-1,2,3,4-tetrahydroquinoline as a pale yellow oil. (3) Using 3.9 g of the oil obtained in (2), the procedure of Example 1 was followed to give 3.2 g of a mixture of the title compounds as a pale yellow oil.

| Elemental analysis, for $C_{18}H_{26}N_2O$ | | | |
|---|---|---|---|
| Calcd.: | C, 75.48; | H, 9.15; | N, 9.78 |
| Found: | C, 75.21; | H, 9.06; | N, 9.82 |

EXAMPLE 8

1-Methyl-6-[1-oxo-3-[1-(phenylmethyl)piperidin-4-yl]propyl]-1,2,3,4-tetrahydroquinoline fumarate (A) and
1-methyl-7-[1-oxo-3-[1-(phenylmethyl)piperidin-4-yl]propyl]-1,2,3,4-tetrahydroquinoline fumarate (B)

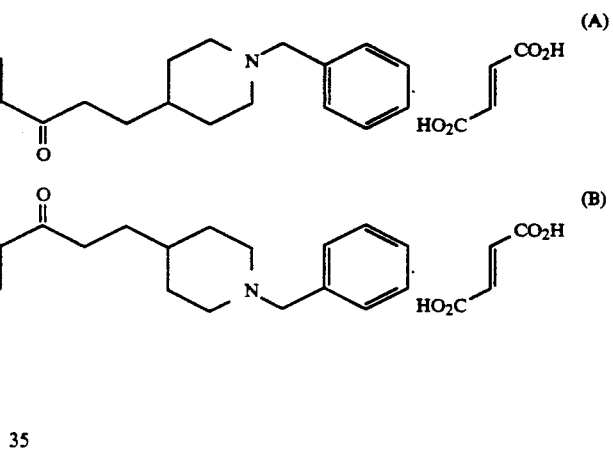

Using 3.1 g of the compound obtained in Example 7, the procedure of Example 2 was followed to give 3.8 g of the free base of the mixture of title compounds A and B. This mixture was purified by chromatography (eluent; ethyl acetate: methanol = 50:1) to give 1.6 g of 1-methyl-6-[1oxo-3-[1-(phenylmethyl)piperidin-4-yl]propyl]-1,2,3,4-tetrahydroquinoline (colorless oil) and 1.7 g of 1methyl-7-[1-oxo-3-[1- (phenylmethyl)piperidin-4-yl]propyl]-1,2,3,4-tetrahydroquinoline (colorless oil).

Then, 1.6 g of 1-methyl-6-[1-oxo-3-[1-(phenylmethyl)piperidin-4-yl]propyl]-1,2,3,4-tetrahydroquinoline was treated with an equivalent of fumaric acid to give 1.7 g of the title fumarate (A) as colorless crystals melting at 170° to 172° C. (decomp.)

| Elemental analysis, for $C_{25}H_{32}N_2O \cdot C_4H_4O_4$ | | | |
|---|---|---|---|
| Calcd.: | C, 70.71; | H, 7.37; | N, 5.69 |
| Found: | C, 70.61; | H, 7.24; | N, 5.63 |

On the other hand, 1.7 g of 1-methyl-7-[1-oxo-3-[1-(phenylmethyl)piperidin-4-yl]propyl]-1,2,3,4-tetrahydroquinoline was treated with an equivalent of fumaric acid to give 1.65 g of the title fumarate (B) as colorless crystals melting at 143° to 144° C. (decomp.)

| Elemental analysis, for $C_{25}H_{32}N_2O \cdot C_4H_4O_4$ | | | |
|---|---|---|---|
| Calcd.: | C, 70.71; | H, 7.37; | N, 5.69 |
| Found: | C, 70.54; | H, 7.09; | N, 5.77 |

EXAMPLE 9

1-(Phenylmethyl)-6-[1-oxo-3-(piperidin-4-yl)propyl]-1,2,3,4-tetrahydroquinoline (A) and
1-(phenylmethyl)-7-[1-oxo-3-(piperidin-4-yl)propyl]-1,2,3,4-tetrahydroquinoline (B)

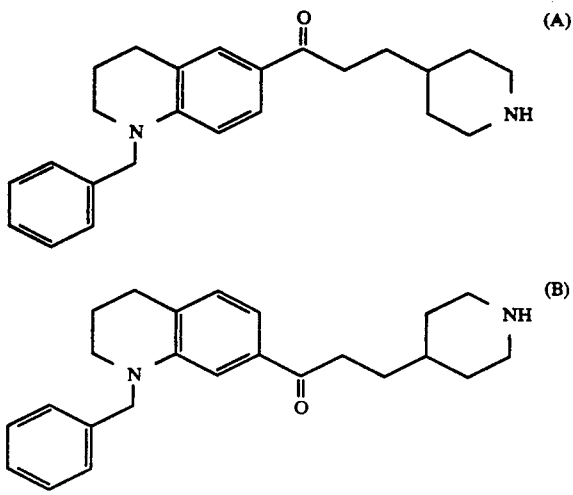

(1) To a mixture of 5.2 g of the compound obtained according to Example 7-(1), 3.0 g of potassium carbonate and 30 ml of ethanol was added dropwise 5 ml of an ethanolic solution of 2.7 g of benzyl bromide with ice-cooling. The mixture was stirred at room temperature for 2 hours and the solid matter and the solvent were removed. The residue was subjected to chromatography (eluent; ethyl acetate: methanol=20:1 (v/v)) to give 3.2 g of 7-[3-(1-acetylpiperidin-4-yl)-1-oxopropyl]-1-(phenylmethyl)-1,2,3,4tetrahydroquinoline (a colorless oil) and 1.8 g of 6-[3-(1-acetylpiperidin- 4-yl)-1-oxopropyl]-1,2,3,4-tetrahydroquinoline.

(2) A mixture of 1.8 g of 6-[3-(1-acetylpiperidin-4-yl)1-oxopropyl]-1,2,3,4-tetrahydroquinoline recovered in (1), 1.03 g of potassium carbonate, 1.96 g of benzyl bromide and 20 ml of ethanol was refluxed for 5 hours and the solid matter and the solvent were removed. The residue was subjected to chromatography (eluent; ethyl acetate: methanol=20:1) to give 2.1 g of 6-[3-(1- acetylpiperidin-4-yl)-1-oxopropyl]-1-(phenylmethyl)-1,2,3,4-tetrahydroquinoline as a colorless oil.

(3) Using 3.15 g of 7-[3-(1-acetylpiperidin-4-yl)-1-oxopropyl]-1-(phenylmethyl)-1,2,3,4-tetrahydroquinoline obtained in (1), the procedure of Example 1 was followed to give 2.8 g of 1-(phenylmethyl)-7-[1-oxo-3-(piperidin-4-yl)propyl]-1,2,3,4-tetrahydroquinoline (B) as a pale yellow oil.

| Elemental analysis, for $C_{24}H_{30}N_2O$ | | | |
|---|---|---|---|
| Calcd.: | C, 79.52; | H, 8.34; | N, 7.73 |
| Found: | C, 79.28; | H, 8.21; | N, 7.59 |

(4) Using 1.9 g of 6-[3-(1-acetylpiperidin-4-yl)-1-oxopropyl]-1-(phenylmethyl)-1,2,3,4-tetrahydroquinoline obtained in (2), the procedure of Example 1 was followed to give 1.63 g of 1-(phenylmethyl)-6-[1-oxo-3-(piperidin-4-yl)propyl]-1,2,3,4-tetrahydroquinoline (A) as a pale yellow oil.

| Elemental analysis, for $C_{24}H_{30}N_2O$ | | | |
|---|---|---|---|
| Calcd.: | C, 79.52; | H, 8.34; | N, 7.73 |
| Found: | C, 79.43; | H, 8.16; | N, 7.48 |

EXAMPLE 10

1-(Phenylmethyl)-6-[1-oxo-3-[1-(phenylmethyl)piperidin-4-yl]propyl]-1,2,3,4-tetrahydroquinoline fumarate

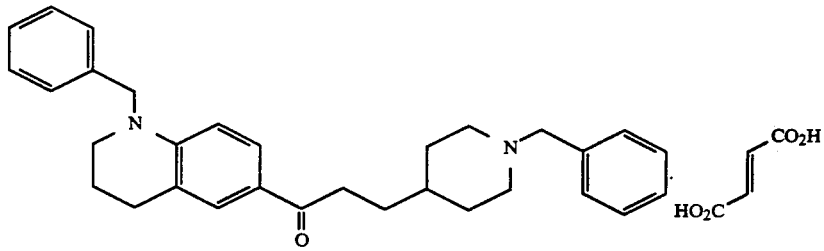

Using 1.5 g of the compound obtained in Example 9-(4), the procedure of Example 2 was followed to give 1.6 g of 1-(phenylmethyl)-6-[1-oxo-3-[1-(phenylmethyl)-piperidin-4-yl]propyl]-1,2,3,4-tetrahydroquinoline (free base) as a colorless oil. This oil (1.6 g) was treated with an equivalent of fumaric acid to give 1.7 g of the title fumarate as colorless crystals melting at 178° to 181° C. (decomp.)

| Elemental analysis, for $C_{31}H_{36}N_2O \cdot C_4H_4O_4$ | | | |
|---|---|---|---|
| Calcd.: | C, 73.92; | H, 7.09; | N, 4.93 |
| Found: | C, 73.64; | H, 7.22; | N, 4.84 |

EXAMPLE 11

1-(Phenylmethyl)-7-[1-oxo-3-[1-(phenylmethyl)piperidin-4-yl]propyl]-1,2,3,4-tetrahydroquinoline fumarate

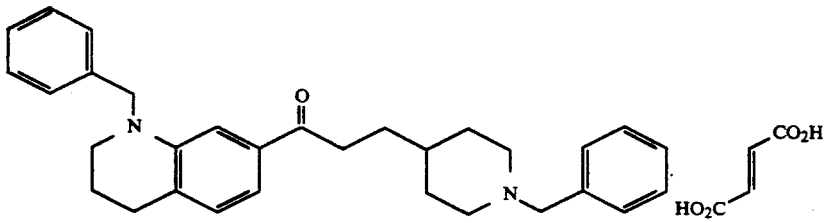

Using 2.75 g of the compound obtained in Example 9-(3), the procedure of Example 2 was followed to give 2.95 g of 1-(phenylmethyl)-7-[1-oxo-3-[1-(phenylmethyl)piperidin-4-yl]propyl]-1,2,3,4-tetrahydroquinoline (free base) as a colorless oil. This oil (2.95 g) was treated with an equivalent of fumaric acid to give 3.1 g of the title fumarate as colorless crystals melting at 180° to 182° C. (decomp.).

| Elemental analysis, for $C_{31}H_{36}N_2O \cdot C_4H_4O_4$ |||
|---|---|---|
| Calcd.: | C, 73.92; H, 7.09; | N, 4.93 |
| Found: | C, 73.72; H, 7.02; | N, 4.86 |

EXAMPLE 12

2,3-Dihydro-5-[1-oxo-3-(piperidin-4-yl)propyl]-1H-indole

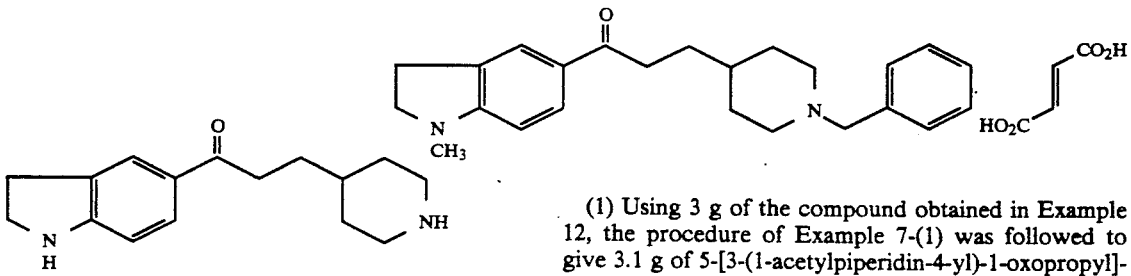

Using 10 g of the compound obtained in Reference Example 3, the procedure of Example 1 was followed and the resulting solid product was recrystallized from dichloromethane - diethyl ether to give 7.08 g of pale yellow crystals melting at 137° to 139° C.

| Elemental analysis, for $C_{16}H_{22}N_2O$ |||
|---|---|---|
| Calcd.: | C, 74.38; | H, 8.58; N, 10.84 |

| Elemental analysis, for $C_{16}H_{22}N_2O$ |||
|---|---|---|
| Found: | C, 74.11; | H, 8.75; N, 10.67 |

EXAMPLE 13

2,3-Dihydro-5-[1-oxo-3-[1-(phenylmethyl)piperidin-4-yl]propyl]-1H-indole fumarate

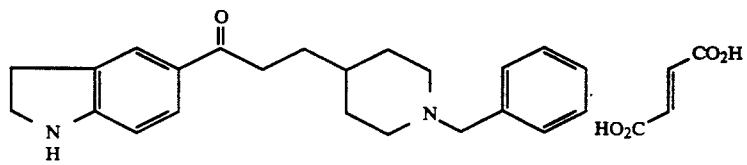

Using 2 g of the compound obtained in Example 12, the procedure of Example 2 was followed to give 2.3 g of the free base of the title compound as colorless crystals melting at 81° to 82° C. The crystals (2.3 g) were then treated with an equivalent of fumaric acid to give 2.6 g of the title fumarate as colorless crystals melting at 150° to 153° C. (decomp.).

| Elemental analysis, for $C_{23}H_{28}N_2O \cdot C_4H_4O_4$ |||
|---|---|---|
| Calcd.: | C, 69.81; H, 6.94; | N, 6.03 |
| Found: | C, 69.68; H, 6.71; | N, 5.93 |

EXAMPLE 14

2,3-Dihydro-1-methyl-5-[1-oxo-3-[1-(phenylmethyl)piperidin-4-yl]propyl]-1H-indole fumarate (1) Using 3 g of the compound obtained in Example 12, the procedure of Example 7-(1) was followed to give 3.1 g of 5-[3-(1-acetylpiperidin-4-yl)-1-oxopropyl]-2,3-dihydro-1H-indole as colorless crystals melting at 145° to 146° C.

| Elemental analysis, for $C_{18}H_{24}N_2O_2$ |||
|---|---|---|
| Calcd.: | C, 71.97; H, 8.05; | N, 9.33 |
| Found: | C, 71.92; H, 7.94; | N, 9.11 |

(2) Using 1.5 g of the compound prepared in (1), the procedure of Example 7-(2) was followed to give 1.25 g of 5-[3-(1-acetylpiperidin-4-yl)-1-oxopropyl]-2,3-dihydro-1-methyl-1H-indole as a colorless oil.

(3) Using 1.0 g of the compound obtained in (2), the procedure of Example 1 was followed to give 0.83 g of 2,3-dihydro-1-methyl-5-[1-oxo-3-(piperidin-4-yl)propyl]-1Hindole as a pale yellow oil.

| Elemental analysis, for $C_{17}H_{24}N_2O$ | | | |
|---|---|---|---|
| Calcd.: | C, 74.96; | H, 8.88; | N, 10.29 |
| Found: | C, 74.69; | H, 8.79; | N, 10.33 |

(4) Using 0.53 g of the compound obtained in (3), the procedure of Example 2 was followed to give 0.51 g of the free base of the title compound as a colorless oil. This oil (0.51 g) was treated with an equivalent of fumaric acid to give 0.57 g of the title fumarate as colorless crystals melting at 147 to 151° C. (decomp.).

| Elemental analysis, for $C_{24}H_{30}N_2O.C_4H_4O_4$ | | | |
|---|---|---|---|
| Calcd.: | C, 70.27; | H, 7.16; | N, 5.85 |
| Found: | C, 70.06; | H, 7.09; | N, 5.80 |

EXAMPLE 15

2,3-Dihydro-5-[1-oxo-3-[1-(phenylmethyl)piperidin-4-yl]propyl]-1-(phenylmethyl)-1H-indole fumarate

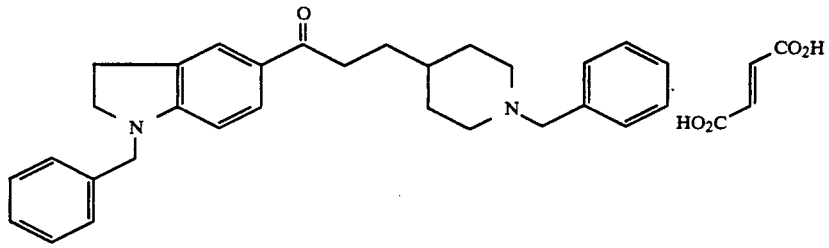

(1) Using 0.65 g of the compound obtained in Example 14-(1), the procedure of Example 9-(2) was followed to give 0.77 g of 5-[3-(1-acetylpiperidin-4-yl)-1-oxopropyl]-2,3-dihydro-1-(phenylmethyl)-1H-indole as a colorless oil.

(2) Using 0.76 g of the compound obtained in (1), the procedure of Example 1 was followed to give 0.65 g of 2,3-dihydro-5-[1-oxo-3-(piperidin-4-yl)propyl]-1-(phenylmethyl)-1H-indole as a yellow oil.

| Elemental analysis, for $C_{23}H_{28}N_2O$ | | | |
|---|---|---|---|
| Calcd.: | C, 79.27; | H, 8.10; | N, 8.04 |
| Found: | C, 79.03; | H, 8.05; | N, 8.13 |

(3) Using 0.64 g of the compound obtained in (2), the procedure of Example 2 was followed to give 0.66 g of the free base of the title compound as a colorless oil. This oil (0.66 g) was treated with an equivalent of fumaric acid to give 0.75 g of the title fumarate as colorless crystals melting at 153° to 156° C. (decomp.).

| Elemental analysis, for $C_{30}H_{34}N_2O.C_4H_4O_4$ | | | |
|---|---|---|---|
| Calcd.: | C, 73.62; | H, 6.91; | N, 5.05 |
| Found: | C, 73.65; | H, 6.80; | N, 5.00 |

EXAMPLE 16

1-Acetyl-6-[1-oxo-3-[1-(phenylmethyl)piperidin-4-yl]propyl]-1,2,3,4-tetrahydroquinoline fumarate

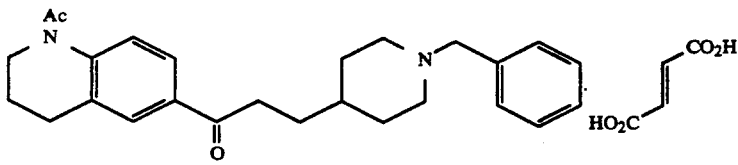

In 10 ml of dichloromethane were dissolved 0.5 g of 6-[1-oxo-3-[1-(phenylmethyl)piperidin-4-yl]propyl]-1,2,3,4-tetrahydroquinoline (free base), 0.28 g of acetic anhydride and 0.22 g of pyridine and the solution was refluxed for 2 hours. The solvent and the excess reagents were distilled off under reduced pressure and the residue was dissolved in dichloromethane. The solution was washed with 10% sodium hydroxide and dried over anhydrous sodium sulfate and the solvent was distilled off. This residue was purified by chromatography (eluent; ethyl acetate: ethanol=20:1) to give 0.45 g of the free base of the title compound as a colorless oil. This acid to give 0.53 g of the title fumarate as an amorphous powder.

| Elemental analysis, for $C_{26}H_{32}N_2O_2.C_4H_4O_4$ | | | |
|---|---|---|---|
| Calcd.: | C, 69.21; | H, 6.97; | N, 5.38 |
| Found: | C, 69.23; | H, 6.87; | N, 5.40 |

EXAMPLE 17

8-[1-Oxo-3-(piperidin-4-yl)propyl]-2,3,4,5-tetrahydro-1H-1-benzazepine

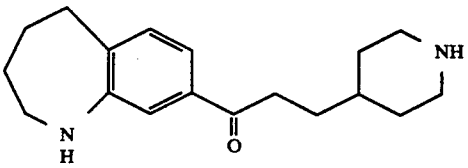

Using 6.5 g of the compound A obtained in Reference Example 4, the procedure of Example 1 was followed to give a viscous oil and this oil was crystallized from hexane to give 4.6 g of pale yellow crystals melting at 104° to 107° C.

| Elemental analysis, for $C_{18}H_{26}N_2O$ | | | |
|---|---|---|---|
| Calcd.: | C, 75.48; | H, 9.15; | N, 9.78 |
| Found: | C, 75.24; | H, 9.09; | N, 9.66 |

EXAMPLE 18

Using the compounds obtained in Reference Examples 4, 6 and 7, the procedure of Example 1 was followed to give compounds as oils as follows.

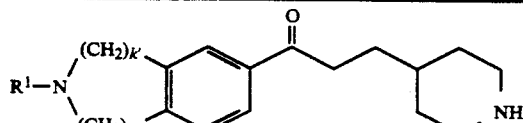

| Compound No. | k' | m' | $R^1$ | Molecular formula | Analysis Calcd. (Found) | | |
|---|---|---|---|---|---|---|---|
| | | | | | C | H | N |
| 1 | 2 | 0 | $C_2H_5$ | $C_{18}H_{26}N_2O$ | 75.48 (75.22 | 9.15 9.17 | 9.78 9.69) |
| 2 | 2 | 0 | $C_3H_7$ | $C_{19}H_{28}N_2O$ | 75.96 (75.78 | 9.39 9.25 | 9.32 9.12) |

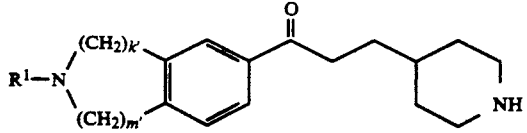

| Compound No. | k' | m' | $R^1$ | Molecular formula | Analysis Calcd. (Found) | | |
|---|---|---|---|---|---|---|---|
| | | | | | C | H | N |
| 3 | 2 | 0 | $C_4H_9$ | $C_{20}H_{30}N_2O$ | 76.39 (76.20 | 9.62 9.52 | 8.91 8.78) |
| 4 | 2 | 0 | $C_5H_{11}$ | $C_{21}H_{32}N_2O$ | 76.78 (76.69 | 9.82 9.81 | 8.53 8.55) |
| 5 | 2 | 0 | $CH_2CH_2Ph$ | $C_{24}H_{30}N_2O$ | 79.52 (79.46 | 8.34 8.11 | 7.73 7.59) |
| 6 | 0 | 4 | $CH_3$ | $C_{19}H_{28}N_2O$ | 75.96 (75.84 | 9.39 9.29 | 9.32 9.33) |
| 7 | 0 | 4 | $C_2H_5$ | $C_{20}H_{30}N_2O$ | 76.39 (76.21 | 9.62 9.51 | 8.91 8.75) |
| 8 | 0 | 4 | $C_3H_7$ | $C_{21}H_{32}N_2O$ | 76.78 (76.53 | 9.82 9.74 | 8.53 8.41) |
| 9 | 4 | 0 | H | $C_{18}H_{26}N_2O$ | 75.48 (75.32 | 9.15 9.09 | 9.78 9.64) |

EXAMPLE 19

Using the compound obtained in Examples 12, 17 or 18, the procedure of Example 13 was followed to give the compounds as follows.

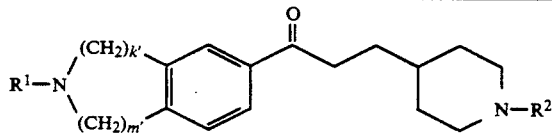

| Compound No. | k' | m' | $R^1$ | $R^2$ | m.p. (°C.) | Molecular formula | Analysis Calcd. (Found) | | |
|---|---|---|---|---|---|---|---|---|---|
| | | | | | | | C | H | N |
| 1 | 2 | 0 | H | $CH_2$-[2-$OCH_3$-phenyl] | 169–171 (decomp.) | $C_{24}H_{30}N_2O_2 \cdot C_4H_4O_4$* | 68.00 (67.91 | 6.93 6.93 | 5.66 5.42) |
| 2 | 2 | 0 | H | $CH_2$-[3-$OCH_3$-phenyl] | 151–153 (decomp.) | $C_{24}H_{30}N_2O_2 \cdot C_4H_4O_4$* | 68.00 (67.71 | 6.93 6.77 | 5.66 5.56) |
| 3 | 2 | 0 | H | $CH_2$-[4-$OCH_3$-phenyl] | 101–103 | $C_{24}H_{30}N_2O_2 \cdot C_4H_4O_4$* | 68.00 (67.79 | 6.93 6.92 | 5.66 5.61) |
| 4 | 2 | 0 | H | $CH_2$-[2-Cl-phenyl] | 159–161 | $C_{23}H_{27}ClN_2O \cdot C_4H_4O_4$* | 64.99 (64.85 | 6.26 6.27 | 5.61 5.54) |
| 5 | 2 | 0 | H | $CH_2$-[3-Cl-phenyl] | 157–159 | $C_{23}H_{27}ClN_2O \cdot C_4H_4O_4$* | 64.99 (64.91 | 6.26 6.31 | 5.61 5.57) |

-continued

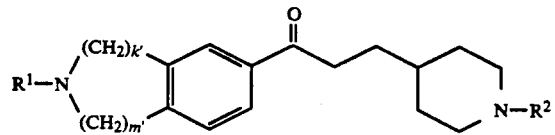

| Compound No. | k' | m' | R¹ | R² | m.p. (°C.) | Molecular formula | Analysis Calcd. (Found) C | H | N |
|---|---|---|---|---|---|---|---|---|---|
| 6 | 2 | 0 | H | $CH_2$-C₆H₄-Cl (4-Cl) | 146-148 | $C_{23}H_{27}ClN_2O \cdot C_4H_4O_4$* | 64.99 (64.83 | 6.26 6.19 | 5.61 5.62) |
| 7 | 2 | 0 | H | $CH_2$-C₆H₄-CH₃ (3-CH₃) | 169-163 (decomp.) | $C_{24}H_{30}N_2O \cdot C_4H_4O_4$* | 70.27 (70.04 | 7.16 7.30 | 5.85 5.74) |
| 8 | 2 | 0 | H | $CH_2$-C₆H₄-F (3-F) | 163-165 (decomp.) | $C_{23}H_{27}FN_2O \cdot C_4H_4O_4$* | 67.21 (67.03 | 6.48 6.50 | 5.81 5.76) |
| 9 | 2 | 0 | H | $CH_2$-C₆H₄-$NO_2$ (3-$NO_2$) | 114-116 | $C_{23}H_{27}N_3O_3$ | 70.21 (70.06 | 6.92 6.96 | 10.68 10.47) |
| 10 | 2 | 0 | H | $CH_2CH_2Ph$ | 143-145 | $C_{24}H_{30}N_2O \cdot C_4H_4O_4$* | 70.27 (69.98 | 7.16 7.22 | 5.85 5.74) |
| 11 | 2 | 0 | $C_2H_5$ | $CH_2Ph$ | 155-157 | $C_{25}H_{32}N_2O \cdot C_4H_4O_4$* | 70.71 (70.55 | 7.37 7.43 | 5.69 5.54) |
| 12 | 2 | 0 | $C_3H_7$ | $CH_2Ph$ | 91-93 | $C_{26}H_{34}N_2O \cdot C_4H_4O_4$* | 71.12 (71.00 | 7.56 7.62 | 5.53 5.33) |
| 13 | 2 | 0 | $C_4H_9$ | $CH_2Ph$ | 127-129 | $C_{27}H_{36}N_2O \cdot C_4H_4O_4$* | 71.51 (71.29 | 7.74 7.86 | 5.38 5.22) |
| 14 | 2 | 0 | $C_5H_{11}$ | $CH_2Ph$ | 140-142 | $C_{28}H_{38}N_2O \cdot C_4H_4O_4$* | 71.88 (71.71 | 7.92 8.13 | 5.24 5.12) |
| 15 | 2 | 0 | $CH_2CH_2Ph$ | $CH_2Ph$ | Amorphous solid | $C_{31}H_{38}N_2O \cdot C_4H_4O_4$* | 73.92 (73.69 | 7.09 7.13 | 4.93 4.91) |
| 16 | 0 | 4 | H | $CH_2Ph$ | 173-174 | $C_{25}H_{32}N_2O \cdot C_4H_4O_4$* | 70.71 (70.54 | 7.37 7.47 | 5.69 5.57) |
| 17 | 0 | 4 | $CH_3$ | $CH_2Ph$ | 100-102 | $C_{26}H_{34}N_2O \cdot C_4H_4O_4$* | 71.12 (70.97 | 7.56 7.55 | 5.53 5.48) |
| 18 | 0 | 4 | $C_2H_5$ | $CH_2Ph$ | 84-87 | $C_{27}H_{36}N_2O \cdot C_4H_4O_4$* | 71.51 (71.38 | 7.74 7.86 | 5.38 5.21) |
| 19 | 0 | 4 | $C_3H_7$ | $CH_2Ph$ | 98-100 | $C_{28}H_{38}N_2O \cdot C_4H_4O_4$* | 71.88 (71.63 | 7.92 7.99 | 5.24 5.16) |
| 20 | 4 | 0 | H | $CH_2Ph$ | 117-120 | $C_{25}H_{32}N_2O \cdot C_4H_4O_4$* | 70.71 (70.59 | 7.37 7.48 | 5.69 5.43) |
| 21 | 0 | 4 | H | $CH_2$-C₆H₄-F | 156-160 | $C_{25}H_{31}N_2FO \cdot C_4H_4O_4$* | 68.22 (67.88 | 6.91 6.95 | 5.49 5.27) |
| 22 | 0 | 4 | H | $CH_2$-C₆H₄-Me | 152-158 | $C_{26}H_{34}N_2O \cdot C_4H_4O_4$* | 71.12 (71.15 | 7.56 7.76 | 5.53 5.29) |

-continued

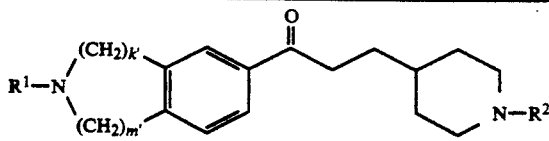

| Compound No. | k' | m' | R¹ | R² | m.p. (°C.) | Molecular formula | Analysis Calcd. (Found) C | H | N |
|---|---|---|---|---|---|---|---|---|---|
| 23 | 0 | 4 | H | CH₂-C₆H₄-Cl (3-Cl) | 138–144 | $C_{25}H_{31}N_2ClO \cdot C_4H_4O_4$* | 66.09 (66.00 | 6.69 6.92 | 5.32 4.98) |
| 24 | 0 | 4 | H | CH₂-C₆H₄-F (2-F) | 165–170 | $C_{25}H_{31}N_2FO \cdot C_4H_4O_4$* | 68.22 (68.04 | 6.91 6.92 | 5.49 5.24) |
| 25 | 0 | 4 | H | CH₂-C₆H₄-F (4-F) | 158–163 | $C_{25}H_{31}N_2FO \cdot C_4H_4O_4$* | 68.22 (67.99) | 6.91 (6.82) | 5.49 5.39) |
| 26 | 0 | 4 | H | CH₂-C₆H₄-OCH₃ (3-OMe) | 126–128 | $C_{26}H_{34}N_2O_2 \cdot C_4H_4O_4$* | 68.94 (68.80 | 7.33 7.51 | 5.36 5.23 |
| 27 | 0 | 4 | H | CH₂-C₆H₄-OCH₃ (2-OMe) | 116–117 | $C_{26}H_{34}N_2O_2 \cdot C_4H_4O_4$* | 68.94 (68.83 | 7.33 7.43 | 5.36 5.24 |
| 28 | 0 | 4 | H | CH₂-C₆H₄-OCH₃ (4-OMe) | 168–170 | $C_{26}H_{34}N_2O_2 \cdot C_4H_4O_4$* | 68.94 (68.78 | 7.33 7.44 | 5.36 4.84) |
| 29 | 0 | 4 | H | CH₂-C₆H₄-NO₂ (3-NO₂) | 161–163 | $C_{25}H_{31}N_3O_3 \cdot C_4H_4O_4$* | 64.79 (64.81 | 6.56 6.40 | 7.82 7.66) |
| 30 | 2 | 0 | H | CH₂-C₆H₄-F (2-F) | 144–147 | $C_{23}H_{27}FN_2O \cdot C_4H_4O_4$* | 67.21 (67.13 | 6.48 6.44 | 5.81 5.73) |
| 31 | 2 | 0 | H | CH₂-C₆H₄-F (4-F) | 124–127 | $C_{23}H_{27}FN_2O \cdot C_4H_4O_4$* | 67.21 (67.09 | 6.48 6.51 | 5.81 5.69) |
| 32 | 0 | 4 | CH₂Ph | CH₂Ph | 171–173 | $C_{32}H_{38}N_2O \cdot C_4H_4O_4$* | 74.20 (74.08 | 7.26 7.33 | 4.81 4.85) |

*$C_4H_4O_4$ means the fumarate.
Ph means phenyl.
Me means methyl.
Ac means acetyl.

EXAMPLE 20

2,3-Dihydro-5-[1-oxo-3-(piperidin-4-yl)propylbenzofuran hydrochloride

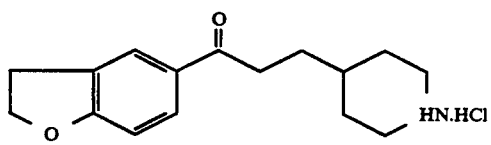

To 30 ml of concentrated hydrochloric acid was added 5.00 g of 5-[3-(1-acetylpiperidin-4-yl)-1-oxopropyl]-2,3-dihydrobenzofuran, and the mixture was refluxed for 14 hours. The reaction mixture was left standing for cooling and then made basic with a dilute aqueous solution of sodium hydroxide, followed by extraction with methylene chloride. Organic layers were combined and dried over anhydrous sodium sulfate, then the solvent was distilled off to leave 4.31 g (100%) of 2,3-dihydro-5-[1-oxo-3-(piperidin-4-yl)propyl]benzofuran (4). The solid matter thus obtained was dissolved in methanol, treated with hydrogen chloride and recrystallized from methanol—ethyl acetate to give colorless needles, m.p. 203°-205° C. (decomp.)

| Elemental Analysis, for $C_{16}H_{21}NO_2$.HCl | | | |
|---|---|---|---|
| Calcd.: | C, 64.97; | H, 7.50; | N, 4.74 |
| Found: | C, 64.76; | H, 7.64; | N, 4.54 |

EXAMPLE 21

2,3-Dihydro-5-[1-oxo-3-[1-(phenylmethyl)piperidin-4-yl]propyl]benzofuran hydrochloride

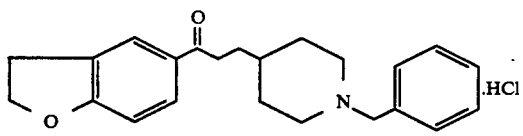

To 30 ml of a mixture solution of tetrahydrofuran and ethanol (50/50=v/v) was added 1.52 g of 2,3-dihydro-5-[1-oxo-3-(piperidin-4-yl)propyl]benzofuran, to which was then added 1.06 g of potassium carbonate. The resultant mixture was ice-cooled and there was added dropwise an ethanol solution (5 ml) of 0.96 g of benzyl bromide. The mixture was stirred for 22 hours at room temperatures, then the solvent was distilled off. To the residue was added water, which was extracted with methylene chloride. Organic layers were combined and dried over anhydrous sodium sulfate, then the solvent was distilled off. The residue was purified by means of a silica gel column chromatography (ethyl acetate) to give 1.13 g (55%) of 2,3-dihydro-5-[1-oxo-3-[1-(phenylmethyl)piperidin-4-yl]propylbenzofuran. The product was dissolved in methanol, treated with hydrogen chloride, then recrystallized from ethanol—ethyl acetate to give colorless needles (¼ hydrate), m.p. 143°-144° C.

| Elemental Analysis for $C_{23}H_{27}NO_2$.HCl.1/4H$_2$O: | | | |
|---|---|---|---|
| Calcd. | C, 70.75; | H, 7.36; | N, 3.59 |
| Found. | C, 70.49; | H, 7.26; | N, 3.62 |

EXAMPLE 22

7-[1-Oxo-3-[1-(phenylmethyl)piperidin-4-yl]propyl]-2,3,4,5-tetrahydro-1H-3-benzazepine dihydrochloride

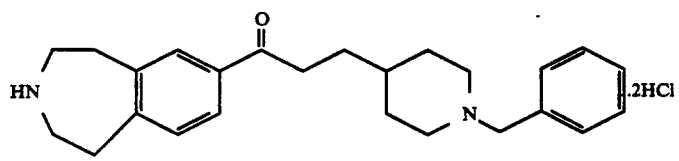

Under nitrogen atomosphere, 0.48 g (1.1 mmol.) of 3-methoxycarbonyl-7-[3-(1-benzoylpiperidin-4-yl)-1-yl)-oxopropyl]-2,3,4,5-tetrahydro-1H-3-benzazepine obtained in Reference Example 11 was dissolved in 5 ml of dry chloroform. To the solution was added 0.3 ml (2.1 mmol.) of iodotrimethylsilane. The mixture was stirred for 2.5 hours at 50° C. The reaction mixture was left standing for cooling, to which was added 0.4 ml (10 mmol.) of methanol. To the resultant mixture were added a dilute aqueous solution of sodium hydroxide and an aqueous solution of sodium thiosulfate, followed by extraction with dichloromethane. The extract was dried over anhydrous sodium sulfate, then the solvent was distilled off. The residue was dissolved in 15 ml of dry tetrahydrofuran. To the solution was added 0.13 g (3.4 mmol.) of lithium aluminum hydride, and the mixture was refluxed for 5 hours. To the reaction mixture was added water, then the solid matter was filtered off. The filtrate was dried over anhydrous sodium sulfate, then the solvent was distilled off. The residue was dissolved in methanol and treated with hydrogen chloride and the solvent was distilled off to give a hydrochloride. To the hydrochloride there was further added a mixture of 0.3 g (3 mmol.) of chromic acid, 0.3 ml of concentrated sulfuric acid and 10 ml of water-acetone (1/1=v/v). The resultant mixture was stirred for 24 hours at room temperatures. The reaction mixture was poured into water and it was made basic with a dilute aqueous solution of sodium hydroxide, followed by extraction with dichloromethane. The extract was dried over anhydrous sodium sulfate, then the solvent was distilled off. The residue was purified by means of an alumina column chromatography to give 0.31 g (76%) of 7-[1-oxo-3-[1-phenylmethyl)piperidin-4-yl]propyl]-2,3,4,5-tetrahydro-1H-3-benzazepine. The product was dissolved in methanol and treated with 3 N methanolic hydrochloric acid to give dihydrochloride as an amorphous powder.

| Elemental Analysis, for $C_{25}H_{32}N_2O$.2HCl.2.5H$_2$O: | | | |
|---|---|---|---|
| Calcd.: | C, 60.72; | H, 7.95; | N, 5.66 |
| Found: | C, 60.85; | H, 8.24; | N, 5.51 |

EXAMPLE 23

3-Methyl-7-[1-oxo-3-[1-(phenylmethyl)piperidin-4-yl]-propyl-2,3,4,5-tetrahydro-1H-3-benzazepine dihydrochloride

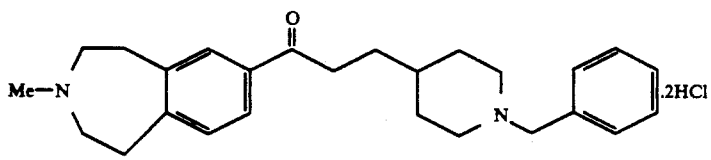

In 40 ml of toluene was dissolved 1.17 g (2.6 mmol.) of 3-methoxycarbonyl-7-[3-(1-benzoylpiperidin-4-yl)-1-oxopropyl]-2,3,4,5-tetrahydro-1H-3-benzazepine. To the solution were added 7 ml of ethylene glycol and 10 mg of p-toluenesulfonic acid, and the mixture was refluxed for 2.5 hours. To the reaction mixture was added a saturated aqueous solution of sodium hydrogen carbonate, which was subjected to extraction with diethyl ether. The extract was dried over anhydrous sodium sulfate, then the solvent was distilled off. The residue was purified by means of a silica gel column chromatography to give 1.22 g (94%) of 7-[2-[2-(1-benzoylpiperidin-4-yl)ethyl]-1,3-dioxoran-2-yl]-3-methoxycarbonyl-2,3,4,5-tetrahydro-1H-3-benzazepine. 1.03 g (2.1 mmol.) of the compound obtained above was dissolved in 15 ml of dry tetrahydrofuran, to which was added 0.25 g (6.5 mmol.) of lithium aluminum hydride. The reaction mixture was refluxed for 3 hours and there was added water, followed by filtration. The filtrate was dried over anhydrous sodium sulfate, then the solvent was distilled off. The residue was dissolved in tetrahydrofuran, to which was added 5.6 ml of 1N-HCl, and the mixture was stirred for 14.5 hours at room temperature. The reaction mixture was made basic with a dilute aqueous solution of sodium hydroxide, followed by extraction with dichloromethane. The extract solution was dried over anhydrous sodium sulfate, then the solvent was distilled off. The residue was dissolved in methanol and the solution was treated with hydrogen chloride to give a dihydrochloride, which was then recrystallized from ethanol—ethyl acetate to give 0.65 g (67%) of colorless needles, m.p. 190°–193° C.

| Elemental Analysis for $C_{26}H_{34}N_2O \cdot 2HCl \cdot H_2O$: | | | |
|---|---|---|---|
| Calcd.: | C, 64.86; | H, 7.95; | N, 5.82 |
| Found: | C, 64.78; | H, 7.90; | N, 5.78 |

EXAMPLE 24

2,3-Dihydro-6-[1-oxo-3-(piperidin-4-yl)propyl]-1H-indole

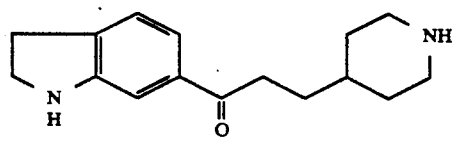

(1) To a mixture of 25 g of 2,3-dihydro-1-trifluoroacetyl-indole, 25 g of 3-(1-acetylpiperidin-4-indole)propionic acid chloride and 120 ml of carbon disulfide was added 56 g of anhydrous aluminum chloride at room temperatures, then the mixture was refluxed for 30 hours. The reaction mixture was treated in a manner like that of Reference Example 1-(3) to give 9.0 g of a mixture of 6-[3-(1-acetylpiperidin-4-yl)-1-oxopropyl]-2,3-dihydro-1-trifluoroacetyl-1H-indole and 5-[3-(1-acetylpiperidin-4-yl)-1-oxopropyl]-2,3-dihydro-1-trifluoroacetyl-1H-indole as a pale yellow oily product.

(2) The oily product obtained in (1) was subjected to a reaction like that of Example 1 to give 2,3-dihydro-6-1-oxo-3-(piperidin-4-yl)propyl]-1H-indole dihydrochloride. A mixture of this dihydrochloride and 2,3-dihydro-5-1-oxo-3-(piperidin-4-yl)propyl]-1H-indole dihydrochloride was subjected to recrystallization twice from methanol—ethyl acetate to give 2.5 g of dihydrochloride of the above-titled compound as colorless powder, m.p. 146°–148° C. The powdery compound thus obtained was dissolved in water, whose pH was adjusted to about 10 with a 10% sodium hydroxide solution, which was subjected to extraction with dichloromethane. The extract solution was dried over anhydrous sodium sulfate, and the solvent was distilled off under reduced pressure to give 1.8 g of the above-titled compound as a pale yellow oily product.

| Elemental Analysis, for $C_{16}H_{22}N_2O$: | | | |
|---|---|---|---|
| Calcd.: | C, 74.38; | H, 8.58; | N, 10.84 |
| Found: | C, 74.32; | H, 8.66; | N, 10.74 |

EXAMPLE 25

2,3-Dihydro-6-[1-oxo-3-[1-(phenylmethyl)piperidin-4-yl]propyl]-1H-indole fumarate

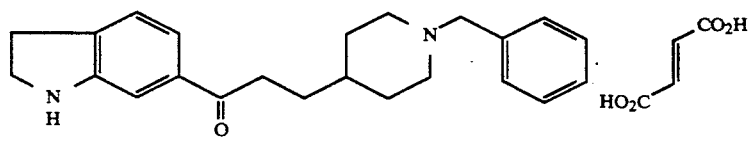

Using 0.5 g of the compound obtained in Example 24, the procedure of Example 13 was followed to give 0.55 g of the title compound as colorless crystals, m.p. 157°-158° C.

| Elemental Analysis for $C_{23}H_{28}N_2O \cdot C_4H_4O_4$: | | | |
|---|---|---|---|
| Calcd.: | C, 69.81; | H, 6.94; | N, 6.03 |
| Found: | C, 69.65; | H, 6.87; | N, 5.76 |

EXAMPLE 26

9-[1-Oxo-3-(piperidin-4-yl)propyl]-1,2,3,4,5,6-hexahydro-1-benzazocine

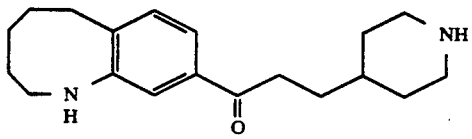

Using 1-ethoxycarbonyl-1,2,3,4,5,6-hexahydro-1-benzazocine, the procedure of Reference Example 2-(2) was followed to give a residue. The residue was subjected to similar reaction to Example 1 to give the title compound as a pale yellow oily product.

| Elemental Analysis, for $C_{19}H_{28}N_2O$: | | | |
|---|---|---|---|
| Calcd.: | C, 75.95; | H, 9.39; | N, 9.33 |
| Found: | C, 75.73; | H, 9.38; | N, 9.10 |

EXAMPLE 27

9-[1-Oxo-3-[1-(phenylmethyl)piperidin-4-yl]propyl]-1,2,3,4,5,6-hexahydro-1-benzazocine fumarate

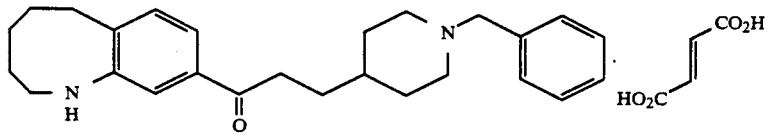

Using 9-[1-oxo-3-(piperidin-4-yl)propyl]-1,2,3,4,5,6-hexahydro-1-benzazocine, the procedure of Example 13 was followed to give the title compound as colorless crystals.

| Elemental Analysis, for $C_{26}H_{34}N_2O \cdot C_4H_4O_4$: | | | |
|---|---|---|---|
| Calcd.: | C, 71.12; | H, 7.56; | N, 5.53 |
| Found: | C, 70.98; | H, 7.61; | N, 5.42 |

EXAMPLE 28

1-Acetyl-8-[1-oxo-3-[1-(phenylmethyl)piperidin-4-yl]propyl]-2,3,4,5-tetrahydro-1H-1-benzazepine

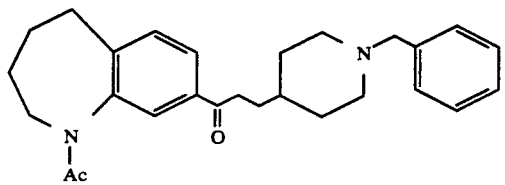

Using 0.3 g of 8-[1-oxo-3-[1-(phenylmethyl)piperidin-4-yl]propyl]-2,3,4,5-tetrahydro-1H-1-benzazepine, which is a free base of the compound obtained in Example 19 compound No. 16, the procedure of Example 16 was followed to give 0.21 g of the title compound as a colorless powder, m.p. 115°-116° C.

| Elemental Analysis, for $C_{27}H_{34}N_2O_2$ | | | |
|---|---|---|---|
| Calcd.: | C, 77.48; | H, 8.19; | N, 6.69 |
| Found: | C, 77.21; | H, 7.98; | N, 6.56 |

EXAMPLE 29

3,4-Dihydro-6-[1-oxo-3-(piperidin-4-yl)prop-yl]-2H-1-benzothiopyran hydrochloride

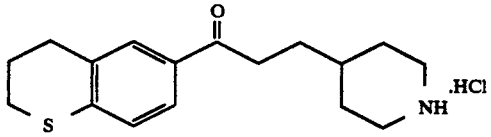

Using 2.5 g of the compound obtained in Reference Example 12, the procedure of Example 1 was followed to give 2.4 g of the title compound as a colorless powder, m.p. 196°-199° C.

| Elemental analysis, for $C_{24}H_{29}NOS \cdot HCl$: | | | |
|---|---|---|---|
| Calcd.: | C, 62.65; | H, 7.42; | N, 4.30 |
| Found: | C, 62.61; | H, 7.33; | N, 4.27 |

EXAMPLE 30

3,4-Dihydro-6-[1-oxo-3-[1-(phenylmethyl)piperidin-4-yl]propyl]-2H-1-benzothiopyran hydrochloride

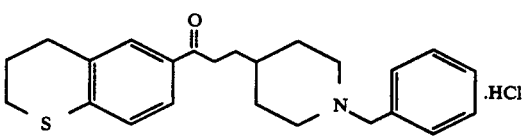

Using 0.83 g of the compound obtained in Example 29, the procedure of Example 2 was followed to give 1.0 g of the title compound as a colorless powder, m.p. 186°-188° C.

| Elemental analysis, for $C_{24}H_{29}NOS \cdot HCl$: | | | |
|---|---|---|---|
| Calcd: | C, 69.29; | H, 7.27; | N, 3.37 |
| Found: | C, 69.31; | H, 7.22; | N, 3.27 |

EXAMPLE 31

8-[1-Oxo-3-(piperidin-4-yl)propyl]-2,3,4,5-tetrahydro-1H-2-benzazepine dihydrochloride (A) and
7-[1-oxo-3-(piperidine-4-yl)propyl]-2,3,4,5-tetrahydro-1H-2-benzazepine dihydrochloride (B)

(A)

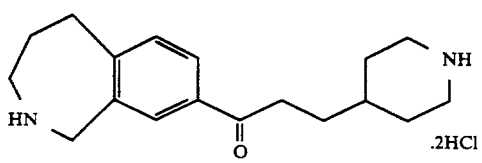

(B)

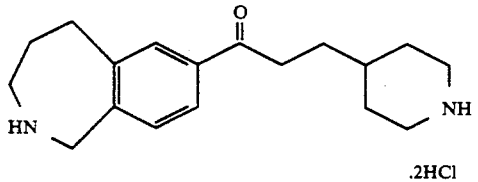

Using 5.0 g of 2-acetyl-2,3,4,5-tetrahydro-1H-2-benzazepine, the procedure of Reference Example 1 was followed to give 4.7 g of a viscous oil.

Using 4.5 g of the oil, the procedure of Example 1 was followed to give 3.3 g of a pale yellow solid. The solid was recrystallized from methanol to give the title compound (A) as colorless powder, m.p. >300° C.

| Elemental analysis, for C₁₈H₂₆N₂O.2HCl: | | | |
|---|---|---|---|
| Calcd.: | C, 60.17; | H, 7.85; | N, 7.80. |
| Found: | C, 60.02; | H, 7.3; | N, 7.69. |

From the mother liquor, the title compound (B) was obtained as an amorphous powder.

| Elemental analysis, for C₁₈H₂₆N₂O.2HCl: | | | |
|---|---|---|---|
| Calcd.: | C, 60.17; | H, 7.85; | N, 7.80. |
| Found: | C, 59.95; | H, 7.98; | N, 7.77. |

EXAMPLE 32

8-[1-Oxo-3-[1-(phenylmethyl)piperidin-4-yl]propyl]-2-(phenylmethyl)-2,3,4,5-tetrahydro-1H-2-benzazepine dihydrochloride (A) and
8-[1-oxo-3-[1-(phenylmethyl)piperidin-4-yl]propyl]-2,3,4,5-tetrahydro-1H-2-benzazepine dihydrochloride (B)

(A)

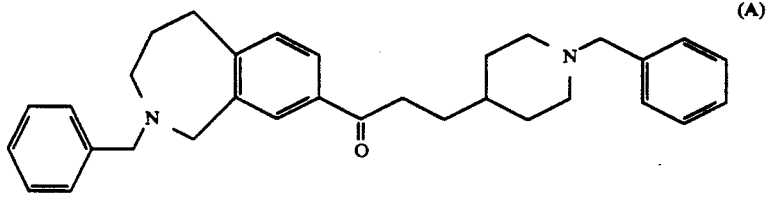

(B)

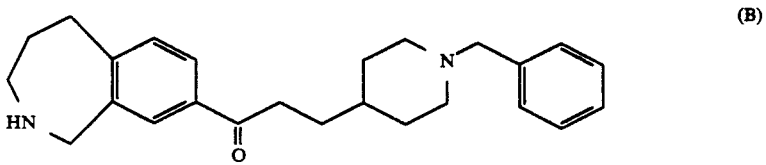

Using 1.5 g of 8-[1-oxo-3-(piperidin-4-yl)propyl]-2,3,4,5-tetrahydro-1H-2-benzazepine Dihydrochloride obtained in Example 31, the procedure of Example 2 was followed to give 0.5 g of the title compound (A) as an amorphous powder and 0.1 g of the title compound (B) as an amorphous powder.

8-[1-Oxo-3-(1-(phenylmethyl)piperidin-4-yl)propyl]-2-(phenylmethyl)-2,3,4,5-tetrahydro-1H-2-benzazepine dihydrochloride (A)

| Elemental analysis, for C₃₂H₃₈N₂O.2HCl: | | | |
|---|---|---|---|
| Calcd.: | C, 71.23; | H, 7.47; | N, 5.19. |
| Found: | C, 66.72; | H, 7.69; | N, 6.01. |

8-[1-Oxo-3-(1-(phenylmethyl)piperidin-4-yl)propyl]-2,3,4,5-tetrahydro-1H-2-benzazepine dihydrochloride (B)

| Elemental analysis, for C₂₅H₃₂N₂O.2HCl: | | | |
|---|---|---|---|
| Calcd.: | C, 66.81; | H, 7.62; | N, 6.23. |
| Found: | C, 66.72; | H, 7.69; | N, 6.01. |

EXAMPLE 33

8-Chloro-5-[1-oxo-3-[1-(phenylmethyl)piperidin-4-yl]propyl]-1,2,3,4-tetrahydroisoquinoline Dihydrochloride

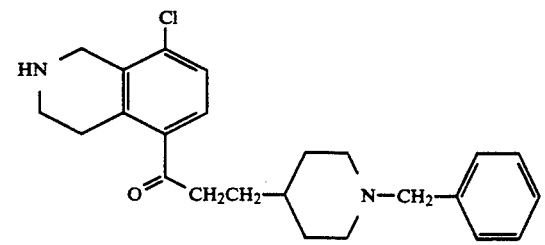

To a solution of 5.99 g (13.22 mmol) of the compound obtained in Reference Example 14 in 198 ml of methanol was added 99 ml of 1N aqueous NaOH. The mixture was stirred at 60° C. for 5 hours. After removal of methanol under reduced pressure, the aqueous residue was extracted with dichloromethane. The extracts were dried over anhydrous sodium sulfate and the solvent was distilled off. The residue was purified by means of a silica gel column chromatography (eluent; ethyl acetate:methanol=7:3(v/v)) to give 2.59 g of 5-[3-(1-benzoylpiperidin-4-yl)-1-oxopropyl]-8-chloro-1,2,3,4-tetrahydroisoquinoline.

To a solution of 1.23 g (3.0 mmol) of the compound obtained above in 10 ml of methanol was added 0.75 ml of 4N methanolic HCl at 5° C. and the solvent was distilled off. To the residual oil was added 60 ml of toluene, 8.24 ml of ethylene glycol, and 57 mg of p-toluenesulfonic acid monohydrate. The mixture was refluxed for 2 hours. To the reaction mixture was added a saturated aqueous solution of $NaHCO_3$, which was subjected to extraction with dichloromethane. The extracts were dried over anhydrous sodium sulfate, then the solvent removed under reduced pressure. The residue was purified by means of a silica gel column chromatography (eluent; ethyl acetate: methanol=7:3(v/v) to give 1.31 g of 5-[2-[2-(1-benzoylpiperidin-4-yl)ethyl]-1,3-dioxoran-2-yl]-8-chloro-1,2,3,4-tetrahydroisoquinoline.

Under nitrogen atmosphere, to a solution of 455 mg (1.0 mg) of the compound obtained above in 10 ml of dry tetrahydrofuran was added 127 μl of chloro trimethylsilane at 5° C. and the mixture was stirred at room temperature for 1 hour. Then to the reaction mixture was added 190 mg of lithium aluminum hydride and the mixture was refluxed for 2.5 hours. Water was added to the mixture and the resulting precipitate was removed by filtration. The filtrate was dried over anhydrous sodium sulfate, and the solvent was removed under reduced pressure. A mixture of the residue and 5 ml of 1N aqueous HCl in 5 ml of tetrahydrofuran was heated at 60° C. for 3 hours. The reaction mixture was made basic with a dilute aqueous NaOH, followed by extraction with dichloromethane. The extract was dried over anhydrous sodium sulfate, then the solvent was removed under reduced pressure to give 200 mg of a colorless oil, which was treated with 4N-methanolic HCl (2 equivalent) to give 205 mg of the title compound as an amorphous powder.

| Elemental analysis, for $C_{24}H_{29}ClN_2O \cdot 2HCl$: | | | |
|---|---|---|---|
| Calcd.: | C, 61.35; | H, 6.65; | N, 5.96. |
| Found: | C, 61.42; | H, 6.69; | N, 5.91. |

FORMULATION EXAMPLE 1

(1)
6-[3-[1-(Phenylmethyl)piperidin-4-yl]-1-oxopropyl]-1,2,3,4-tetrahydroquinoline bihydrochloride

| (the compound obtained in Example 2) | 1 g |
|---|---|
| (2) Lactose | 197 g |
| (3) Corn starch | 50 g |
| (4) Magnesium stearate | 2 g |

(1), (2) and 20 g of corn starch were blended and the mixture was granulated with a paste prepared from 15 g of corn starch and 25 ml of water. To this granular product were added 15 g of corn starch and (4) and the resulting composition was compression-molded to provide 2000 tables each measuring 3 mm in diameter and containing 0.5 mg of (1).

FORMULATION EXAMPLE 2

(1)
6-[3-[1-(Phenylmethyl)piperidin-4-yl]-1-oxopropyl]-1,2,3,4-tetrahydroquinoline dihydrochloride

| (the compound obtained in Example 2) | 2 g |
|---|---|
| (2) Lactose | 196 g |
| (3) Corn starch | 50 g |
| (4) Magnesium stearate | 2 g |

(1), (2) and 20 g of corn starch were blended and the mixture was granulated with a paste prepared from 15 g of corn starch and 25 ml of water. To this granular product were added 15 g of corn starch and (4) and the resulting composition was compression-molded to provide 2000 tablets each measuring 5 mm in diameter and containing 1 mg of (1).

FORMULATION EXAMPLE 3

(1)
8-[1-Oxo-3-[1-(Phenylmethyl)piperidin-4-yl]propyl]-2,3,4,5-tetrahydro-1H-1-benzazepine fumarate (the compound obtained in Example 19 compound No. 16)

| (the compound obtained in Example 19 compound No. 16) | 1 g |
|---|---|
| (2) Lactose | 197 g |
| (3) Corn starch | 50 g |
| (4) Magnesium stearate | 2 g |

(1), (2) and 20 g of corn starch were blended and the mixture was granulated with a paste prepared from 15 g of corn starch and 25 ml of water. To this granular product were added 15 g of corn starch and (4) and the resulting composition was compression-molded to provide 1000 tablets each measuring 3 mm in diameter and containing 1.0 mg of (1).

FORMULATION EXAMPLE 4

(1)
7-[1-Oxo-3-[1-(phenylmethyl)piperidin-4-yl]propyl]-2,3,4,5-tetrahydro-1H-3-benzazepine dihydrochloride (the compound obtained in Example 22)

| (the compound obtained in Example 22) | 2 g |
|---|---|
| (2) Lactose | 196 g |
| (3) Corn starch | 50 g |
| (4) Magnesium stearate | 2 g |

(1), (2) and 20 g of corn starch were blended and the mixture was granulated with a paste prepared from 15 g of corn starch and 25 ml of water. To this granular product were added 15 g of corn starch and (4) and the resulting composition was compression-molded to provide 2000 tablets each measuring 5 mm in diameter and containing 1 mg of (1).

FORMULATION EXAMPLE 5

8-[1-Oxo-3-[1-(phenylmethyl)piperidin-4-yl]propyl]-2,3,4,5-tetrahydro-1H-1-benzazepine fumarate (the compound obtained in Example 19, compound No. 16) (2 g) and 1.25 g of mannitol were dissolved in 500 ml of distilled water, pH was adjusted to 5.6 to 7 with 0.1N NaOH and the total amount of the solution was made up to 1000 ml. The solution thus obtained was sterilized by filtration through a filter of 0.2 μm. The resulting solution was distributed to provide 1000 of 1 ml-ampoules.

EXPERIMENTAL EXAMPLE

The cholinesterase inhibitory activity of the compound of the present invention was assayed with (acetyl-[3H])-acetylcholine. Thus, using the $S_1$ fraction of a homogenate of male Wistar rat cerebral cortex as the cholinesterase source, (acetyl-[3H])-acetylcholine and the compound of the invention were added as the substrate and the test substance, respectively, and the mixture was incubated for 30 minutes. After the reaction was terminated, a toluene-based scintillant was added and, after shaking, the reaction product [3H]-acetic acid which was transferred to the toluene layer was determined with a scintillation counter to estimate the cholinesterase activity.

The cholinesterase inhibitory activity of the test compound was expressed in 50% inhibitory concentration ($IC_{50}$) The cholinesterase inhibitory activity of physostigmine was also determined by the same procedure.

The results are shown in Table 1.

TABLE 1

| Compound (Example No.) | Acetylcholinesterase inhibitory activity $IC_{50}$ (μM) |
|---|---|
| 2 | 0.014 |
| 3 | 0.12 |
| 4 | 0.010 |
| 6-A | 0.054 |
| 6-B | 0.054 |
| 8-A | 0.024 |
| 8-B | 0.036 |
| 10 | 0.16 |
| 13 | 0.020 |
| 14 | 0.010 |
| 15 | 0.068 |
| 16 | 0.014 |
| 19-4 | 0.076 |
| 19-5 | 0.059 |
| 19-7 | 0.050 |
| 19-8 | 0.016 |
| 19-9 | 0.064 |
| 19-11 | 0.011 |
| 19-12 | 0.022 |
| 19-13 | 0.029 |
| 19-14 | 0.047 |
| 19-15 | 0.028 |
| 19-16 | 0.102 |
| 19-17 | 0.081 |
| 19-20 | 0.125 |
| 19-21 | 0.145 |
| 21 | 0.028 |
| 22 | 0.0076 |
| 23 | 0.0065 |
| 25 | 0.113 |
| 27 | 0.127 |
| Physostigmine | 0.22 |

The above results indicate that the compound of the present invention has excellent chloinesterase inhibitory activity.

The compound of the present invention has effects on the central nervous system of mammalian animals and exhibits potent cholinesterase inhibitory activity. Therefore, the compound can be used for the prevention and treatment of senile dementia, Alzheimer's disease, Huntington's chorea and other diseases related to brain dysfunction and is, therefore, of value as a medicament.

What is claimed is:

1. A condensed heterocyclic compound of the formula (I):

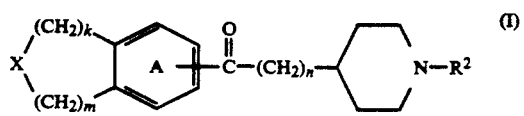

wherein X is an oxygen atom, a sulfur atom or $R^1$—N< wherein $R^1$ is a hydrogen atom, a hydrocarbon group which may be substituted or an optionally substituted acyl group which is (1) a $C_{2-8}$ alkylcarbonyl or phenylcarbonyl, (2) a $C_{1-7}$ alkylsulfonyl or phenylsulfonyl, (3) a $C_{1-7}$ alkylphosphonyl or phenylphosphonyl or (4) a $C_{2-8}$ alkyloxycarbonyl or $C_{7-8}$ aralkyloxy-carbonyl group; $R^2$ is a hydrogen atom or a hydrocarbon group which may be substituted; ring A is a benzene ring which may be substituted; k is a whole number of 0 t 3; m is a whole number of 1 to 8; and n is a whole number of 1 to 6, or a pharmaceutically acceptable salt thereof.

2. A compound as claimed in claim 1, wherein X is $R^1$—N< wherein $R^1$ is as defined in claim 1.

3. A compound as claimed in claim 2, wherein k is 0 and m is 2 to 7.

4. A compound as claimed in claim 1, wherein $R^1$ is a hydrogen atom.

5. A compound as claimed in claim 1, wherein $R^1$ is a hydrocarbon group which may be substituted.

6. A compound as claimed in claim 1, wherein $R^1$ is an acyl group which may be substituted.

7. A compound as claimed in claim 1, wherein $R^2$ is a hydrocarbon group which may be substituted.

8. A compound as claimed in claim 1, wherein the hydrocarbon group denoted by $R^1$ and $R^2$ is (1) a straightchain or branched $C_{1-11}$ alkyl, $C_{2-4}$ alkenyl or $C_{2-4}$ alkynyl group, (2) a $C_{3-7}$ monocyclic cycloalkyl group, (3) a $C_{8-14}$ bridged cyclic saturated hydrocarbon group, (4) a phenyl or naphthyl group or (5) a $C_{7-18}$ aralkyl, $C_{8-18}$ arylalkenyl, $C_{8-18}$ arylalkynyl or $C_{3-7}$ cycloalkyl-$C_{1-6}$ alkyl group.

9. A compound as claimed in claim 1, wherein $R^1$ is (1) a hydrogen atom, (2) a straight-chain or branched $C_{1-11}$ alkyl, $C_{2-4}$ alkenyl or $C_{2-4}$ alkynyl group which may be substituted by 1 to 5 substituents selected from the group consisting of a halogen, nitro, cyano, hydroxy, $C_{1-4}$ alkoxy, $C_{1-4}$ alkylthio, amino, mono- or di-$C_{1-4}$ alkyl-substituted amino, cyclic amino, $C_{1-4}$ alkylcarbonylamino, $C_{1-4}$ alkylsulfonylamino, $C_{1-4}$ alkoxycarbonyl, $C_{1-6}$ alkylcarbonyl, carbamoyl, mono- or di-$C_{1-4}$ alkyl-substituted carbamoyl and $C_{1-6}$ alkylsulfonyl, (3) a $C_{3-7}$ monocyclic cycloalkyl group which may be substituted by 1 to 5 substituents selected from the group consisting of a halogen, nitro, cyano, hydroxy, $C_{1-4}$ alkoxy, $C_{1-4}$ alkylthio, amino, mono- or di-$C_{1-4}$ alkyl-substituted amino, cyclic amino, $C_{1-4}$ alkylcarbonylamino, $C_{1-4}$ alkylsulfonylamino, $C_{1-4}$ alkoxycarbonyl, $C_{1-6}$ alkylcarbonyl, carbamoyl, mono- or di-$C_{1-4}$ alkyl-substituted carbamoyl and $C_{1-6}$ alkylsulfonyl, (4) a $C_{8-14}$ bridged cyclic saturated hydrocarbon group which may be substituted by 1 to 5 substituents selected from the group consisting of a halogen, nitro, cyano, hydroxy, $C_{1-4}$ alkoxy, $C_{1-4}$ alkylthio, amino, mono- or di-$C_{1-4}$ alkyl-substituted amino, cyclic amino, $C_{1-4}$ alkylcarbonylamino, $C_{1-4}$ alkylsulfonylamino, $C_{1-4}$ alkoxycarbonyl, $C_{1-6}$ alkylcarbonyl, carbamoyl, mono- or di-$C_{1-4}$ alkyl-substituted carbamoyl and $C_{1-6}$ alkylsulfonyl, (5) a phenyl or naphthyl group which may be substituted by 1 to 3 substituents selected from the group consisting of a $C_{1-4}$ alkyl, halogen, nitro, cyano, hydroxy, $C_{1-4}$ alkoxy, $C_{1-4}$ alkylthio, amino, mono- or di-$C_{1-4}$ alkyl-substituted amino, cyclic amino, $C_{1-4}$ alkylcarbonylamino, aminocarbonyloxy, mono- or di-$C_{1-4}$ alkyl-substituted aminocarbonyloxy, $C_{1-4}$ alkylsulfonylamino, $C_{1-4}$ alkoxycarbonyl, hydroxycarbonyl, $C_{1-6}$ alkylcarbonyl, $C_{3-6}$ cycloalkylcarbonyl, carbamoyl, mono- or di-$C_{1-4}$ alkyl-substituted carbamoyl, $C_{1-6}$ alkylsulfonyl, $C_{3-6}$ cycloalkylsulfonyl and a phenyl, naphthyl, phenoxy, benzoyl, phenoxycarbonyl, phenyl-$C_{1-4}$ alkylcarbamoyl, phenylcarbamoyl, phenyl-$C_{1-4}$ alkylcarbonylamino, benzoylamino, phenyl-$C_{1-4}$ alkylsulfonyl, phenylsulfonyl, phenyl-$C_{1-4}$ alkylsulfinyl, phenyl-$C_{1-4}$ alkylsulfonylamino or phenylsulfonylamino which may be substituted by 1 to 4 substituents selected from the group consisting of a $C_{1-4}$ alkyl, $C_{1-4}$ alkoxy, halogen, hydroxy, benzyloxy, amino, mono- or di-$C_{1-4}$ alkyl-substituted amino, nitro and $C_{1-6}$ alkylcarbonyl, (6) a $C_{7-18}$ aralkyl, $C_{8-18}$ arylalkenyl, $C_{8-18}$ arylalkynyl or $C_{3-7}$ cycloalkyl-$C_{1-6}$ alkyl group which may be substituted by 1 to 5 substituents selected from the group consisting of a $C_{1-4}$ alkyl, halogen, nitro, cyano, hydroxy, $C_{1-4}$ alkoxy, $C_{1-4}$ alkylthio, amino, mono- or di-$C_{1-4}$ alkyl-substituted amino, cyclic amino, $C_{1-4}$ alkylcarbonylamino, aminocarbonyloxy, mono- or di-$C_{1-4}$ alkyl-substituted aminocarbonyloxy, $C_{1-4}$ alkylsulfonylamino, $C_{1-4}$ alkoxycarbonyl, hydroxycarbonyl, $C_{1-6}$ alkylcarbonyl, $C_{3-6}$ cycloalkylcarbonyl, carbamoyl, mono- or di-$C_{1-4}$ alkyl-substituted carbamoyl, $C_{1-6}$ alkylsulfonyl, $C_{3-6}$ cycloalkylsulfonyl and a phenyl, naphthyl, phenoxy, benzoyl, phenoxycarbonyl, phenyl-$C_{1-4}$ alkylcarbamoyl, phenylcarbamoyl, phenyl-$C_{1-4}$ alkylcarbonylamino, benzoylamino, phenyl-$C_{1-4}$ alkylsulfonyl, phenylsulfonyl, phenyl-$C_{1-4}$ alkylsulfinyl, phenyl-$C_{1-4}$ alkylsulfonylamino or phenylsulfonylamino which may be substituted by 1 to 4 substituents selected from the group consisting of a $C_{1-4}$ alkyl, $C_{1-4}$ alkoxy, halogen, hydroxy, benzyloxy, amino, mono- or di-$C_{1-4}$ alkyl-substituted amino, nitro and $C_{1-6}$ alkylcarbonyl, (7) $C_{2-8}$ alkylcarbonyl or phenylcarbonyl group which may be substituted by 1 to 3 substituents selected from the group consisting of a halogen, amino, $C_{1-6}$ alkyl- or $C_{3-6}$ cycloalkyl-substituted primary or secondary amino and $C_{1-4}$ alkoxy, (8) a $C_{1-7}$ alkylsulfonyl or phenylsulfonyl group which may be substituted by 1 to 3 substituents selected from the group consisting of a halogen, amino, $C_{1-6}$ alkyl- or $C_{3-6}$ cycloalkyl-substituted primary or secondary amino and $C_{1-4}$ alkoxy, (9) a $C_{1-7}$ alkylphosphonyl or phenylphosphonyl group which may be substituted by 1 to 3 substituents selected from the group consisting of a halogen, amino, $C_{1-6}$ alkyl- or $C_{3-6}$ cycloalkyl-substituted primary or secondary amino and $C_{1-4}$ alkoxy, or (10) a $C_{2-8}$ alkyloxycarbonyl or $C_{7-8}$ aralkyloxy-carbonyl group which may be substituted by 1 to 3 substituents selected from the group consisting of a halogen, amino, $C_{1-6}$ alkyl- or $C_{3-6}$ cycloalkyl-substituted primary or secondary amino and $C_{1-4}$ alkoxy; $R^2$ is (1) a hydrogen atom, (2) a straightchain or branched $C_{1-11}$ alkyl, $C_{2-4}$ alkenyl or $C_{2-4}$ alkynyl group which may be substituted by 1 to 5 substituents selected from the group consisting of a halogen, nitro, cyano, hydroxy, $C_{1-4}$ alkoxy, $C_{1-4}$ alkylthio, amino, mono- or di-$C_{1-4}$ alkyl-substituted amino, cyclic amino, $C_{1-4}$ alkylcarbonylamino, $C_{1-4}$ alkylsulfonylamino, $C_{1-4}$ alkoxycarbonyl, $C_{1-6}$ alkylcarbonyl, carbamoyl, mono- or di-$C_{1-4}$ alkyl-substituted carbamoyl and $C_{1-6}$ alkylsulfonyl, (3) a $C_{3-7}$ monocyclic cycloalkyl group which may be substituted by 1 to 5 substituents selected from the group consisting of a halogen, nitro, cyano, hydroxy, $C_{1-4}$ alkoxy, $C_{1-4}$ alkylthio, amino, mono- or di-$C_{1-4}$ alkyl-substituted amino, cyclic amino, $C_{1-4}$ alkylcarbonylamino, $C_{1-4}$ alkylsulfonylamino, $C_{1-4}$ alkoxycarbonyl, $C_{1-6}$ alkylcarbonyl, carbamoyl, mono- or di-$C_{1-4}$ alkyl-substituted carbamoyl and $C_{1-6}$ alkylsulfonyl, (4) a $C_{8-14}$ bridged cyclic saturated hydrocarbon group which may be substituted by 1 to 5 substituents selected from the group consisting of a halogen, nitro, cyano, hydroxy, $C_{1-4}$ alkoxy, $C_{1-4}$ alkylthio, amino, mono- or di-$C_{1-4}$ alkyl-substituted amino, cyclic amino, $C_{1-4}$ alkylcarbonylamino, $C_{1-4}$ alkylsulfonylamino, $C_{1-4}$ alkoxycarbonyl, $C_{1-6}$ alkylcarbonyl, carbamoyl, mono- or di-$C_{1-4}$ alkyl-substituted carbamoyl and $C_{1-6}$ alkylsulfonyl, (5) a phenyl or naphthyl group which may be substituted by 1 to 3 substituents selected from the group consisting of a $C_{1-4}$ alkyl, halogen, nitro, cyano, hydroxy, $C_{1-4}$ alkoxy, $C_{1-4}$ alkylthio, amino, mono- or di-$C_{1-4}$ alkyl-substituted amino, cyclic amino, $C_{1-4}$ alkylcarbonylamino, aminocarbonyloxy, mono- or di-$C_{1-4}$ alkyl-substituted aminocarbonyloxy, $C_{1-4}$ alkylsulfonylamino, $C_{1-4}$ alkoxycarbonyl, hydroxycarbonyl, $C_{1-6}$ alkylcarbonyl, $C_{3-6}$ cycloalkylcarbonyl, carbamoyl, mono- or di-$C_{1-4}$ alkyl-substituted carbamoyl, $C_{1-6}$ alkylsulfonyl, $C_{3-6}$ cycloalkylsulfonyl and a phenyl, naphthyl, phenoxy, benzoyl, phenoxycarbonyl, phenyl-$C_{1-4}$ alkylcarbamoyl, phenylcarbamoyl, phenyl-$C_{1-4}$ alkylcarbonylamino, benzoylamino, phenyl-$C_{1-4}$ alkylsulfonyl, phenylsulfonyl, phenyl-$C_{1-4}$ alkylsulfinyl, phenyl-$C_{1-4}$ alkylsulfonylamino or phenylsulfonylamino which may be substituted by 1 to a 4 substituents selected from tho group consisting of $C_{1-4}$ alkyl, $C_{1-4}$ alkoxy, halogen, hydroxy, benzyloxy, amino, mono- or di-$C_{1-4}$ alkyl-substituted amino, nitro and $C_{1-6}$ alkylcarbonyl, or (6) a $C_{7-18}$ aralkyl, $C_{8-18}$ arylalkenyl, $C_{8-18}$ arylalkynyl or $C_{3-7}$ cycloalkyl-$C_{1-6}$ alkyl group which may be substituted by 1 to 5 substituents selected from the group consisting of a $C_{1-4}$ alkyl, halogen, nitro, cyano, hydroxy, $C_{1-4}$ alkoxy, $C_{1-4}$ alkylthio, amino, mono- or di-$C_{1-4}$ alkyl-substituted amino, cyclic amino, $C_{1-4}$ alkylcarbonylamino, aminocarbonyloxy, mono- or di-$C_{1-4}$ alkyl-substituted aminocarbonyloxy, $C_{1-4}$ alkylsulfonylamino, $C_{1-4}$ alkoxycarbonyl, hydroxycarbonyl, $C_{1-6}$ alkylcarbonyl, $C_{3-6}$ cycloalkylcarbonyl, carbamoyl, mono- or di-$C_{1-4}$ alkyl-substituted carbamoyl, $C_{1-6}$ alkylsulfonyl, $C_{3-6}$ cycloalkylsulfonyl and a phenyl, naphthyl, phenoxy, benzoyl, phenoxycarbonyl, phenyl-$C_{1-4}$ alkylcarbamoyl, phenylcarbamoyl, phenyl-$C_{1-4}$ alkylcarbonylamino, benzoylamino, phenyl-$C_{1-4}$ alkylsulfonyl, phenylsulfonyl, phenyl-$C_{1-4}$ alkylsulfinyl, phenyl-$C_{1-4}$ alkylsulfonylamino or phenylsulfonylamino which may be substituted by 1 to 4 substituents selected from the group consisting of $C_{1-4}$ alkyl, $C_{1-4}$ alkoxy, halogen, hydroxy, benzyloxy, amino, mono- or di-$C_{1-4}$ alkyl-substituted amino, nitro and $C_{1-6}$ alkylcarbonyl; and ring A is a benzene ring which may be substituted by 1 to 3 substituents selected from the group consisting of a $C_{1-4}$ alkyl, halogen, nitro, cyano, hydroxy, $C_{1-4}$ alkoxy, $C_{1-4}$ alkylthio, amino, mono- or di-$C_{1-4}$ alkyl-substituted amino, cyclic amino, $C_{1-4}$ alkylcarbonylamino, aminocarbonyloxy, mono- or di-$C_{1-4}$ alkyl-substituted aminocarbonyloxy, $C_{1-4}$ alkylsulfonylamino, $C_{1-4}$ alkoxycarbonyl, hydroxycarbonyl, $C_{1-4}$ alkylcarbonyl, $C_{3-6}$ cycloalkylcarbonyl, carbamoyl, mono- or di-$C_{1-4}$ alkyl-substituted carbamoyl, $C_{1-6}$ alkylsulfonyl, $C_{3-6}$ cycloalkylsulfonyl and a phenyl, naphthyl, phenoxy, benzoyl, phenoxycarbonyl, phenyl-$C_{1-4}$ alkylcarbamoyl, phenylcarbamoyl, phenyl-$C_{1-4}$ alkylcarbonylamino, benzoylamino, phenyl-$C_{1-4}$ alkylsulfonyl, phenylsulfonyl, phenyl-$C_{1-4}$ alkylsulfinyl, phenyl-$C_{1-4}$ alkylsulfonylamino or phenylsulfonylamino which may be substituted by 1 to 4 substituents selected from the group consisting of a $C_{1-4}$ alkyl, $C_{1-4}$ alkoxy, halogen, hydroxy, benzyloxy, amino, mono- or di-$C_{1-4}$ alkyl-substituted amino, nitro and $C_{1-6}$ alkylcarbonyl.

10. A compound as claimed in claim 1, wherein k is 0 to 2 and m is 1 to 5.

11. A compound as claimed in claim 1, wherein k is 0 and m is 2 to 5.

12. A compound as claimed in claim 1, wherein X is an oxygen atom or $R^1$—N< wherein $R^1$ is as defined in claim 1; k is 0 to 2; m is 2 to 5; n is 1 to 3 and $R^2$ is a hydrogen atom or a $C_{7-10}$ aralkyl group which may be substituted by a $C_{1-4}$ alkyl, halogen, nitro or $C_{1-4}$ alkoxy.

13. A compound as claimed in claim 12, wherein $R^1$ is a hydrogen atom, a straight-chain or branched $C_{1-7}$ alkyl group, a $C_{7-10}$ aralkyl group or a $C_{2-8}$ alkylcarbonyl group.

14. A compound as claimed in claim 1, wherein n is 2 and $R_2$ is a benzyl group.

15. A compound as claimed in claim 1, wherein

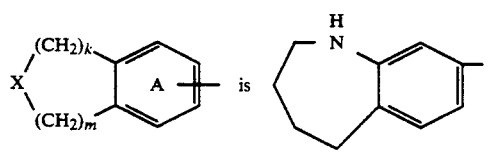

16. A compound as claimed in claim 1, wherein

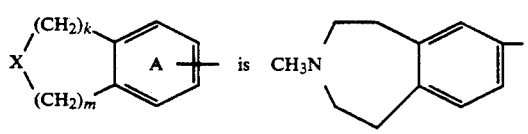

17. A compound as claimed in claim 1, wherein

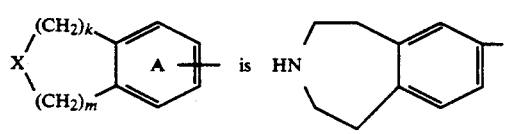

18. A compound as claimed in claim 1, wherein

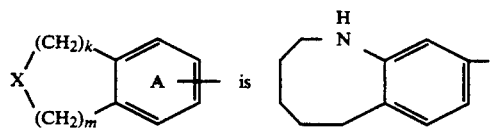

19. A compound as claimed in claim 1, wherein

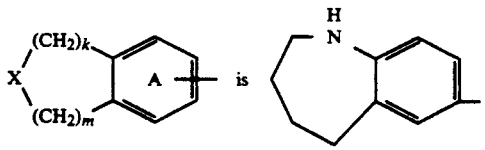

20. A compound as claimed in claim 1, wherein

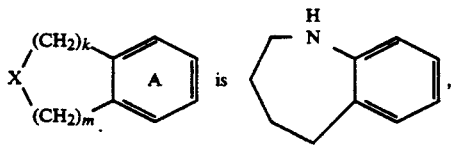

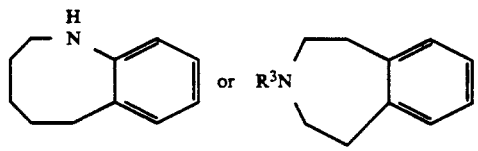

wherein $R^3$ is a hydrogen atom or a $C_{1-3}$ alkyl group; n is 2 and $R^2$ is a benzyl group.

21. A compound as claimed in claim 1, which is 8-[1-oxo-3-[1-(phenylmethyl)piperidin-4-yl]propyl]-2,3,4,5-tetrahydro-1H-1-benzazepine or a pharmaceutically acceptable salt thereof.

22. A compound as claimed in claim 1, which is 3-methyl-7-[1-oxo-3-[1-(phenylmethyl)piperidin-4-yl]propyl]-2,3,4,5-tetrahydro-1H-3-benzazepine or a pharmaceutically acceptable salt thereof.

23. A compound as claimed in claim 1, which is 7-[1-oxo-3-[1-(phenylmethyl)piperidin-4-yl]propyl]-2,3,4,5-tetrahydro-1H-3-benzazepine or a pharmaceutically acceptable salt thereof.

24. A compound as claimed in claim 1, which is 9-[1-oxo-3-[1-(phenylmethyl)piperidin-4-yl]propyl]-1,2,3-4,5,6-hexahydro-1-benzazocine or a pharmaceutically acceptable salt thereof.

25. A compound as claimed in claim 1, which is 7-[1-oxo-3-[1-phenylmethyl)piperidin-4-yl]propyl]-2,3,4,5-tetrahydro-1H-1-benzazepine or a pharmaceutically acceptable salt thereof.

26. A compound as claimed in claim 1, which is 8-[1-oxo-3-[1-(phenylmethyl)piperidin-4-yl]propyl]-2,3,4,5-tetrahydro-1H-1-benzazepine fumarate.

27. A compound as claimed in claim 1, which is 3-methyl-7-[1-oxo-3-[1-(phenylmethyl)piperidin-4-yl]propyl]-2,3,4,5-tetrahydro-1H-3-benzazepine dihydrochloride.

28. A compound as claimed in claim 1, which is 7-[1-oxo-3-[1-(phenylmethyl)piperidin-4-yl]propyl]-2,3,4,5-tetrahydro-1H-3-benzazepine fumarate.

29. A compound as claimed in claim 1, which is 9-[1-oxo-3-[1-(phenylmethyl)piperidin-4-yl]propyl]-1,2,3,4,5,6-hexahydro-1-benzazocine fumarate.

30. A compound as claimed in claim 1, which is 7-[1-oxo-3-[1-phenylmethyl)piperidin-4-yl]propyl]-2,3,4,5-tetrahydro-1H-1-benzazepine fumarate.

31. A cholinesterase inhibitor which contains a condensed heterocyclic compound of the formula (I) as claimed in claim 1 or a pharmaceutically acceptable salt thereof.

32. A pharmaceutical composition for inhibiting cholinesterase activity in a mammal in need thereof comprising a therapeutically effective amount of a compound of the formula (I) as claimed in claim 1 or a pharmaceutically acceptable salt thereof and a pharmacologically acceptable carrier.

33. A method for inhibiting cholinesterase activity comprising administering to a mammal in need thereof a therapeutically effective amount of a compound of the formula (I):

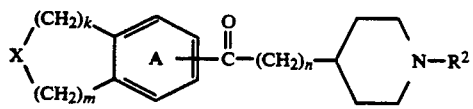

wherein X is an oxygen atom, a sulfur atom or $R^1$—N< wherein $R^1$ is a hydrogen atom, a hydrocarbon group which may be substituted or an optionally substituted acyl group which is (1) a $C_{2-8}$ alkylcarbonyl or phenylcarbonyl, (2) a $C_{1-7}$ alkylsulfonyl or phenylsulfonyl, (3) a $C_{1-7}$ alkylphosphonyl or phenylphosphonyl or (4) a $C_{2-8}$ alkyloxy-carbonyl or $C_{7-8}$ aralkyloxy-carbonyl group; $R^2$ is a hydrogen atom or a hydrocarbon group which may be substituted; ring A is a benzene ring which may be substituted; k is a whole number of 0 to 3; m is a while number of 1 to 8; and n is a whole number of 1 to 6, or a pharmaceutically acceptable salt thereof, together with a pharmaceutically acceptable carrier to a mammal suffering from such disease.

34. A compound as claimed in claim 1, wherein K is 0 to 2; m is 2 to 5; n is 1 to 3 and $R^2$ is a hydrogen atom or a $C_{7-10}$ aralkyl group which may be substituted by a $C_{1-4}$ alkyl, halogen, nitro or $C_{1-4}$ alkoxy.

35. A compound as claimed in claim 34, wherein $R^1$ is a hydrogen atom, a straight-chain or branched $C_{1-7}$ alkyl group, a $C_{7-10}$ aralkyl group or a $C_{2-8}$ alkylcarbonyl group.